(12) United States Patent
Rao et al.

(10) Patent No.: US 9,956,353 B2
(45) Date of Patent: May 1, 2018

(54) SHROUD DEPLOYMENT IN AUTOMATIC INJECTION DEVICES

(75) Inventors: Vivek Rao, Alameda, CA (US);
Sherwin Shang, Vernon Hills, IL (US);
Esra Ozdaryal, Deerfield, IL (US);
Eduard Tsvirko, Arlington Heights, IL (US); Edwin Chim, Vernon Hills, IL (US); David Post, Kenosha, WI (US);
Vincent Dipalma, Hayward, CA (US)

(73) Assignee: AbbVie Inc., North Chicago, IL (US)

( * ) Notice: Subject to any disclaimer, the term of this patent is extended or adjusted under 35 U.S.C. 154(b) by 238 days.

(21) Appl. No.: 14/007,849

(22) PCT Filed: Mar. 29, 2012

(86) PCT No.: PCT/US2012/031260
§ 371 (c)(1),
(2), (4) Date: Dec. 11, 2013

(87) PCT Pub. No.: WO2012/135524
PCT Pub. Date: Oct. 4, 2012

(65) Prior Publication Data
US 2014/0128840 A1 May 8, 2014

Related U.S. Application Data

(60) Provisional application No. 61/469,077, filed on Mar. 29, 2011.

(51) Int. Cl.
*A61M 5/32* (2006.01)
*A61M 5/20* (2006.01)

(52) U.S. Cl.
CPC ........ *A61M 5/3245* (2013.01); *A61M 5/2033* (2013.01); *A61M 5/3204* (2013.01);
(Continued)

(58) Field of Classification Search
CPC .......... A61M 5/2033; A61M 2005/206; A61M 2005/2073; A61M 2005/3267;
(Continued)

(56) References Cited

U.S. PATENT DOCUMENTS 3,910,260 A   10/1975  Sarnoff et al.
3,941,130 A   3/1976   Tibbs
(Continued)

FOREIGN PATENT DOCUMENTS

CN   101484199 A   7/2009
CN   101868269 A   10/2010
(Continued)

OTHER PUBLICATIONS

International Search Report for Application No. PCT/US2012/031260, dated Aug. 1, 2012, 3 pages.
(Continued)

*Primary Examiner* — Bhisma Mehta
*Assistant Examiner* — Brandy S Lee
(74) *Attorney, Agent, or Firm* — McCarter & English, LLP; David R. Burns

(57) ABSTRACT

Exemplary embodiments provide automatic injection devices in which a shroud is automatically deployed to protectively sheath a needle after an injection is performed. Exemplary embodiments also provide shroud deployment assemblies including a shroud and a syringe carrier that, when cooperatively configured in an automatic injection device, ensure that the shroud is automatically and completely deployed after an injection is performed using the automatic injection device. Exemplary embodiments are also configured to ensure that, once the shroud is deployed to an extended position to sheath the needle, accidental forces applied to the shroud do not succeed in subsequently
(Continued)

retracting the shroud to a retracted position in which the needle would become exposed.

42 Claims, 57 Drawing Sheets

(52) U.S. Cl.
CPC ....... *A61M 5/326* (2013.01); *A61M 2005/206* (2013.01); *A61M 2005/2073* (2013.01); *A61M 2005/3267* (2013.01); *Y10T 29/49826* (2015.01)

(58) Field of Classification Search
CPC .. A61M 5/3204; A61M 5/3245; A61M 5/326; Y10T 29/49826
See application file for complete search history.

(56) References Cited

U.S. PATENT DOCUMENTS

| | | | |
|---|---|---|---|
| 4,004,577 A | 1/1977 | Sarnoff | |
| 4,261,358 A | 4/1981 | Vargas et al. | |
| 4,689,042 A | 8/1987 | Sarnoff et al. | |
| 4,755,169 A | 7/1988 | Sarnoff et al. | |
| 4,795,433 A | 1/1989 | Sarnoff | |
| 5,085,642 A | 2/1992 | Sarnoff et al. | |
| 5,092,843 A | 3/1992 | Monroe et al. | |
| 5,102,393 A | 4/1992 | Sarnoff et al. | |
| 5,267,963 A | 12/1993 | Bachynsky | |
| 5,656,272 A | 8/1997 | Le et al. | |
| 6,090,382 A | 7/2000 | Salfeld et al. | |
| 6,149,626 A | 11/2000 | Bachynsky et al. | |
| 6,258,562 B1 | 7/2001 | Salfeld et al. | |
| 6,270,479 B1 | 8/2001 | Bergens et al. | |
| 6,371,939 B2 | 4/2002 | Bergens et al. | |
| 6,448,380 B2 | 9/2002 | Rathjen et al. | |
| 6,451,983 B2 | 9/2002 | Rathjen et al. | |
| 6,498,237 B2 | 12/2002 | Rathjen et al. | |
| 6,509,015 B1 | 1/2003 | Salfeld et al. | |
| 6,593,458 B1 | 7/2003 | Rathjen et al. | |
| 6,805,686 B1 | 10/2004 | Fathallah et al. | |
| 7,223,394 B2 | 5/2007 | Salfeld et al. | |
| 7,229,432 B2* | 6/2007 | Marshall | A61M 5/326 604/110 |
| 2005/0020979 A1 | 1/2005 | Westbye et al. | |
| 2010/0160894 A1* | 6/2010 | Julian | A61M 5/2033 604/506 |

FOREIGN PATENT DOCUMENTS

| | | |
|---|---|---|
| WO | 2004047892 A1 | 6/2004 |
| WO | 2005113039 A1 | 12/2005 |
| WO | 2008005315 A2 | 1/2008 |
| WO | 2012085580 A1 | 6/2012 |

OTHER PUBLICATIONS

Office Action issued in Chinese Application No. 201280026322.2 dated Mar. 10, 2015.
Office Action issued in Japanese Patent Application No. 2014-502806 dated Jan. 5, 2016.
Office Action issued in Mexican Patent Application No. MX/a/2013/011263 dated Jun. 14, 2016.

* cited by examiner

SHROUD DEPLOYMENT IN AUTOMATIC INJECTION DEVICES

RELATED APPLICATIONS

This application is a non-provisional of and claims priority to U.S. Provisional Patent Application No. 61/469,077, filed Mar. 29, 2011. This application is also related to U.S. patent application Ser. No. 12/770,557, filed Apr. 29, 2010. The entire contents of each aforementioned application are expressly incorporated herein by reference in their entirety.

BACKGROUND

Automatic injection devices offer an alternative to manually-operated syringes for delivering therapeutic agents into patients' bodies and allow patients to self-administer injections. Automatic injection devices have been used to deliver medications under emergency conditions, for example, to administer epinephrine to counteract the effects of a severe allergic reaction. Automatic injection devices have also been described for use in administering anti-arrhythmic medications and selective thrombolytic agents during a heart attack (See, e.g., U.S. Pat. Nos. 3,910,260; 4,004,577; 4,689,042; 4,755,169; and 4,795,433). Various types of automatic injection devices are also described in, for example, U.S. Pat. Nos. 3,941,130; 4,261,358; 5,085,642; 5,092,843; 5,102,393; 5,267,963; 6,149,626; 6,270,479; and 6,371,939; and International Patent Publication No. WO/2008/005315.

Conventionally, an automatic injection device includes a housing that houses a syringe and, when operated, causes the syringe to move forwardly within the housing and a needle to project from the housing so that a therapeutic agent contained in the syringe is ejected into a patient's body. An automatic injection device typically includes a plunger with a distal end that is seated on a firing body before firing. In order to fire the device, a patient depresses a firing button which disengages the distal end of the plunger from the firing body and allows the plunger to move the syringe forwardly. An automatic injection device may include a lockout shroud that is deployed during or after an injection to provide a protecting covering over the needle and to thereby prevent accidental needle stick injuries to the user.

Certain conventional automatic injection devices experience problematic shroud deployment including, but not limited to, complete failure in shroud deployment, incomplete shroud deployment, and complete or incomplete shroud deployment after an unacceptably long delay, and the like. Each of these problematic shroud deployment patterns may be referred to as shroud deployment failure or failure in shroud deployment. Shroud deployment failure is undesirable in automatic injection device as they can introduce the risk of accidental needle stick injury caused by an exposed needle.

SUMMARY

Exemplary embodiments provide automatic injection devices in which a shroud is automatically deployed to protectively sheath a needle after an injection is performed. Exemplary embodiments also provide shroud deployment assemblies including a shroud and a syringe carrier that, when cooperatively configured in an automatic injection device, ensure that the shroud is automatically and completely deployed after an injection is performed using the automatic injection device. Exemplary embodiments are also configured to ensure that, once the shroud is deployed to an extended position to sheath the needle, accidental forces applied to the shroud do not succeed in subsequently retracting the shroud to a retracted position in which the needle would become exposed.

In accordance with one exemplary embodiment, a shroud deployment assembly is provided for use in an automatic injection device. The shroud deployment assembly includes a shroud and a syringe carrier. The shroud is disposed within an internal bore of a housing of the automatic injection device, and is movable between a retracted position relative to the housing and an extended position relative to the housing. The shroud includes a tubular member extending between a proximal end and a distal end, and one or more arms extending from the distal end of the tubular member. The syringe carrier is coupled to and disposed partly within the tubular member of the shroud, and includes a cylindrical portion. As the shroud is deployed from the retracted position to the extended position, the arms of the shroud move forwardly within a constrained space formed between an inner surface of the housing of the automatic injection device and an outer surface of the cylindrical portion of the syringe carrier. The constrained space is maximized and configured to facilitate smooth movement of the arms of the shroud within the constrained space during deployment of the shroud, while ensuring proper lockout of the shroud in the extended position.

In accordance with another exemplary embodiment, an automatic injection device is provided. The automatic injection device includes a housing having an internal bore extending between a proximal end and a distal end. The automatic injection device also includes a shroud disposed within the internal bore at the proximal end of the housing of the automatic injection device. The shroud is movable between a retracted position relative to the housing and an extended position relative to the housing. The shroud includes a tubular member extending between a proximal end and a distal end, and one or more arms extending from the distal end of the tubular member. The automatic injection device also includes a syringe carrier disposed partly within the tubular member of the shroud, the syringe carrier comprising a tubular member. As the shroud is deployed from the retracted position to the extended position, the arms of the shroud move forwardly within a constrained space formed between an inner surface of the housing of the automatic injection device and an outer surface of the tubular member of the syringe carrier. The constrained space is maximized to facilitate movement of the arms of the shroud within the constrained space during deployment of the shroud, while ensuring proper lockout of the shroud in the extended position.

In accordance with another exemplary embodiment, a method is provided for forming an automatic injection device. The method includes providing a housing having an internal bore extending between a proximal end and a distal end, and disposing a shroud within the internal bore at the proximal end of the housing of the automatic injection device. The shroud is movable between a retracted position and an extended position relative to the housing, and includes a tubular member extending between a proximal end and a distal end, and one or more arms extending from the distal end of the tubular member. The method also includes disposing a syringe carrier partly within the tubular member of the shroud, the syringe carrier comprising a tubular member. The method further includes configuring a constrained space formed between the housing of the automatic injection device and the tubular member of the syringe carrier to minimize a pinching effect of the arms during its movement in the constrained space when moving from the retracted position to the extended position.

In accordance with another exemplary embodiment, a method is provided for using an automatic injection device for delivering an injection. The method includes providing a shroud having one or more arms within a housing of the automatic injection device, the shroud being in a retracted position relative to the housing to expose a needle through an open proximal end of the shroud. The method includes delivering an injection using the automatic injection device through the needle. The method also includes deploying the shroud from the retracted position to an extended position relative to the housing of the automatic injection device to protectively sheath the needle after the injection, the arms of the shroud moving forwardly within a constrained space formed between an inner portion of the housing of the automatic injection device and an outer portion of a tubular member of a syringe carrier. The constrained space and/or the arms of the shroud are configured to minimize a pinching effect of the arms during its movement in the constrained space.

In accordance with another exemplary embodiment, a syringe carrier assembly is provided for use in an automatic injection device. The syringe carrier assembly includes a proximal tubular portion having a first outer diameter, a distal tubular portion having a second outer diameter less than the first diameter, and a chamfered edge formed between the proximal and distal tubular portions. The syringe carrier assembly is disposed partly within a tubular member of a shroud. As the shroud moves from a retracted position relative to the housing to an extended position relative to the housing, distal arms of the shroud move forwardly within a constrained space formed between an inner portion of the housing of the automatic injection device and an external portion of the proximal tubular portion of the syringe carrier. The proximal tubular portion and/or the chamfered edge of the syringe carrier assembly are cooperatively coupled to exhibit a gradual downward force slope substantially along a distance as the shroud moves from the retracted position to the extended position.

In accordance with another exemplary embodiment, an automatic injection device is provided. The device includes a housing having an internal bore extending between a proximal end and a distal end, the internal bore including a flange having at least one opening. The device also includes a shroud disposed within the internal bore at the proximal end of the housing of the automatic injection device. The shroud is movable between a retracted position and an extended position relative to the housing. The shroud includes a tubular member extending between a proximal end and a distal end, and one or more arms extending from the distal end of the tubular member. As the shroud is deployed from the retracted position to the extended position, the arms of the shroud move forwardly through the opening in the flange of the housing. The flange is configured to minimize engagement of the arms with an edge of the flange to facilitate movement of the arms of the shroud through the opening of the flange during deployment of the shroud.

BRIEF DESCRIPTION OF THE DRAWINGS

The foregoing and other objects, aspects, features and advantages of exemplary embodiments will be more fully understood from the following description when read together with the accompanying drawings, in which.

DETAILED DESCRIPTION

Figures 1, 2:
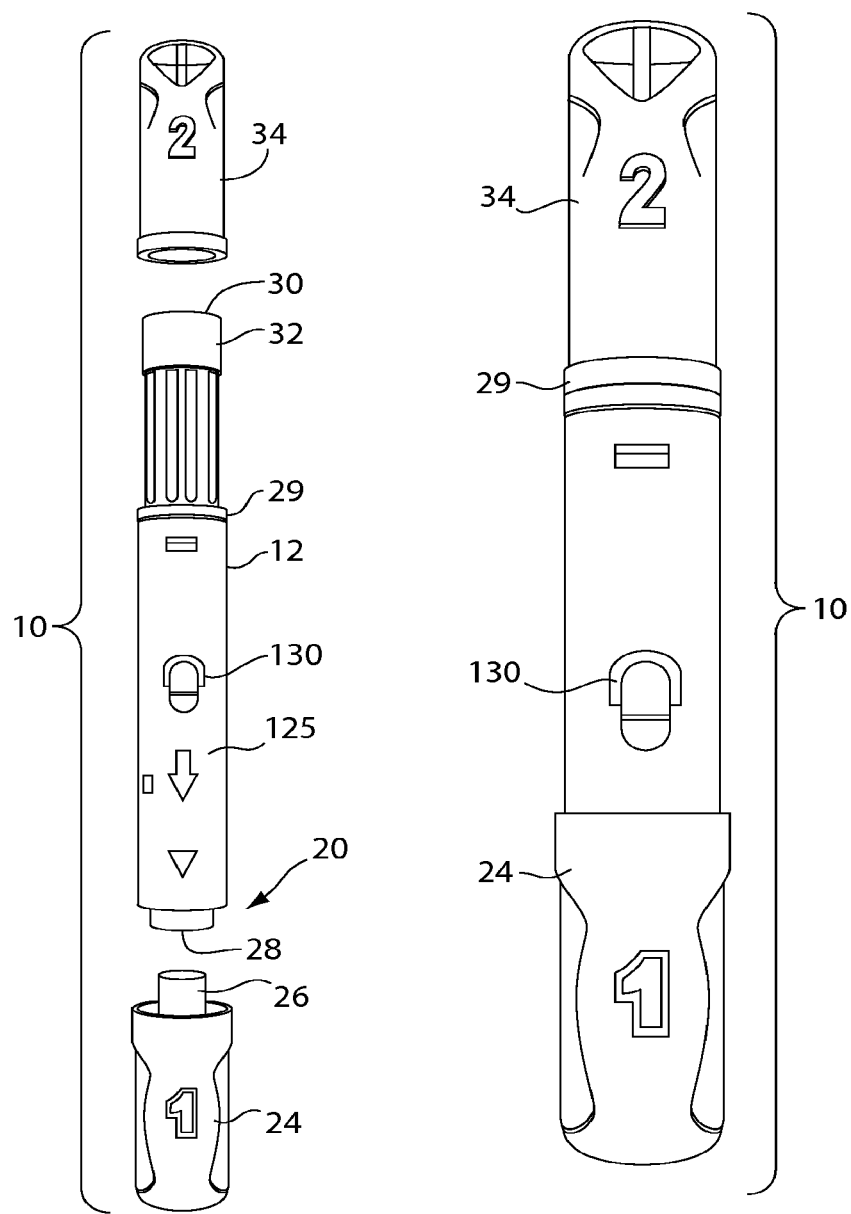
FIG. 1 illustrates a perspective view of an exemplary automatic injection device in which caps that cover proximal and distal ends of the housing are removed from the housing.
FIG. 2 illustrates a perspective view of the exemplary automatic injection device of FIG. 1 in which the housing is capped using proximal and distal caps.

Exemplary embodiments provide automatic injection devices in which a needle shroud is automatically deployed in a reliable and consistent manner to protectively sheath a needle after an injection is delivered using the automatic injection device. Exemplary embodiments also provide shroud deployment assemblies including a needle shroud and a syringe carrier that when cooperatively configured in an automatic injection device ensure that the needle shroud is automatically deployed in a reliable and consistent manner after an injection is delivered using the automatic injection device. Exemplary embodiments thereby avoid the risk of accidental needle injury caused by an exposed needle.

Exemplary embodiments are also configured to ensure that, once the shroud is deployed to an extended position to sheath the needle, accidental forces applied to the shroud do not succeed in subsequently retracting the shroud to a retracted position in which the needle would become exposed. Exemplary embodiments thereby avoid re-introduction of the risk of accidental needle stick injury. In some exemplary embodiments, the maximum force that an exemplary shroud, once deployed to an extended position, can reliably withstand without retracting back to a retracted position (referred to as the "override force") is about 80 N to about 120 N.

Exemplary embodiments may implement one or a combination of two or more of the structural, functional and operational configurations taught herein to minimize the risk of shroud deployment failure. Exemplary embodiments may also modify one or more conventional components of an automatic injection device in accordance with the teachings provided herein in order to minimize the risk of shroud deployment failure in the modified conventional components.

Automatic injection devices provided in accordance with exemplary embodiments may be used for administering any type of substance into a patient's body including, but not limited to, liquid therapeutic agents, e.g., adalimumab (HUMIRA®), golimumab, etc.

I. DEFINITIONS

Certain terms are defined in this section to facilitate understanding of exemplary embodiments.

The terms "automatic injection device," "autoinjector" and "autoinjector pen" refer to a device that enables a patient to self-administer a dose of a substance, such as a liquid medication, wherein the automatic injection device differs from a standard syringe by the inclusion of a firing mechanism sub-assembly for automatically delivering the substance into the patient's body by injection when the firing mechanism sub-assembly is engaged. In an exemplary embodiment, the automatic injection device may be wearable on the patient's body.

The automatic injection device, e.g., autoinjector pen, of exemplary embodiments may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the patient, and the ability of the antibody, antibody portion, or other TNFα inhibitor to elicit a desired response in the patient. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in patients prior to or at an earlier stage of disease, the prophylactically effective amount will be less than the therapeutically effective amount.

The term "substance" refers to any type of drug, biologically active agent, biological substance, chemical substance or biochemical substance that is capable of being administered in a therapeutically effective amount to a patient employing exemplary automatic injection devices. Exemplary substances include, but are not limited to, agents in a liquid state. Such agents may include, but are not limited to, adalimumab (HUMIRA®) and proteins that are in a liquid solution, e.g., fusion proteins and enzymes. Examples of proteins in solution include, but are not limited to, Pulmozyme (Dornase alfa), Regranex (Becaplermin), Activase (Alteplase), Aldurazyme (Laronidase), Amevive (Alefacept), Aranesp (Darbepoetin alfa), Becaplermin Concentrate, Betaseron (Interferon beta-1b), BOTOX (Botulinum Toxin Type A), Elitek (Rasburicase), Elspar (Asparaginase), Epogen (Epoetin alfa), Enbrel (Etanercept), Fabrazyme (Agalsidase beta), Infergen (Interferon alfacon-1), Intron A (Interferon alfa-2a), Kineret (Anakinra), MYOBLOC (Botulinum Toxin Type B), Neulasta (Pegfilgrastim), Neumega (Oprelvekin), Neupogen (Filgrastim), Ontak (Denileukin diftitox), PEGASYS (Peginterferon alfa-2a), Proleukin (Aldesleukin), Pulmozyme (Dornase alfa), Rebif (Interferon beta-1a), Regranex (Becaplermin), Retavase (Reteplase), Roferon-A (Interferon alfa-2), TNKase (Tenecteplase), and Xigris (Drotrecogin alfa), Arcalyst (Rilonacept), NPlate (Romiplostim), Mircera (methoxypolyethylene glycol-epoetin beta), Cinryze (C1 esterase inhibitor), Elaprase (idursulfase), Myozyme (alglucosidase alfa), Orencia (abatacept), Naglazyme (galsulfase), Kepivance (palifermin) and Actimmune (interferon gamma-1b).

A protein in solution may also be an immunoglobulin or antigen-binding fragment thereof, such as an antibody or antigen-binding portion thereof. Examples of antibodies that may be used in an exemplary automatic injection device include, but are not limited to, chimeric antibodies, non-human antibodies, human antibodies, humanized antibodies, and domain antibodies (dAbs). In an exemplary embodiment, the immunoglobulin or antigen-binding fragment thereof, is an anti-TNFα and/or an anti-IL-12 antibody (e.g., it may be a dual variable domain immunoglobulin (DVD) IgTM). Other examples of immunoglobulins or antigen-binding fragments thereof that may be used in the methods and compositions of exemplary embodiments include, but are not limited to, 1D4.7 (anti-IL-12/IL-23 antibody; Abbott Laboratories); 2.5(E)mg1 (anti-IL-18; Abbott Laboratories); 13C5.5 (anti-IL-13 antibody; Abbott Laboratories); J695 (anti-IL-12; Abbott Laboratories); Afelimomab (Fab 2 anti-TNF; Abbott Laboratories); HUMIRA (adalimumab) Abbott Laboratories); Campath (Alemtuzumab); CEA-Scan Arcitumomab (fab fragment); Erbitux (Cetuximab); Herceptin (Trastuzumab); Myoscint (Imciromab Pentetate); ProstaScint (Capromab Pendetide); Remicade (Infliximab); ReoPro (Abciximab); Rituxan (Rituximab); Simulect (Basiliximab); Synagis (Palivizumab); Verluma (Nofetumomab); Xolair (Omalizumab); Zenapax (Daclizumab); Zevalin (Ibritumomab Tiuxetan); Orthoclone OKT3 (Muromonab-CD3); Panorex (Edrecolomab); Mylotarg (Gemtuzumab ozogamicin); golimumab (Centocor); Cimzia (Certolizumab pegol); Soliris (Eculizumab); CNTO 1275 (ustekinumab); Vectibix (panitumumab); Bexxar (tositumomab and I131 tositumomab); and Avastin (bevacizumab).

Additional examples of immunoglobulins, or antigen-binding fragments thereof, that may be used in the methods and compositions of exemplary embodiments include, but are not limited to, proteins comprising one or more of the following: the D2E7 light chain variable region (SEQ ID NO: 1), the D2E7 heavy chain variable region (SEQ ID NO: 2), the D2E7 light chain variable region CDR3 (SEQ ID NO: 3), the D2E7 heavy chain variable region CDR3 (SEQ ID NO:4), the D2E& light chain variable region CDR2 (SEQ ID NO: 5), the D2E7 heavy chain variable region CDR2 (SEQ ID NO: 6), the D2E7 light chain variable region CDR1 (SEQ ID NO: 7), the D2E7 heavy chain variable region CDR1 (SEQ ID NO: 8), the 2SD4 light chain variable region (SEQ ID NO: 9), the 2SD4 heavy chain variable region (SEQ ID NO: 10), the 2SD4 light chain variable CDR3 (SEQ ID NO: 11), the EP B12 light chain variable CDR3 (SEQ ID NO: 12), the VL10E4 light chain variable CDR3 (SEQ ID NO: 13), the VL100A9 light chain variable CDR3 (SEQ ID NO: 14), the VLL100D2 light chain variable CDR3 (SEQ ID NO: 15), the VLL0F4 light chain variable CDR3 (SEQ ID NO: 16), the LOE5 light chain variable CDR3 (SEQ ID NO: 17), the VLLOG7 light chain variable CDR3 (SEQ ID NO: 18), the VLLOG9 light chain variable CDR3 (SEQ ID NO: 19), the VLLOH1 light chain variable CDR3 (SEQ ID NO: 20), the VLLOH10 light chain variable CDR3 (SEQ ID NO: 21), the VL1B7 light chain variable CDR3 (SEQ ID NO: 22), the VL1C1 light chain variable CDR3 (SEQ ID NO: 23), the VL0.1F4 light chain variable CDR3 (SEQ ID NO: 24), the VL0.1H8 light chain variable CDR3 (SEQ ID NO: 25), the LOE7.A light chain variable CDR3 (SEQ ID NO: 26), the 2SD4 heavy chain variable region CDR (SEQ ID NO: 27), the VH1B11 heavy chain variable region CDR (SEQ ID NO: 28), the VH1D8 heavy chain variable region CDR (SEQ ID NO: 29), the VH1A11 heavy chain variable region CDR (SEQ ID NO: 30), the VH1B12 heavy chain variable region CDR (SEQ ID NO: 31), the VH1E4 heavy chain variable region CDR (SEQ ID NO: 32), the VH1F6 heavy chain variable region CDR (SEQ ID NO: 33), the 3C-H2 heavy chain variable region CDR (SEQ ID NO: 34), and the VH1-D2.N heavy chain variable region CDR (SEQ ID NO: 35).

The term "human TNFα" (abbreviated herein as hTNFα, or simply hTNF) refers to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) Nature 312:724-729; Davis, J. M., et al. (1987) Biochem. 26:1322-1326; and Jones, E. Y., et al. (1989) Nature 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" refers to an agent that interferes with TNFα activity. The term also includes each of the anti-TNFα human antibodies (used interchangeably herein with TNFα antibodies) and antibody portions described herein as well as those described in U.S. Pat. Nos. 6,090, 382; 6,258,562; 6,509,015; 7,223,394; and 6,509,015. In one embodiment, the TNFα inhibitor used in the invention is an anti-TNFα antibody, or a fragment thereof, including infliximab (Remicade®, Johnson and Johnson; described in U.S. Pat. No. 5,656,272); CDP571 (a humanized monoclonal anti-TNF-alpha IgG4 antibody); CDP 870 (a humanized monoclonal anti-TNF-alpha antibody fragment); an anti-TNF dAb (Peptech); CNTO 148 (golimumab; Centocor, See WO 02/12502 and U.S. Pat. No. 7,521,206 and U.S. Pat. No.

7,250,165); and adalimumab (HUMIRA® Abbott Laboratories, a human anti-TNF mAb, described in U.S. Pat. No. 6,090,382 as D2E7). Additional TNF antibodies that may be used in the invention are described in U.S. Pat. Nos. 6,593,458; 6,498,237; 6,451,983; and 6,448,380. In another embodiment, the TNFα inhibitor is a TNF fusion protein, e.g., etanercept (Enbrel®, Amgen; described in WO 91/03553 and WO 09/406476). In another embodiment, the TNFα inhibitor is a recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

The term "treatment" refers to therapeutic treatment, as well as prophylactic or suppressive measures, for the treatment of a disorder, such as a disorder in which TNFα is detrimental, e.g., rheumatoid arthritis.

The term "patient" or "user" refers to any type of animal, human or non-human, that may be injected a substance using exemplary automatic injection devices.

The terms "pre-filled syringe/device" and "pre-fillable syringe/device" encompass a syringe/device that is filled with a substance immediately prior to administration of the substance to a patient and a syringe/device that is filled with a substance and stored in this pre-filled form for a period of time before administration of the substance to a patient.

The term "plunger" refers to a structural member in an automatic injection device for selectively moving and actuating a syringe to inject a dose contained in the syringe into a patient's body.

The term "firing mechanism" refers to a mechanism that, when engaged by a firing engagement mechanism, automatically delivers a substance contained in an automatic injection device into a patient's body. A firing engagement mechanism may be any type of mechanism that engages and triggers the firing mechanism including, but not limited to, a firing button that may be pushed by a patient to trigger the firing mechanism. In an exemplary embodiment, the firing mechanism may be engaged once to automatically deliver one dose of a substance contained in an automatic injection device. In another exemplary embodiment, the firing mechanism may be engaged more than once to automatically deliver more than one dose of a substance, e.g., insulin, contained in an automatic injection device. In this exemplary embodiment, the automatic injection device may be re-filled with the substance between doses.

The term "syringe housing assembly" refers to a collection of components in an automatic injection device that are cooperatively configured to house a syringe, facilitate actuation of the syringe to perform an injection, hold a lockout shroud in a retracted position during an injection, and automatically deploy the shroud to an extended position during or after an injection.

The term "syringe carrier" refers to a structural member in an automatic injection device that envelopes a portion of a syringe used in the device. In an exemplary embodiment, the syringe carrier may be configured to hold and guide the syringe within the housing of the device in order to move the syringe forward to an injecting position.

The term "shroud" or "lockout shroud" refers to a protective covering for a needle that, when deployed, covers the needle and prevents accidental needle stick injury that may be caused by an exposed needle.

The term "retracted position" relating to a shroud refers to a position of the shroud relative to the syringe that allows the needle to extend through a proximal opening of the shroud. In an exemplary embodiment, the retracted position of the shroud may be achieved by using a force from a biasing member to push the shroud distally relative to the housing or relative to the syringe.

The term "extended position" or "deployed position" relating to a shroud refers to a position of the shroud relative to the syringe that allows the shroud to protectively cover the needle and prevents the needle from extending through a proximal opening of the shroud. In an exemplary embodiment, the extended position of the shroud may be achieved by using the force exerted by a biasing mechanism to push the shroud in the proximal direction relative to the housing or relative to the syringe.

The term "shroud deployment mechanism" refers to a mechanism that includes and automatically deploys a shroud to protectively cover a needle. In exemplary embodiments, the shroud may be deployed during and/or after an injection is delivered using the device. In an exemplary embodiment, the shroud deployment mechanism may hold the shroud in a retracted position during use of the needle in an injection, and may automatically deploy the shroud to an extended position to cover the needle during and/or after the needle is removed from the injection site. An exemplary shroud deployment mechanism may include a shroud, a biasing mechanism and part of a housing, all cooperatively engaged to hold the shroud retracted in the retracted position during a first time period (for example, during an injection) and to deploy the shroud to the extended position during a second time period (for example, during and/or after an injection).

The term "shroud deployment failure" or "failure in shroud deployment" refers to a problematic deployment of a shroud of an automatic injection device that provides a protective covering over a needle. Shroud deployment failure may include, but is not limited to, non-deployment of the shroud, partial deployment of the shroud, complete or partial deployment of the shroud after an unacceptably long delay, and the like. In an exemplary embodiment, an acceptable delay may range from about zero to about two seconds. In this exemplary embodiment, shroud deployment with a delay greater than about two seconds may constitute a shroud deployment failure.

The term "extension force" refers to the force with which an exemplary shroud of an automatic injection device is deployed from a retracted position to an extended position.

The term "retraction force" refers to the force with which an exemplary shroud of an automatic injection device is moved from an extended position to a retracted position.

The term "residual extension force" refers to the forces experienced at or near the end of the shroud deployment process when the shroud is at or is approaching its fully extended position.

The term "override force" refers to the maximum force that an exemplary shroud, once deployed to an extended position, can reliably resist or withstand without retracting back toward a retracted position and exposing the needle. Exemplary shroud override forces may include, but are not limited to, about 80 N to about 120 N. In an exemplary embodiment, the needle may be about 7.4 mm from the proximal end of the extended shroud before an override force is applied to the shroud. In an exemplary embodiment, the maximum override force may be reached before the shroud travels about 2-3 mm in the distal direction from its extended position.

The term "distal" refers to a portion, end or component of an exemplary automatic injection device that is farthest from an injection site on the patient's body when the device is held against the patient for an injection or for mimicking an injection.

The term "proximal" refers to a portion, end or component of an exemplary automatic injection device that is closest to an injection site on a patient's body when the device is held against the patient for an injection or for mimicking an injection.

II. EXEMPLARY AUTOMATIC INJECTION DEVICES

Exemplary embodiments are described below with reference to certain illustrative embodiments. While exemplary embodiments are described with respect to using an automatic injection device to provide an injection of a dose of a liquid medication, one of ordinary skill in the art will recognize that exemplary embodiments are not limited to the illustrative embodiments and that exemplary automatic injection devices may be used to inject any suitable substance into a patient. In addition, components of exemplary automatic injection devices and methods of making and using exemplary automatic injection devices are not limited to the illustrative embodiments described below.

A syringe of an exemplary automatic injections device may contain a dose of a TNFα inhibitor. In an exemplary embodiment, the TNFα inhibitor may be a human TNFα antibody or antigen-biding portion thereof. In an exemplary embodiment, the human TNFα antibody or antigen-binding portion thereof may be adalimumab or golimumab.

FIGS. 1 and 2 illustrate an exemplary automatic injection device 10 suitable for injecting a dose of a substance, such as a liquid drug, into a patient. FIG. 1 illustrates a perspective view of the exemplary automatic injection device 10 in which caps that cover proximal and distal ends of the housing are removed. FIG. 2 illustrates a perspective view of the exemplary automatic injection device 10 of FIG. 1 in which the proximal and distal ends of the housing are capped using proximal and distal caps.

Referring to FIG. 1, the automatic injection device 10 includes a housing 12 for housing a container, such as a syringe, containing a dose of a substance to be injected into a patient's body. The housing 12 has a tubular configuration, although one of ordinary skill in the art will recognize that the housing 12 may have any size, shape and configuration capable of housing a syringe or other container. While exemplary embodiments will be described with respect to a syringe mounted in the housing 12, one of ordinary skill in the art will recognize that the automatic injection device 10 may employ any other suitable container for storing and dispensing a substance, for example, a cartridge.

The exemplary syringe is preferably slidably mounted in the housing 12, as described in detail below. When the device 10 is in an inactivated position, the syringe is sheathed and retracted within the housing 12. When the device 10 is actuated, a needle coupled to a proximal end of the syringe projects from a proximal end 20 of the housing 12 to allow ejection of the substance from the syringe into the patient's body. As shown, the proximal end 20 of the housing 12 includes an opening 28 through which the needle of the syringe projects when the device 10 is actuated. In an exemplary embodiment, the opening 28 may be located in the housing 12 itself. In another exemplary embodiment, the opening 28 may be located in another internal component, e.g., a shroud used to cover the needle. In another exemplary embodiment, the opening 28 may be located in the housing 12 and another internal component, e.g., a shroud.

Referring still to FIG. 1, a distal end 30 of the housing 12 includes a firing engagement mechanism, e.g., a firing button 32, configured to actuate a firing mechanism. The housing 12 also houses the firing mechanism, e.g., one or more actuators, configured to drive the syringe from a sheathed or retracted position within the housing 12 (in which the needle does not project from the housing 12) to a projecting position (in which the needle projects from the housing 12). The firing mechanism is configured to subsequently expel the substance from the syringe through the needle into the patient's body.

The exemplary automatic injection device 10 may include a removable proximal cap 24 (or needle cap) for covering the proximal end 20 of the housing 12 to prevent exposure of the needle prior to an injection. In the illustrative embodiment, the proximal cap 24 may include a boss 26 for locking and/or joining the proximal cap 24 to the housing 12 until the patient is ready to activate the device 10. Alternatively, the proximal cap 24 may include a threaded screw portion, and the internal surface of the housing 12 at opening 28 may include a screw thread. Any suitable mating mechanism may be used in accordance with the teachings of exemplary embodiments.

The exemplary automatic injection device 10 may include a removable distal cap 34 configured to cover the firing button 32 to prevent exposure and accidental engagement of the firing button 32 prior to an injection. A step 29 may be formed at the distal end of the housing 12 to accommodate the distal cap 34. In an exemplary embodiment, the distal cap 34 may be coupled to the firing button 32 in a snap-fit. In another exemplary embodiment, the distal cap 34 may include a boss for locking and/or joining the distal cap 34 to the firing button 32 of the device 10 until the patient is ready to activate the device 10. In another exemplary embodiment, the distal cap 34 may include a threaded screw portion, and a surface of the firing button 32 may include a screw thread. Any suitable mating mechanism may be used in accordance with the teachings of exemplary embodiments.

The housing 12 and caps 24, 34 may include graphics, symbols and/or numbers to facilitate use of the automatic injection device 10. For example, the housing 12 may include an arrow 125 on an outer surface pointing towards the proximal end 20 of the device 10 to indicate how the device 10 should be held relative to the patient (i.e., with the proximal end 20 placed on the injection site). In addition, the proximal cap 24 is labeled with a "1" to indicate that a patient should remove the proximal cap 24 of the device first, and the distal cap is labeled with a "2" to indicate that the distal cap 34 should be removed after the proximal cap 24 is removed in preparation for an injection. One of ordinary skill in the art will recognize that the automatic injection device 10 may have any suitable graphics, symbols and/or numbers to facilitate patient instruction, or the automatic injection device 10 may omit such graphics, symbols and/or numbers.

The housing 12 may also preferably include a display window 130 to allow a patient to view the contents of the syringe housed within the housing 12. The window 130 may include an opening in the sidewall of the housing 12, or may include a translucent material in the housing 12 to allow viewing of the interior of the device 10. The housing 12 may be formed of any suitable biocompatible or surgical material including, but not limited to, plastics and other known materials.

Figure 4:
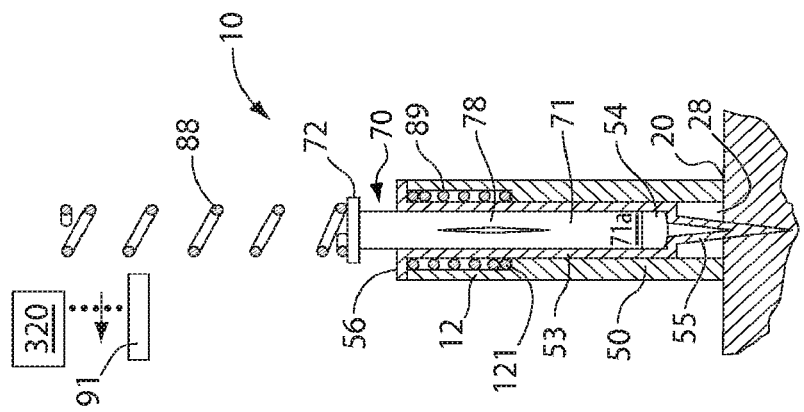
FIG. 4 (prior art) illustrates a cross-sectional schematic view of the exemplary automatic injection device of FIG. 3 during a subsequent stage of operation.
Figure 3:
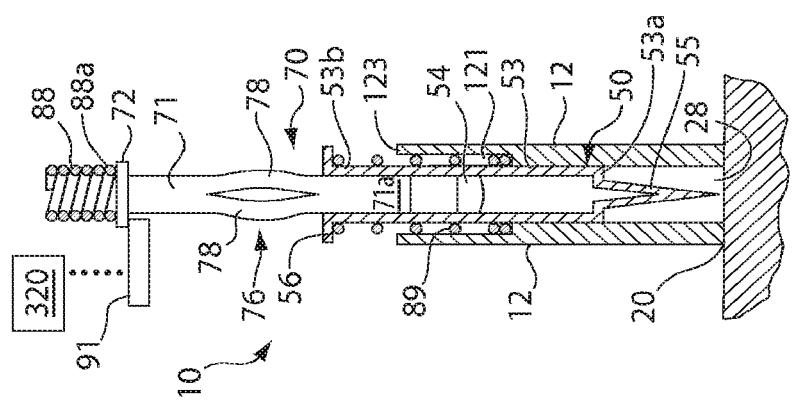
FIG. 3 (prior art) illustrates a cross-sectional schematic view of an exemplary automatic injection device before use.

FIGS. 3 and 4 (prior art) are cross-sectional schematic views of the components of an exemplary automatic injection device 10. FIG. 3 (prior art) illustrates a cross-sectional schematic view of the exemplary automatic injection device 10 prior to use. FIG. 4 (prior art) illustrates a cross-sectional schematic view of the exemplary automatic injection device 10 of FIG. 3 during a post-injection stage of operation.

As illustrated in FIGS. 3 and 4, a syringe 50 or other suitable container for a substance is disposed within the interior of the housing 12 of the device 10. An exemplary syringe 50 may include a hollow barrel portion 53 for holding a dose of a liquid substance to be injected into a patient's body. An exemplary barrel portion 53 is substantially cylindrical in shape, although one of ordinary skill in the art will recognize that the barrel portion 53 may have any suitable shape or configuration. A seal, illustrated as a bung 54, seals the dose within the barrel portion 53. The syringe 50 may also include a hollow needle 55 connected to and in fluid communication with the barrel portion 53, through which the dose can be ejected by applying pressure to the bung 54. The hollow needle 55 extends from a proximal end 53a of the barrel portion 53. A distal end 53b of the barrel portion 53 includes a flange 56, or other suitable mechanism, for abutting a stop 123 in the housing 12 to limit the movement of the syringe 50 within the housing 12, as described below. One of ordinary skill in the art will recognize that exemplary embodiments are not limited to the illustrative syringe 50 and that any suitable container for containing a dose of a substance to be injected may be used in accordance with the teachings of exemplary embodiments.

Any suitable needle 55 may be used in an exemplary automatic injection device. In an exemplary embodiment, the needle 55 may be a fixed twenty-seven gauge one-half inch needle. In another exemplary embodiment, the needle 55 may be a twenty-nine gauge one-half inch needle. The tip of an exemplary hollow needle 55 may include a number of bevels, e.g., five bevels, to facilitate insertion. However, the needle 55 may have any suitable size, shape and configuration suitable for piercing a patient's skin to deliver a substance to the patient's body, and is not limited to the illustrative embodiment. Suitable types of needles are well-known in the art.

The automatic injection device 10 shown in FIGS. 3 and 4 may include a syringe actuation component 70, illustrated as a plunger, for selectively injecting the dose contained in the syringe 50 into a patient's body. The exemplary plunger 70 may include a rod portion 71 having a first end 71a connected to the bung 54 for selectively applying pressure to the bung 54 to expel the dose through the needle 55. The plunger 70 may include a flanged second end 72. In an exemplary embodiment, the plunger 70 may include more or fewer components than those illustrated in FIGS. 3 and 4. In an exemplary embodiment, the device 10 may include more or fewer actuators than those illustrated in FIGS. 3 and 4.

The plunger 70 may be biased forward towards the proximal end 20 of the device 10 by a first biasing mechanism, illustrated as a coil spring 88, disposed about or above the flanged second end 72 of the plunger 70. A proximal end 88a of the coiled spring 88 may abut the flanged second end 72 of the plunger 70 to selectively apply pressure to the plunger 70 and to move the plunger 70 toward the injection site on the patient's body. Alternatively, the plunger 70 may extend through the center of the spring 88.

As illustrated in FIG. 3, prior to use of the device 10, the coil spring 88 (or another suitable mechanism) may be compressed between the plunger 70 and a component or internal surface of the device, thus storing energy. A trigger 91, which may be activated by any suitable actuation means such as an activation mechanism 320, may retain the plunger 70 and the first biasing mechanism 88 in a retracted, latched position before the activation mechanism 320 is activated. The trigger 91 may latch the flanged second end 72 of the plunger 70. When the activation mechanism 320 or other actuation means is activated, the trigger 91 may release the flanged second end 72 of the plunger 70, allowing the coil spring 88 to propel the plunger 70 towards the first end of the device 10.

A second biasing mechanism, illustrated as an exemplary coil spring 89, may hold the syringe 50 in a retracted position within the housing 12 prior to use, as shown in FIG. 3. In the retracted position, the needle 55 may be preferably sheathed entirely within the housing 12. The exemplary syringe coil spring 89 may be disposed about the distal portion of the barrel portion 53 and may be seated in a shelf 121 formed within the housing 12. The distal end of the coil spring 89 may abut the flanged distal end 56 of the syringe 50. The spring force of the second biasing mechanism 89 may push the flanged distal end 56 of the syringe 50 away from the proximal end 20 of the housing 12, thereby holding the syringe 50 in the retracted position until activated. Other components of the device 10 may also be used to position the syringe 50 relative to the housing 12.

The first biasing mechanism 88 and the second biasing mechanism 89 may have any suitable configuration and tension suitable for use in biasing certain components of the device. For example, the first biasing mechanism 88 may have any suitable size, shape, energy and properties suitable for driving the plunger 70 and the syringe 50 forward when released or actuated. The second biasing mechanism 89 may have any suitable size, shape, energy and properties suitable for retracting the syringe 50 prior to actuation of the first biasing mechanism 88. Other suitable means for facilitating movement of the plunger 70 and/or syringe 50 may also be used. Other suitable means of latching spring 88 may also be used.

Referring still to the illustrative embodiment of FIGS. 3 and 4, the plunger 70 may include a rod portion 71 and an exemplary radially compressible expanded portion 76 at the center of the plunger 70 between proximal and distal solid portions of the rod portion 71. In an exemplary embodiment, the expanded portion 76 may be aligned along the central axis of the rod portion 71. In an illustrative embodiment, the rod 71 may be split and expanded to form a pair of projecting elbows 78 that encircle a longitudinal slit or void and that define the radially compressible expanded portion 76. The projecting elbows 78 may be pre-formed as part of the molded plunger 70 or, alternatively, may be attached to the plunger 70 separately. The projecting elbows 78 may be compressible so that they can be moved radially inwardly to cause that portion of the rod 71 to adopt a diameter similar to the rest of the rod 71. The compressible expanded portion 76 facilitates movement of the syringe 50.

When an activation mechanism 320 activates the trigger 91 to release the plunger 70, the spring force of the coil spring 88 propels the plunger 70 forward. The activation mechanism 320 may have any suitable size, shape, configuration and location suitable for releasing the plunger 70 or otherwise activating the device 10. For example, the activation mechanism 320 may include a firing button formed at a distal end 30 of the housing 12, and/or may include another suitable device, such as a latch, twist-activated switch and other devices known in the art. While the illustrative activation mechanism 320 is located towards a distal end 30 of the device 10, one of ordinary skill in the art will recognize that the activation mechanism 320 may be positioned at any suitable location on the device 10.

During a first operational stage, the plunger 70 pushes the syringe 50 forward such that the tip of the needle 55 projects from the proximal end 20 of the housing 12. The initial biasing force provided by the first coil spring 88 is sufficient to overcome the biasing force of the second coil spring 89 to allow movement of the syringe 50 against the backward biasing force of the second coil spring 89. In the first operational stage, the expanded region 76 of the plunger 70, formed by the projecting elbows 78 of the plunger 70, may rest against the flanged distal end 56 of the syringe 50, or may initially partially enter the barrel portion 53 and, in turn, at least temporarily halt due to stiction forces. This prevents the plunger 70 from traveling within the syringe barrel portion 53. In this manner, by stiction or abutment of the flanged distal end 56, all biasing force from the first coil spring 88 is applied to move the syringe 50 forward towards the proximal end 20 of the device 10.

The forward motion of the syringe 50 towards the proximal end 20 of the device 10 may continue against the biasing force of the coil spring 89 until the flanged distal end 56 of the barrel portion 53 abuts the stop 123 in the housing 12, thereby forming a stopping mechanism 56, 123. One of ordinary skill in the art will recognize that other stopping mechanisms may be employed and that exemplary embodiments are not limited to the illustrative stopping mechanism.

The first operational stage may propel the tip of the needle 55 through the opening 28 at the proximal end 20 of the device 10, so that the needle 55 may pierce the patient's skin. During this stage, the syringe barrel portion 53 may preferably remain sealed without expelling the substance through the needle 55. The interference caused by the stopping mechanism 56, 123 may maintain the needle 55 in a selected position extending from the proximal open end 28 of the device 10 during subsequent steps. Until the stopping mechanism 56, 123 stops the movement of the syringe 50, the compressible expanded portion 76 of the plunger 70 may prevent movement of the plunger 70 relative to the barrel portion 53. The stopping mechanism 56, 123 may be positioned at any suitable location relative to the open proximal end 20 to allow the syringe 50 to penetrate the skin by any suitable depth suitable for an injection.

Figure 5:
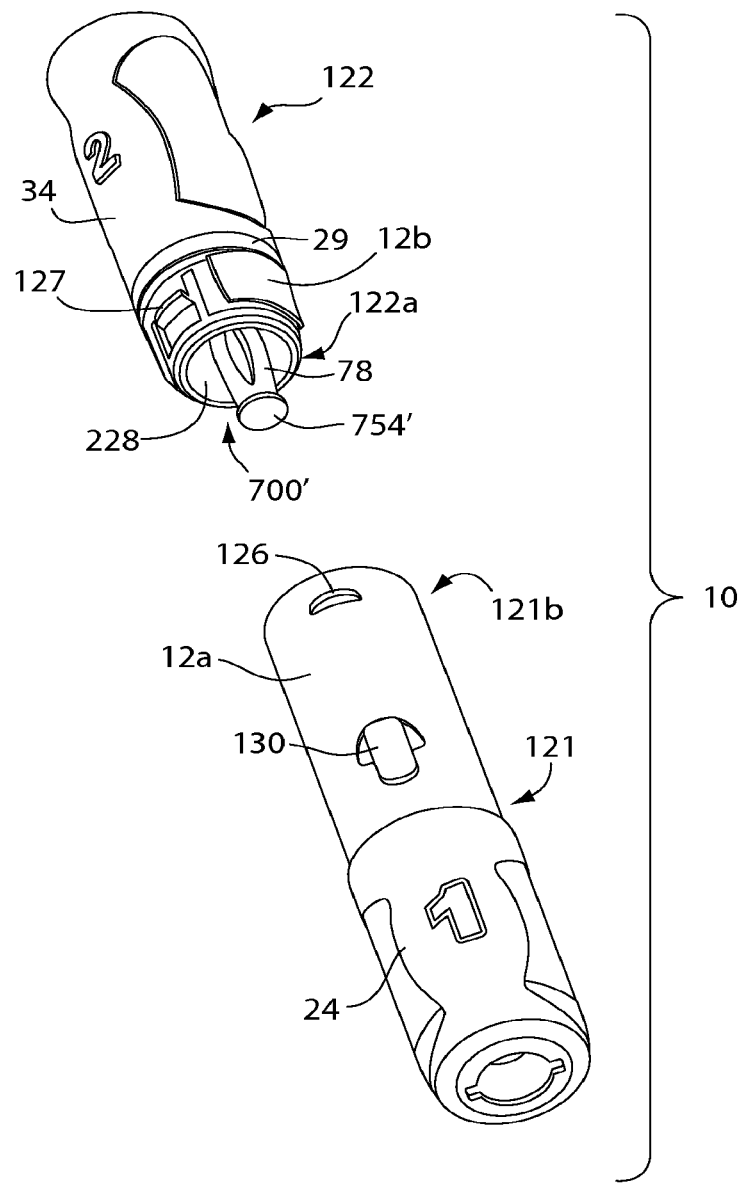
FIG. 5 illustrates a perspective view of an exemplary automatic injection device including a syringe housing sub-assembly and a firing mechanism sub-assembly.

The second operational stage commences after the stop 123 of the housing 12 catches the flanged portion 56, stopping farther movement of the barrel portion 53. During this stage, the continued biasing force of the coil spring 88 may continue to push the plunger 70 relative to the housing 12, as shown in FIG. 5. The biasing force may cause the elbows 78 of the plunger 70 to compress radially inward and slide into the interior of the barrel portion 53. While the interference between components 123 and 56 may retain the barrel portion 53 in a selected position (with the needle 55 exposed) and with the elbows 78 in a collapsed stage, the coil spring 88 may push the plunger 70 within the barrel portion 53. After the plunger 70 overcomes the necessary force to allow the elbows 78 to compress and extend into the barrel portion 53, the plunger 70 may apply pressure to the bung 54, causing ejection of the substance contained in the syringe 50 through the projecting needle 55. Because the needle 55 was made to penetrate the patient's skin in the first operational stage, the substance contained in the barrel portion 53 of the syringe 50 is injected directly into a portion of the patient's body.

FIG. 5 illustrates a perspective view of an exemplary automatic injection device 10 including an exemplary syringe housing sub-assembly 121 and an exemplary firing mechanism sub-assembly 122. In an exemplary embodiment, the automatic injection device 10 may include two interlocking components: a syringe housing sub-assembly 121 containing the proximal components of the device 10 (e.g., proximal housing component 12a, syringe barrel 53, coil spring 89, needle 55 and other proximal components, etc.), and a firing mechanism sub-assembly 122 containing the distal components of the device 10 (e.g., firing body 12b, syringe actuation component 700' having a pressurizer 754' extending out of an opening 228 at the proximal end 122a of the firing mechanism sub-assembly 122, etc.). The syringe housing sub-assembly 121 and the firing mechanism sub-assembly 122 may be coupled through any suitable means. In an exemplary embodiment, a proximal end 122a of the firing mechanism sub-assembly 122 may be sized and configured to be inserted into a distal end 121b of the syringe housing sub-assembly 121. In addition, one or more tabs 127 at the proximal end 122a of the firing mechanism sub-assembly 122 may snap-fit into corresponding openings 126 at the distal end 121b of the syringe housing assembly 122 to ensure alignment and coupling of the two assemblies 121, 122 and the components housed therein.

Figure 6:
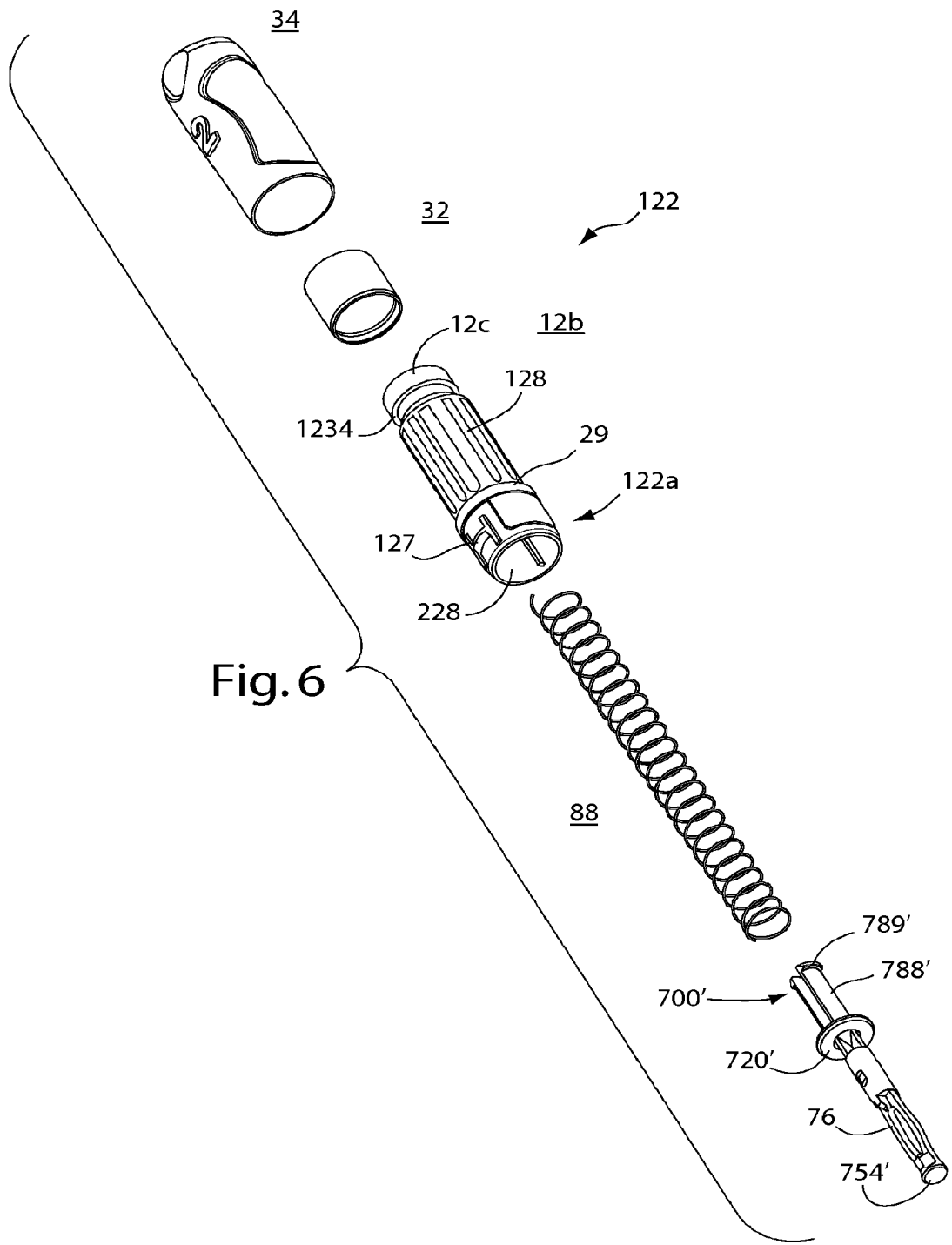
FIG. 6 illustrates an exploded perspective view of the firing mechanism sub-assembly of the exemplary automatic injection device of FIG. 5.
Figure 7:
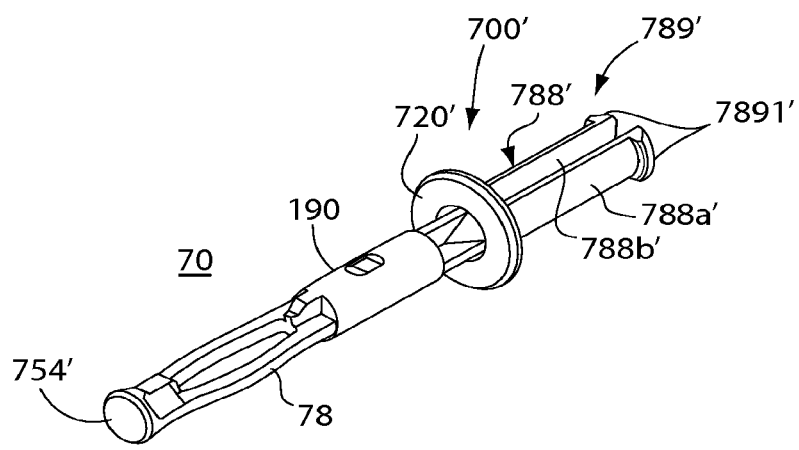
FIG. 7 illustrates a perspective view of a syringe actuation component of the exemplary firing mechanism sub-assembly of FIG. 6.

FIG. 6 illustrates an exploded perspective view of the firing mechanism assembly 122 of the exemplary automatic injection device of FIG. 5. FIG. 7 illustrates a perspective view of an exemplary syringe actuation component 700' included in the firing mechanism assembly 122. The firing mechanism sub-assembly 122 may include the firing body 12b (also called the distal housing component) having a hollow internal bore for housing the biasing mechanism 88 and a distal portion of the syringe actuation component 700'. The firing body 12b may include an opening 228 at the proximal end 122a to allow entry of the biasing mechanism 88 and the syringe actuation component 700' during assembly of the firing mechanism sub-assembly 122. The firing body 12b may have one or more ridges or grooves on its outer surface 128 to identify it and to facilitate gripping of the device 10. The firing body 12b may include one or more tabs 127 at or near the proximal end 122a of the firing mechanism sub-assembly 122 configured to snap-fit into corresponding openings 126 on the distal end 121b of the syringe housing assembly 122. The firing body 12b may also include a narrowed distal wall 1234 for supporting the distal end of the spring 88. The firing body 12b may also include a distal anchoring cap 12c over which the anchoring portion 789' of the syringe actuation component 700' may be supported.

The firing mechanism sub-assembly 122 may also include a syringe actuator, illustrated as a syringe actuation component 700', which extends from the proximal end 122a of the firing body 12b for driving the syringe 50 forward within the housing 12 in a first operational stage, and for actuating the bung 54 to expel the contents of the syringe 50 in a second operational stage. The proximal end of the syringe actuation component 700' may include be configured as a pressurizer 754' for engaging and driving the bung 54. Distal to the pressurizer 754', a pair of elbows 76 may be provided with a central longitudinal slit or void. The elbows 76 may be aligned along a central axis of the syringe actuation component 700' and may extend between the pressurizer 754' and a solid rod portion 70 of the syringe actuation component 700'. The syringe actuation component 700' may include an indicator 190 at the solid rod portion 70 distal to the elbows 78. During operation of the device 10 and after completion of an injection, the indicator 190 is configured to align with the window 130 on the housing 12 to indicate at least partial completion of the injection. The indicator 190 preferably has a distinctive color or design to represent completion of an injection.

The illustrative syringe actuation component 700' further includes a retaining flange 720' for holding the actuating coil spring 88 in a compressed position until actuation. The retaining flange 720' is sized, dimensioned and formed of a material that preferably allows the syringe actuation component 700' to slidably and easily move within the housing 12 when the device 10 is actuated. Extending distally from the retaining flange 720', the syringe actuation component 700' forms a base 788', for the actuating coil spring 88. The base 788' terminates in a trigger anchoring portion 789'. The illustrative base 788' may comprise flexible arms 788a', 788b' around which the spring 88 coils. The trigger anchoring portion 789' may comprise tabbed feet 7891' extending from the base 788' and configured to selectively engage the anchoring cap 12c of the firing body 12b. The firing button 32 coupled to the distal end of the firing body 12b is configured to hold the trigger anchoring portion 789' retracted until activation. When activated, the firing button 32 releases the trigger anchoring portion 789', allowing the coil spring 88 to propel the syringe actuation component 700' towards the proximal end 20 of the device 10.

In a retracted, anchored position shown FIGS. 6 and 7, the trigger anchoring portion 789' interacts with the housing 12, which holds the tabbed feet 7891' in a latched position against the biasing force of the coil spring 88, to maintain the syringe actuation component 700' in a retracted position. In this position, the flange 720' retracts the spring 88 against the distal wall 1234 of the firing body 12b. An opening in the anchoring cap 12c allows the firing button 32 access to the anchoring portion 789' of the syringe actuation component 700'. In the retracted position, the pressurizer 754' of the syringe actuation component 700' extends out of an opening 228 at the proximal end 122a of the firing body 12b.

When the firing body 12b couples to a corresponding syringe actuation mechanism 700', the pressurizer 754' extends into the barrel portion of a syringe housed therein. The pressurizer 754' may be integral with, the same as, connected to, or otherwise in communication with the bung 54 of a syringe 50 housed in the device 10 and may have any suitable size, shape and configuration suitable for applying pressure to the bung 54. In one embodiment, the pressurizer 754' has a cross-section corresponding to the shape of the barrel portion 53 of a corresponding syringe 50 so as to substantially seal the barrel portion 53, and the pressurizer 754' is configured to slidably move within the barrel portion 53 to apply pressure to the bung 54 and actuate the syringe 50.

In the illustrative embodiment of FIGS. 6 and 7, the syringe actuation component 700' constitutes a single, integrated mechanism for anchoring a corresponding syringe 50, spring 88 and other components, actuating and moving the syringe 50 to a protracted position, and separately expelling the contents of the syringe 50.

Figure 8:
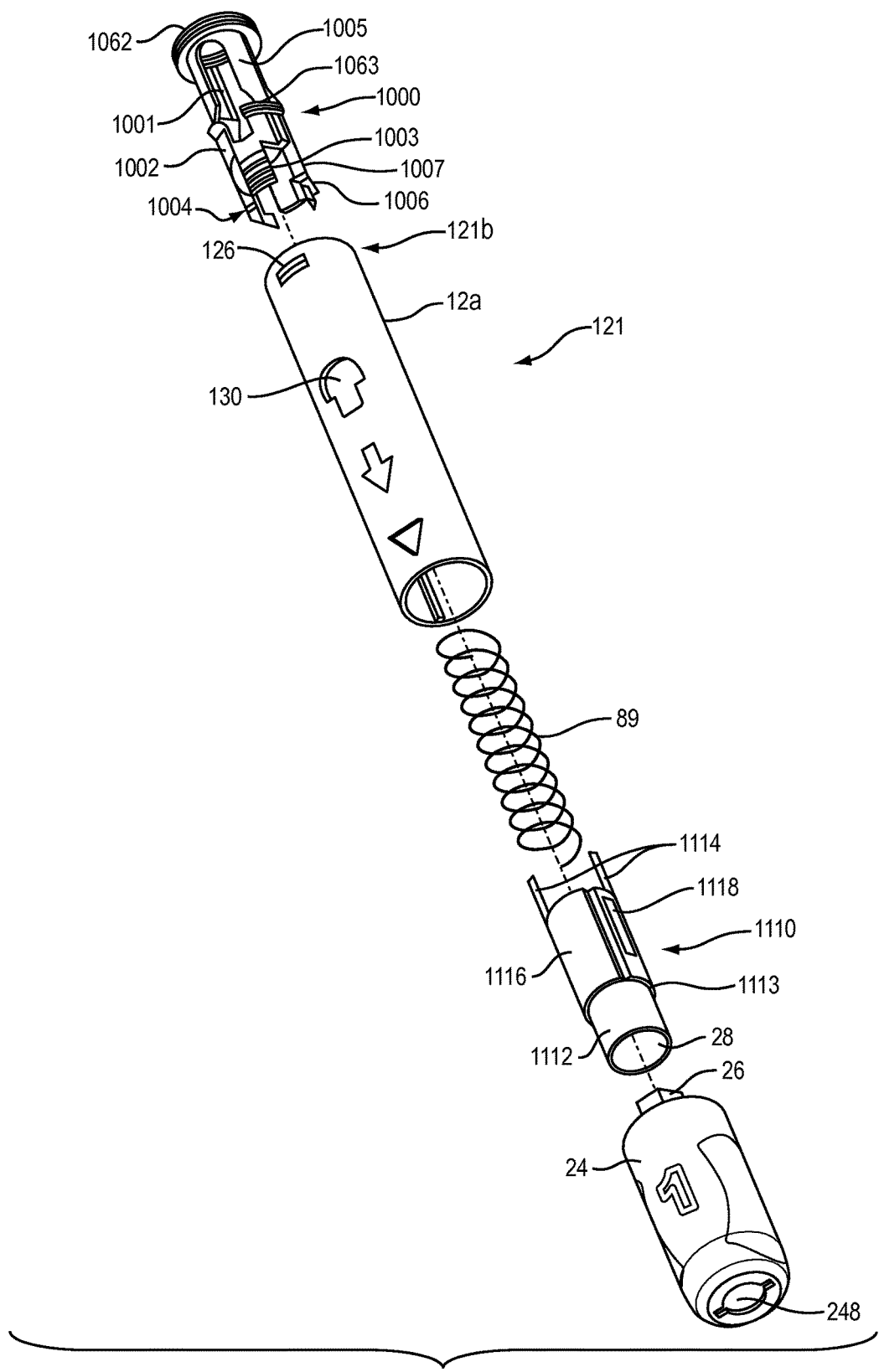
FIG. 8 illustrates an exploded perspective view of the syringe housing sub-assembly of the exemplary automatic injection device of FIG. 5.
Figure 9:
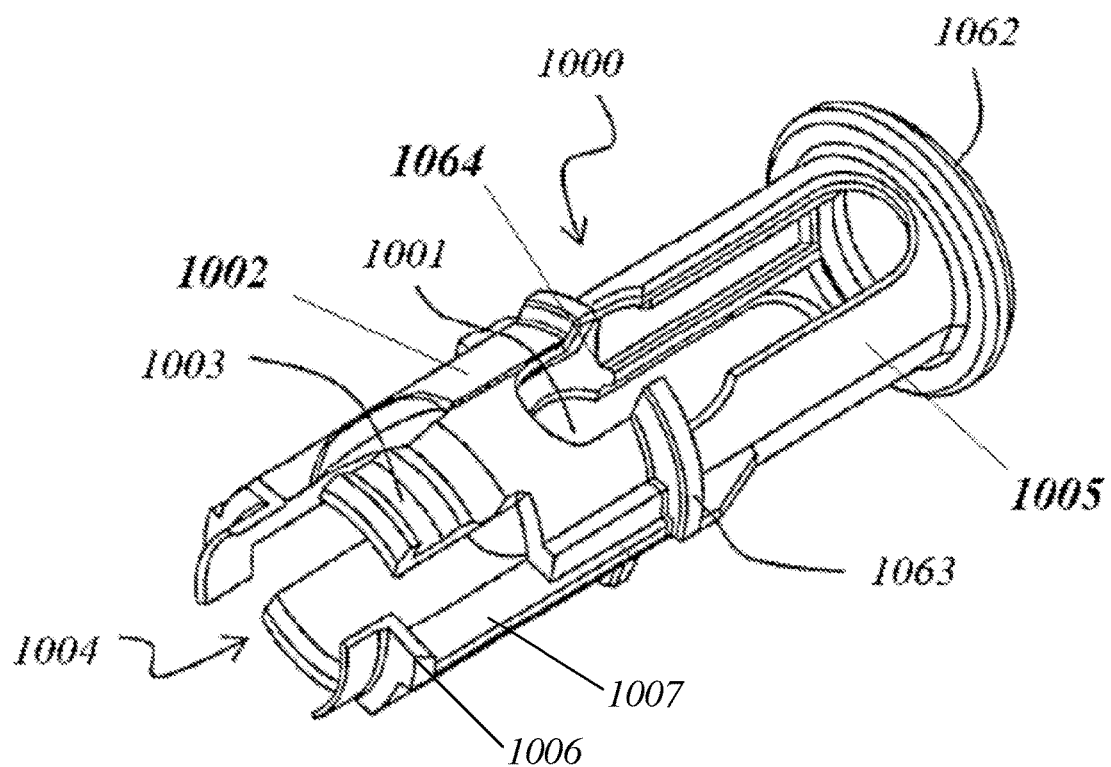
FIG. 9 illustrates a perspective view of a syringe carrier of the exemplary syringe housing sub-assembly of FIG. 8.

FIG. 8 is an exploded perspective view of an exemplary syringe housing sub-assembly 121 configured to be assembled and interact with the firing mechanism sub-assembly 122 of FIG. 7. The components of the syringe housing sub-assembly 121 are cooperatively configured to house a syringe 50 containing a substance to be injected and to facilitate operation of the device 10 in the two different operational stages as described above. The syringe housing sub-assembly 121 includes a syringe carrier 1000 configured to movably hold a syringe. FIG. 9 illustrates a perspective view of an exemplary syringe carrier 1000. The syringe housing sub-assembly 121 also includes a shroud 1110 configured to protectively cover a needle 55 before, during or after use in an injection. The syringe carrier 1000 and the shroud 1110 may be coupled together with a second biasing member 89 positioned therebetween. The syringe carrier 1000, the shroud 1110 and the biasing member 89 may be placed within the hollow bore of a proximal housing component 12a whose proximal end may be covered by the proximal cap 24.

The proximal housing component 12a is a portion of the syringe housing 12 that provides a hollow structural member for accommodating the second biasing mechanism 89, the syringe carrier 1000 and the shroud 1110 of the syringe housing sub-assembly 121. The proximal housing component 12a may be a tubular member having a tubular side wall, i.e., may have a substantially cylindrical shape with a substantially circular cross-section. The proximal housing component 12a may extend from a proximal end to a distal end along the longitudinal axis of the automatic injection device. The proximal housing component 12a may be coupled to the firing body 12b at or near the distal end, and may be coupled to the proximal cap 24 at or near the proximal end. The proximal housing component 12a may include one or more windows 130 formed or provided in its side wall to allow a user to view the contents of the syringe 50 disposed inside the proximal housing component 12a.

The shroud 1110 is a structural member that, when deployed, provides a protective covering for the needle before, during and/or after the use of the needle in an injection. The components of the syringe housing sub-assembly 121 are cooperatively configured to hold the shroud 1110 in a retracted position relative to the proximal housing component 12a during an injection and to automatically deploy the shroud 1110 relative to the proximal housing component 12a during or after an injection. In an exemplary embodiment, the shroud 1110 may be positioned at or may form the proximal end 20 of the housing 12. The shroud 1110 may include a main tubular body portion 1116 having a tubular side wall, i.e., may have a substantially cylindrical shape with a substantially circular cross-section. The main tubular body portion 1116 may extend from a proximal end to a distal end along the longitudinal axis of the automatic injection device.

The main tubular body portion 1116 may include one or more slots 1118 extending longitudinally along the body portion. In an exemplary embodiment, the slot 1118 may provide a longitudinal track for the movement of a raised rail edge or tabbed foot 1006 of the syringe carrier 1000 as the syringe carrier 1000 and/or the shroud 1110 move relative to each other. When the shroud 1110 moves toward the syringe carrier 1000 during retraction of the shroud, the tabbed foot 1006 of the syringe carrier 1000 may travel toward the proximal end of the device along the slot 1118. Conversely, when the shroud 1110 moves away from the syringe carrier 1000 during deployment of the shroud, the tabbed foot 1006 of the syringe carrier 1000 may travel toward the distal end of the device along the slot 1118.

The distal end of the main tubular body portion 1116 may be configured as a rim and may be coupled to one or more distal arms 1114 that are spaced apart from each other. In an exemplary embodiment, two spaced-apart distal arms 1114 are coupled to the distal end of the main tubular body portion 1116. The distal arms 1114 may take any suitable shape including, but not limited to, a substantially cylindrical shape with a circular cross-section, a substantially extended box shape with a rectangular or square cross-section, etc. In an exemplary embodiment, the distal arms 1114 may extend substantially parallel to each other and to the longitudinal axis of the device. In another exemplary embodiment, the distal arms 1114 may extend at an angle to the longitudinal axis of the device such that they diverge from each other relative to attachment points on the shroud 1110.

The proximal end of the main tubular body portion 1116 may be coupled to a proximal tubular portion 1112. In an exemplary embodiment, the proximal tubular portion 1112 may cover part or all of the needle 55 after an injection. In an exemplary embodiment, the main tubular portion 1116 may cover part or all of the needle 55 after an injection. The proximal tubular portion 1112 of the shroud 1110 may be a tubular member having a tubular side wall, i.e., may have a substantially cylindrical shape with a substantially circular cross-section. The proximal tubular portion 1112 may extend from a proximal end to a distal end along the longitudinal axis of the automatic injection device. The proximal end of the proximal tubular portion 1112 may have a proximal opening 28. The proximal opening 28 may allow the needle 55 to project outwardly and to penetrate an injection site during operation of the device 10. The distal end of the proximal tubular portion 1112 may be coupled to or may extend from the proximal end of the main tubular body portion 1116 of the shroud 1110.

In an exemplary embodiment, the proximal tubular portion 1112 of the shroud 1110 may have a cross-sectional diameter smaller than the cross-sectional diameter of the main tubular body portion 1116. In this exemplary embodiment, a stepped portion 1113 may be formed at the coupling between the distal end of the proximal tubular portion 1112 and the proximal end of the main tubular body portion 1116. The stepped portion 1113 may form a forward stop for the biasing member 89 that is disposed at least partly inside the shroud 1110. The stepped portion 1113 may confine the biasing member 89 and prevent farther forward movement of the biasing member 89 towards the proximal end of the device 10.

The syringe carrier 1000 is a structural member that envelopes the distal half of a syringe 50 used in the device 10. The syringe carrier 1000 may be configured to hold and guide the syringe 50 within the housing 12 in order to move the syringe 50 forward to an injecting position. The syringe 50 may rest in the syringe carrier 1000 and both may be contained in the housing 12. During operation of the device 10, the syringe 50 and the syringe carrier 1000 move proximally forward within the housing 12. The flange 256 within the housing 12 stops and limits the movement of the flange 1063 of the carrier 1000, which in turn stops and limits the movement of the syringe 50. One of ordinary skill in the art will recognize that the movement of the carrier 1000 may be stopped using any suitable stopping mechanism.

In an exemplary embodiment, the syringe carrier 1000 is stationary within the proximal housing component 12a and the syringe 50 selectively and controllably slides within and relative to the syringe carrier 1000. The side wall of the proximal tubular portion 1002 of the syringe carrier 1000 may optionally include a step. In another exemplary embodiment, the syringe carrier 1000 is slidably disposed within the proximal housing component 12a and selectively carries the syringe 50 within the housing 12. The syringe carrier 1000 may have any suitable configuration, shape and size suitable for carrying or guiding the syringe 50 within the proximal housing component 12a. The syringe carrier 1000 is also configured to cooperate with the shroud 1110 in order to automatically deploy the shroud 1110 during and/or after an injection.

The syringe carrier 1000 may include a proximal tubular portion 1002 that is substantially tubular and has a tubular side wall, i.e., has a substantially cylindrical shape with a substantially circular cross-section. The side wall of the proximal tubular portion 1002 may optionally include one or more raised structures, e.g., a longitudinally-extending rail 1007. The rail 1007 may include a tabbed foot 1006. When the syringe carrier 1000 is assembled with the shroud 1110, the tabbed foot 1006 may fit within the slot 1118 of the shroud 1110, such that the two components cooperatively form a locking mechanism for the syringe carrier 1000 and the shroud 1110. In the assembled configuration, the tabbed foot 1006 may travel longitudinally within the slot 1118 but is restricted from disengaging from the slot 1118. That is, a forward movement of the tabbed foot 1006 of the carrier 1000 may be stopped by the proximal end of the slot 1118 of the shroud 1100. At the same time, the rail 1007 fits along internal longitudinal grooves provided in the main tubular body portion 1116 of the shroud 1110, and moves longitudinally along the tracks provided by the grooves. In an exemplary embodiment, the grooves may be provided near the distal end of the shroud 1110 and may extend for an exemplary length of about 2 mm.

The proximal end of the proximal tubular portion 1002 may be coupled to or may extend into a proximal anchor portion 1003. In an exemplary embodiment, the proximal tubular portion 1002 may have a larger outer diameter than the proximal anchor portion 1003. The proximal anchor portion 1003 may have an exemplary outer diameter of about 12.60 mm in an exemplary embodiment. The proximal anchor portion 1003 of the syringe carrier 1000 may limit the movement of the syringe 50 in a distal, rearward direction. The proximal anchor portion 1003 may include one or more radial grooves configured to engage the interior stop or flange 256 of the proximal housing component 12a. The engagement of the proximal anchor portion 1003 with the interior flange 256 limits the movement of the syringe 50 in the distal, rearward direction. The proximal anchor portion 1003 may have a continuously extending side wall or may be divided into discontinuous side walls.

In an exemplary embodiment, the proximal end of the proximal anchor portion 1003 may include a syringe carrier coupler 1004 that extends in the proximal direction past the proximal anchor portion 1003 to facilitate coupling of the syringe carrier 1000 with the distal end of the biasing member 89 and the distal end of the shroud 1110. In an exemplary embodiment, the proximal anchor portion 1003 of the syringe carrier 1000 may provide a stopping mechanism for the distal end of the biasing mechanism 89, and may prevent farther movement of the biasing mechanism 89 in the distal direction.

The distal end of the proximal tubular portion 1002 may be coupled to a proximal portion of a distal tubular portion 1005 that is substantially tubular and has a tubular side wall, i.e., has a substantially cylindrical shape with a substantially circular cross-section. The distal end of the distal tubular portion 1005 may be coupled to or may extend to form a flanged distal end 1062 that may serve as a damper for the syringe 50. The flanged distal end 1062 may extend radially from the distal tubular portion 1005, and may have a larger cross-sectional diameter than the distal tubular portion 1005.

The side wall of the distal tubular portion 1005 may include one or more windows 1001 that allow a user to view the contents of the syringe 50 disposed inside the housing 12. In some exemplary embodiments, the windows 1001 may extend into the proximal tubular portion 1002. In other exemplary embodiments, the windows 1001 may be restricted to either the proximal tubular portion 1002 or the distal tubular portion 1005.

In an exemplary embodiment, the cross-sectional diameter of the distal tubular portion 1005 may be smaller than the cross-sectional diameter of the proximal tubular portion 1002. In this embodiment, there may be transition portion 1064 formed at the coupling between the distal end of the proximal tubular portion 1002 and the proximal end of the distal tubular portion 1005. The transition portion 1064 may form a substantially perpendicular surface between the planes of the tubular portions or may form an inclined surface at an angle relative to the planes of the tubular portions. In an exemplary embodiment, the transition portion 1064 may have a larger outer diameter in at least one part of the transition portion, relative to the outer diameters of the proximal tubular portion 1002 and the distal tubular portion 1005.

The region between the proximal 1002 and the distal 1005 tubular portions may include an intermediate flange 1063 that extends radially from the tubular portions. The intermediate flange 1063 may be a radially continuous structure or a radially discontinuous structure, and may have a larger cross-sectional diameter than the tubular portions. The intermediate flange 1063 may be configured to engage with the interior stop or flange 256 of the proximal housing component 12a to limit the movement of the syringe 50 in the proximal, forward direction. In an exemplary embodiment, the flange 1063 may result in an increased outer diameter of the transition portion 1064 relative to the outer diameters of the proximal tubular portion 1002 and the distal tubular portion 1005.

Upon actuation of the syringe carrier 1000 the syringe carrier 1000 moves toward the proximal end of the device until the intermediate flange 1063 of the syringe carrier 1000 abuts against the interior stop or flange 256 of the proximal housing component 12a. This limits farther movement of the syringe carrier 1000 and the syringe 50 in the proximal, forward direction.

In an exemplary embodiment, the shroud 1110 is in a retracted position prior to performing an injection. In another exemplary embodiment, the shroud 1110 is in an extended position prior to performing an injection and is retracted in order to perform the injection. In this embodiment, in order to expose the needle for an injection, the shroud 1110 is retracted in the distal, backward direction against the biasing force of the biasing member 89. When the needle is in use during an injection, the shroud 1110 may be pushed to or held in a retracted position toward the distal end of the device. During retraction, as the shroud 1110 moves relative to the syringe carrier 1000, the tabbed foot 1006 of the rail 1007 of the syringe carrier 1000 moves in a relative manner longitudinally toward the proximal end of the device along the slot 1118 of the shroud 1110. At the same time, the rail 1007 of the syringe carrier 1000 moves in a relative manner longitudinally along the inner grooves in the shroud 1110. The shroud retraction process is complete and further movement of the shroud 1110 is stopped when the tabbed foot 1006 reaches the proximal end of the slot 1118. Since the tabbed foot 1006 is fit into the slot 1118 in a locking manner, the tabbed foot 1006 does not disengage from the slot 1118 and prevents farther backward or distal motion of the shroud 1110.

In the retracted position of the shroud 1110, the distal rim or end of the main tubular body portion 1116 may abut the proximal side of the stop or flange 256 provided on the inner surface of the proximal housing component 12a. In an exemplary embodiment, in the retracted position, the distal arms 1114 may extend in the distal direction beyond the intermediate flange 1063 of the syringe carrier 1000.

In order to cover the needle before, during or after an injection, the shroud 1110 is deployed in the proximal, forward direction from its retracted position to an extended position under the biasing force of the biasing member 89. In the deployed position, the shroud 1110 protectively covers the needle during or after use and prevents accidental needle stick injuries. In an exemplary embodiment, the shroud 1110 may be automatically deployed by the biasing force of the biasing member 89. During deployment, as the shroud 1110 moves relative to the syringe carrier 1000, the tabbed foot 1006 of the rail 1007 of the syringe carrier 1000 moves in a relative manner longitudinally toward the distal end of the device along the slot 1118 of the shroud 1110. At the same time, the rail 1007 of the syringe carrier 1000 moves in a relative manner longitudinally along the inner grooves in the shroud 1110. The shroud deployment process is complete and further movement of the shroud 1110 is stopped when the tabbed foot 1006 reaches the distal end of the slot 1118. Since the tabbed foot 1006 is fit into the slot 1118 in a locking manner, the tabbed foot 1006 does not disengage from the slot 1118 and prevents farther proximal or forward motion of the shroud 1110.

After the shroud 1110 is deployed to the extended position, the distal arms 1114 ensure that the shroud 1110 is not retracted again due to a backward force applied to the shroud in the distal direction. In exemplary embodiments, the distal arms 1114 of exemplary shrouds 1110 may resist shroud retraction against a maximum force known as the "override force." In an exemplary embodiment, during deployment, the shroud 1110 moves within the housing of the device such that the distal end of the distal arms 1114 of the shroud 1110 rest against the interior stop or flange 256 of the housing. The interior stop or flange 256 thus prevents farther distal or backward movement of the shroud 1110 after the shroud has been deployed. This locking mechanism ensures that the needle is protectively covered after the device has been used, and prevents accidental needle stick injuries caused by accidental retraction of the shroud. Exemplary shroud override forces may range from about 80 N to about 200 N, although override forces are not limited to this exemplary range.

As illustrated in FIG. 9, the biasing member 89 extends between the proximal end of the syringe carrier coupler 1004 of the syringe carrier 1000 and the transition portion 1113 of the shroud 1110. In an exemplary embodiment, the biasing member 89 may hold the syringe 50 in a retracted position within the housing 12 prior to use, as shown in FIG. 3. In another exemplary embodiment, the syringe carrier 1000 holding the syringe 50 may be locked to the interior flange 256 in the housing. This interaction may hold the syringe 50 in a retracted position within the housing before. With the aid of the tube 26 of the first cap 24, this interaction is able to lock the syringe carrier 1000 and the syringe 50 in place during shipping, shock, dropping, vibration, and the like. The biasing member 89 may hold the shroud 1110 forward in this exemplary embodiment.

When the shroud 1110 is in the retracted position, the needle 55 may be preferably sheathed entirely within the housing 12. The exemplary syringe coil spring 89 may be disposed about the proximal portion of the barrel portion 53 of the syringe 50 and may be seated in a shelf formed within the housing interior 12. The top end of the coil spring 89 may abut the flanged second end 56 of the syringe 50. The spring force of the second biasing mechanism 89 may push the flanged second end 56 of the syringe 50 away from the first end 20 of the housing 12, thereby holding the syringe 50 in the retracted position until activated. Other components of the device 10 may also position the syringe 50 relative to the housing 12.

Figure 10A:
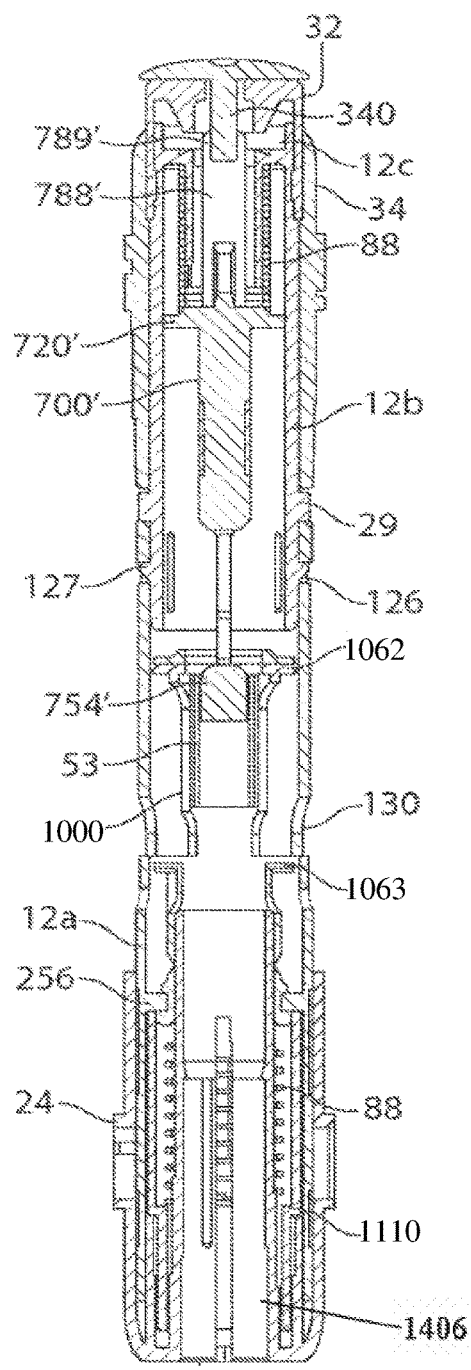
FIGS. 10A and 10B illustrate cross-sectional views of an exemplary assembled automatic injection device offset by 90° angles from each other, in which the syringe housing sub-assembly and the firing mechanism sub-assembly are coupled together.
Figure 10B:
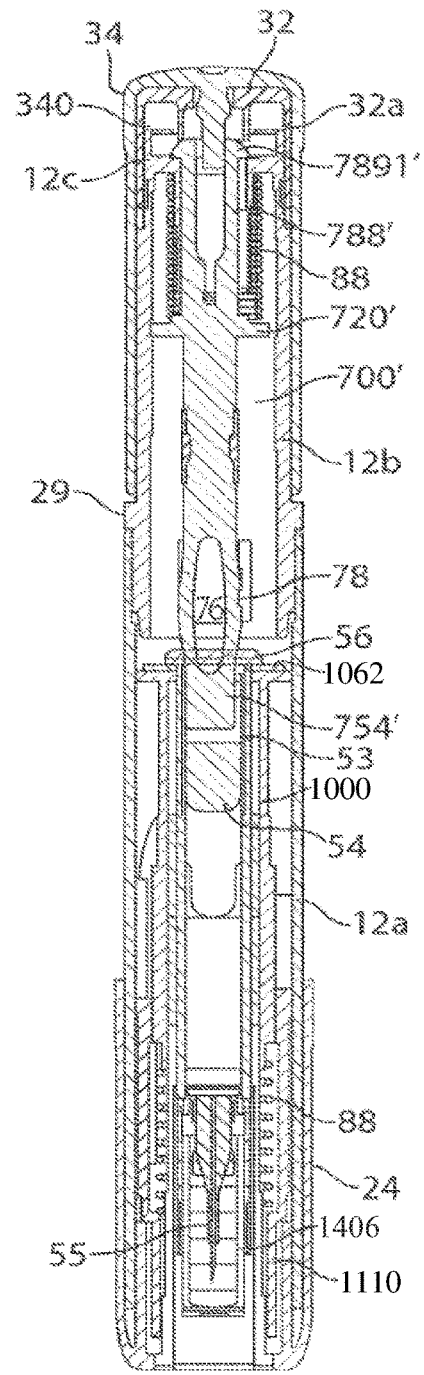

FIGS. 10A and 10B are cross-sectional views at 90° offset angles from each other, illustrating an assembled automatic injection device, wherein the syringe housing sub-assembly 121 and the firing mechanism sub-assembly 122 of FIG. 5 are coupled together, such that the pressurizer 754' of the syringe actuation component 700' extends into the barrel portion 53 of a syringe 50 housed in the syringe housing sub-assembly 121 and is in communication with a bung 54 of the syringe 50. Referring again to FIGS. 7 and 10B, the syringe actuation component 700' includes, at its proximal end 700a', a pressurizing end 754' for applying pressure to the bung 54, a plunger rod portion 70 with a compressible expanded portion 76 (illustrated as the plunger elbows 78), as well as other components, such as components for anchoring the coil spring 88 to the syringe actuation component 700', as described below. The compressible expanded portion 76 facilitates movement of a corresponding syringe 50 into a projecting position and expulsion of the contents of the syringe 50. Alternatively, the syringe actuation component 700' may comprise multiple actuators for moving and/or promoting actuation of the syringe 50.

As shown in FIG. 10B, the trigger anchoring portion 789' of the syringe actuation component 700' is anchored at the distal end of the housing 12 by the firing button 32. When a patient activates the firing button 32, driving arms 32a connected to the firing button 32 compress the tabbed feet 7891' of the trigger anchoring portion 789' inwards, thereby decreasing the distance (plunger arm width) between the tabbed feet of the plunger arms 788a', 788b'. This releases the syringe actuation mechanism 700' and the spring 88.

In an exemplary embodiment, during a first operational stage, the plunger 70 advances under the spring force of the spring 88 and enters the bore of the syringe 50. The elbows 78 of the plunger 70 may compress radially inwardly, at least partly, as the plunger 70 enters the bore of the syringe 50. In an exemplary embodiment, the radially inward compression of the elbows 78 may cause the plunger 70 to elongate or lengthen along the longitudinal axis. In an exemplary embodiment, the pressurizing end 754' of the plunger 70 may initially be spaced from the bung 54, and the plunger 70 may move toward the bung 54 during the first operational stage until the pressurizing end 754' of the plunger 70 comes into initial contact with the bung 54.

During a second operational stage, the pressurizing end 754' of the plunger 70 pushes against the bung 54. In this stage, the elbows 78 of the plunger 70 exert frictional forces against the inner wall of the syringe, which impedes the forward movement of the pressurizing end 754' against the bung 54. Furthermore, the incompressible nature of the dose of the liquid therapeutic substance in the syringe acts against the forward movement of the pressurizing end 754' against the bung 54. As a result, the combination of the frictional forces exerted by the elbows 78 and the resistance force of the liquid inside the syringe 50 impedes farther movement of the pressurizing end 754' against the bung 54. When the combination of these forces exceeds the forces holding the syringe carrier 1000 in place, the syringe 50 and the syringe carrier 1000 are caused to move forward toward the proximal end of the device under the force of the spring 88. During the forward movement of the syringe, the initial biasing force provided by the first coil spring 88 is sufficient to overcome the biasing force of the second coil spring 89 to allow movement of the syringe 50 against the backward biasing force of the second coil spring 89. The forward movement of the syringe 50 causes the tip of the needle 55 to project from the proximal end 20 of the housing 12.

In this exemplary embodiment, during a third operational stage, when the syringe carrier 1000 is fully extended in the housing of the device, the plunger 70 moves farther into the bore of the syringe 50. In an exemplary embodiment, the radially inward compression of the elbows 78 may cause the plunger 70 to elongate or lengthen along the longitudinal axis. As the plunger 70 moves into the syringe 50, the pressurizing end 754' of the plunger 70 pushes the bung 54 into the syringe 50 and causes the contents of the syringe 50 to be ejected from the syringe through the needle 55.

In another exemplary embodiment, after the spring 88 is released, the plunger 70 may advance under the spring force of the spring 88 and enter the bore of the syringe 50, and the elbows 78 of the plunger 70 may compress radially inwardly, at least partly, as the plunger enters the bore of the syringe 50. In an exemplary embodiment, the radially inward compression of the elbows 78 may cause the plunger 70 to elongate or lengthen along the longitudinal axis.

The pressurizing end 754' of the plunger 70 may initially be spaced from the bung 54 in an exemplary embodiment, and the plunger 70 may move toward the bung 54 until the pressurizing end 754' of the plunger 70 comes into initial contact with the bung 54. The pressurizing end 754' of the plunger 70 may subsequently push against the bung 54. The elbows 78 of the plunger 70 may exert frictional forces against the inner wall of the syringe, which impedes the forward movement of the pressurizing end 754' against the bung 54. Furthermore, the incompressible nature of the dose of the liquid therapeutic substance in the syringe acts against the forward movement of the pressurizing end 754' against the bung 54. As a result, the combination of the frictional forces exerted by the elbows 78 and the resistance force of the liquid inside the syringe 50 may impede farther movement of the pressurizing end 754' against the bung 54. When the combination of these forces exceeds the forces holding the syringe carrier 1000 in place, the syringe 50 and the syringe carrier 1000 are caused to move forward toward the proximal end of the device under the force of the spring 88. During the forward movement of the syringe, the initial biasing force provided by the first coil spring 88 is sufficient to overcome the biasing force of the second coil spring 89 to allow movement of the syringe 50 against the backward biasing force of the second coil spring 89. The forward movement of the syringe 50 causes the tip of the needle 55 to project from the proximal end 20 of the housing 12. In this exemplary embodiment, when the syringe carrier 1000 is fully extended in the housing of the device, the elbows 78 of the plunger 70 may compress radially inwardly to a greater extent and the plunger 70 may move farther into the bore of the syringe 50. In an exemplary embodiment, the radially inward compression of the elbows 78 may cause the plunger 70 to elongate or lengthen along the longitudinal axis. As the plunger 70 moves into the syringe 50, the pressurizing end 754' of the plunger 70 may push the bung 54 into the syringe 50 and cause the contents of the syringe 50 to be ejected from the syringe through the needle 55.

In another exemplary embodiment, prior to operation, the compressible expanded portion 76, illustrated as elbows 78, of the syringe actuation component 700' rests above the flanged distal end 56 of the syringe 50 to allow the compressible expanded portion 76, when pushed by a released coil spring 88, to apply pressure to the syringe barrel portion 53, thereby moving the syringe 50 forward within the housing 12 when actuated. In this exemplary embodiment, in the first operational stage, the expanded region 76 of the plunger 70, formed by the projecting elbows 78, rests against the flanged distal end 56 of the barrel portion 53. This prevents the plunger 70 from traveling within the syringe barrel portion 53.

In this manner, all biasing force from the first coil spring 88 is applied to move the syringe 50 and the syringe carrier 1000 forward towards the proximal end 20 of the device 10. The forward motion of the syringe 50 and the syringe carrier 1000 towards the proximal end 20 of the device 10 may continue against the biasing force of the coil spring 88 until the flanged distal end 56 of the barrel portion 53 abuts a stopping mechanism, such as a stop 256 on the proximal housing component 12a shown in FIG. 10B. One of ordinary skill in the art will recognize that alternate stopping mechanisms may be employed and that exemplary embodiments are not limited to the illustrative stopping mechanism.

The first operational stage may propel the tip of the needle 55 through the opening 28 at the proximal end 20 of the device 10, so that the needle 55 may pierce the patient's skin. During this stage, the syringe barrel portion 53 may preferably remain sealed without expelling the substance through the needle 55. The interference caused by the stopping mechanism may maintain the needle 55 in a selected position extending from the proximal open end 28 of the device 10 during subsequent steps. Until the stopping mechanism stops the movement of the syringe 50, the compressible expanded portion 76 of the plunger 70 may prevent movement of the plunger 70 relative to the barrel portion 53. The stopping mechanism may be positioned at any suitable location relative to the open proximal end 20 to allow the syringe 50 to penetrate the skin by any suitable depth suitable for an injection.

In this exemplary embodiment, the second operational stage commences after the stopping mechanism of the housing 12 catches the flanged portion 56, stopping further movement of the barrel portion 53. During this stage, the continued biasing force of the spring 88 continues to move the syringe actuation component 700' forward, causing the compressible expanded portion 76 to compress radially inwardly and move into the barrel portion 53 of the syringe 50. In an exemplary embodiment, the radially inward compression of the elbows 78 may cause the plunger 70 to elongate along the longitudinal axis. The forward motion of the syringe actuation component 700' within the barrel portion 53 causes the pressurizer 754' to apply pressure to the bung 54, causing expulsion of the syringe contents into an injection site. Because the needle 55 was made to penetrate the patient's skin in the first operational stage, the substance contained in the barrel portion 53 of the syringe 50 is injected directly into a portion of the patient's body.

As also shown in FIGS. 10A and 10B, the distal cap 34 may include a stabilizing protrusion 340 that extends through the firing button 32 and between the tabbed feet 7891' of the syringe actuation component 700' to stabilize the components of the device prior to activation.

In the exemplary embodiment shown in FIG. 10A, a removable rigid needle shield 1406 is coupled to the proximal end of the syringe 50 for protectively covering the needle 55. The rigid needle shield 1406 covers and protects a soft needle shield which keeps the needle 55 sterile before use. Together, the rigid needle shield 1406 and the soft needle shield are meant to prevent accidental needle stick injuries that could be caused by an exposed needle. In an exemplary embodiment, the rigid needle shield 1406 is a hollow tubular member with a substantially cylindrical wall having an inner bore with a substantially circular cross-section. The outer cross-sectional diameter of the cylindrical wall may be substantially constant over the length of the rigid needle shield 1406 or may vary over the length of the rigid needle shield 1406. An exemplary rigid needle shield 1406 may be formed of one or more rigid materials including, but not limited to, polypropylene.

In an exemplary embodiment, a removable soft needle shield (not shown) is provided within the bore of the rigid needle shield 1406 to provide a sealing layer between the needle 55 and the rigid needle shield 1406. An exemplary soft needle shield may be formed of one or more resilient materials including, but not limited to, rubber.

In the needle assembly shown in FIGS. 10A and 10B, the needle 55 is covered by the soft needle shield and the rigid needle shield 1406. The rigid needle shield 1406 is, in turn, covered by the proximal removable cap 24 of the automatic injection device. The proximal removable cap 24 is provided in the automatic injection device for covering the proximal end of the housing of the automatic injection device to prevent exposure of the needle prior to an injection.

Figure 11:
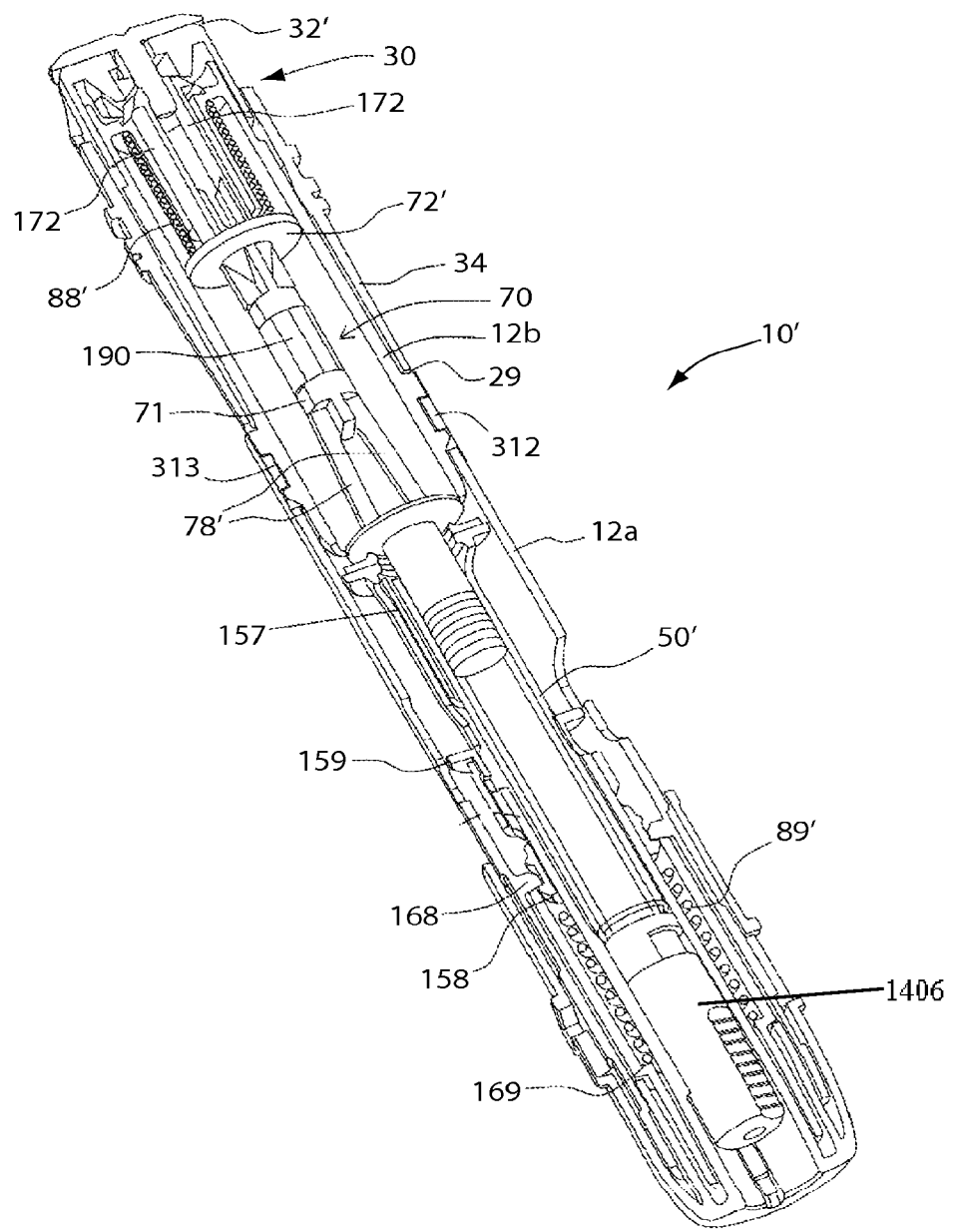
FIG. 11 illustrates a cross-sectional view of an exemplary assembled automatic injection device.

FIG. 11 is a cross-sectional view of an assembled automatic injection device 10'. The illustrative embodiment of the automatic injection device 10' includes proximal and distal housing components 12a, 12b. The proximal and distal housing components 12a, 12b are assembled together to form a complete housing. As shown, a proximal housing component 12a, forming a proximal end of the housing, receives a proximal end of the distal housing components 12b.

A removable rigid needle shield 1406 is coupled to the proximal end of the syringe 50' for protectively covering the needle (not shown).

A cooperating projection 312 and groove 313, or a plurality of cooperating projections 312 and grooves 313, facilitate assembly and coupling of the proximal and distal housing components 12a, 12b in the illustrative embodiment. Other suitable assembly mechanisms may alternatively be employed. A shelf 29 formed on an outer surface of the distal housing component 12b to form a stop for the removable distal cap 34.

As shown, the firing button 32' may be a cap covering the distal end of the distal housing component 12b. The illustrative firing button 32' slides relative to the distal housing component 12b to actuate a syringe actuator, such as the plunger 70. The illustrative firing button 32' releasably retains flexible anchoring arms 172 of the plunger 70'. When depressed, the firing button 32' releases the flexible anchoring arms 172 to allow a first biasing mechanism, illustrated as spring 88' to propel the plunger 70' towards the proximal end of the device 10'.

In the embodiment of FIG. 11, the plunger 70' further includes a flange 72' located between the compressible expanded portion 78' and the distal end of the plunger rod 71'. A first biasing mechanism 88' is seated between an interior distal end of the housing and the flange 72' to bias the plunger 70 towards the proximal end of the housing.

When the firing button 34' releases the anchoring arms 172, the coil spring 88', or other suitable biasing mechanism propels the plunger 70' towards the proximal end 20 of the device 10.

The plunger 70' further includes an indicator 190 formed at an intermediate portion of the plunger rod 71 between the flange 72' and the compressible expanded portion, illustrated as flexible elbows 78'. The indicator 190 may indicate to the patient of the device 10' when the dose from the syringe 50 has been fully or substantially fully ejected. In the illustrative embodiment, the indicator 190 is formed on a portion of the plunger rod 71' between the compressible expanded central portion 76 and the flange 72'. As the plunger rod 71 moves during operation, the indicator 190 advances towards and aligns with window 130 in the housing as the dose empties from the syringe. The indicator 190, which is preferably a different color or pattern from the substance being injected, fills the window 130 entirely to indicate that the dosage has been ejected. Any suitable indicator may be used.

The syringe 50' of FIG. 11 may include protrusions or other suitable component to facilitate controlled movement of the syringe within the housing 12'. For example, with reference to FIG. 11, the syringe 50' includes a sleeve 157 forming a proximal protrusion 158 for abutting a proximal side of a first protrusion 168 formed on an inner surface of the housing 12' for limited movement of the syringe 50' in the distal direction within the housing 12'. The sleeve 157 may also form a flange 159 that may abut the distal side of the first protrusion 168 to limit movement of the syringe 50' in the proximal direction during an injection.

Figure 12:
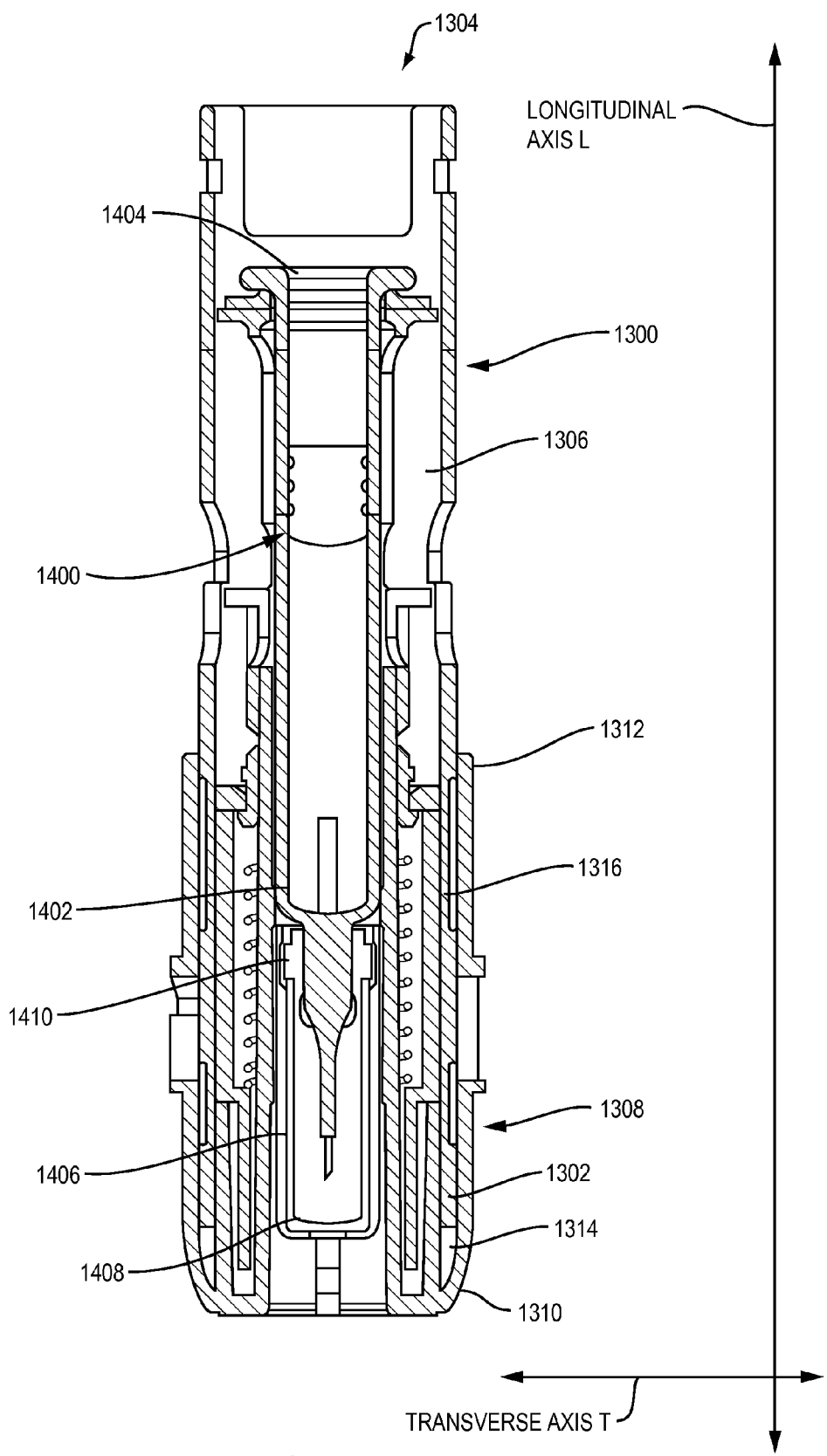
FIG. 12 illustrates a cross-sectional view of an exemplary automatic injection device housing an exemplary syringe.

In the embodiment of FIG. 12, the second biasing mechanism, illustrated as coil spring 89' is disposed about a proximal portion of the syringe 50'. A shelf 169 formed at a proximal inner surface of the housing 12' receives a proximal end of the coil spring 89'. The proximal protrusion 158 of the syringe sleeve 157, or another suitably disposed mechanism, receives the distal end of the coil spring 89'. As described above, the second biasing mechanism 89' biases the syringe 50' in a retracted position within the housing 12' until activation of the device 10.

FIG. 12 illustrates a cross-sectional view taken along the longitudinal axis L of the housing 1300 of an automatic injection device housing an exemplary syringe 1400. The housing 1300 of the automatic injection device extends substantially along the longitudinal axis L between a proximal end 1302 and a distal end 1304. The housing 1300 includes a hollow internal bore 1306 for accommodating the syringe 1400 and other related components, e.g., the needle, a soft needle shield covering the needle, a rigid needle shield 1406 covering the needle and the soft needle shield, etc.

The proximal end 1302 of the housing 1300 includes or is fitted with a removable proximal cap 1308. The proximal cap 1308 extends substantially along the longitudinal axis L between a proximal end 1310 and a distal end 1312. The proximal cap 1308 includes a hollow internal bore 1314 for accommodating part or the entire length of a rigid needle shield 1406. In an exemplary embodiment, the hollow internal bore 1314 of the proximal cap 1308 may also accommodate a proximal portion of the syringe body 1400.

The syringe 1400 extends substantially along the longitudinal axis L between a proximal end 1402 and distal end 1404. The proximal end 1402 of the syringe 1400 is coupled to a needle that may be covered by the removable rigid needle shield 1406. In some exemplary embodiments, the needle may be covered by a removable soft needle shield that is, in turn, covered by the rigid needle shield 1406. The rigid needle shield 1406 extends substantially along the longitudinal axis L between a closed proximal end 1408 and an open distal end 1410 that abuts the proximal end 1402 of the syringe 1400. Exemplary lengths of rigid needle shields 1406 range from about 5 mm to about 30 mm, but are not limited to this range. In exemplary embodiments, the syringe 1400 may be housed within the housing 1300 of the automatic injection device such that the rigid needle shield 1406 is disposed partly or entirely within the proximal cap 1308.

III. EXEMPLARY COMPONENT INTERACTIONS AFFECTING SHROUD DEPLOYMENT

The deployment of a shroud 1110 from a retracted position to an extended position involves the components of the syringe housing sub-assembly 121 illustrated in FIG. 8. Certain interactions among the components of the syringe housing sub-assembly 121 during the shroud deployment process give rise to forces that tend to impede the deployment process. Exemplary embodiments configure one or more components of the syringe housing sub-assembly 121 in order to minimize the interactions so that shroud deployment is consistently, reliably and completely achieved.

A first type of interaction occurs between the rails 1007 of the syringe carrier 1000 and the internal longitudinal grooves provided in the main tubular body portion 1116 of the shroud 1110. During shroud deployment, the grooves in the shroud 1110 contact and move relative to the rails 1007 of the syringe carrier 1000 toward the needle. This interaction between the grooves in the shroud 1110 and the rails 1007 of the syringe carrier 1000 gives rise to frictional forces that tend to impede the shroud deployment process and may result in shroud deployment failure in some instances.

Figure 13A:
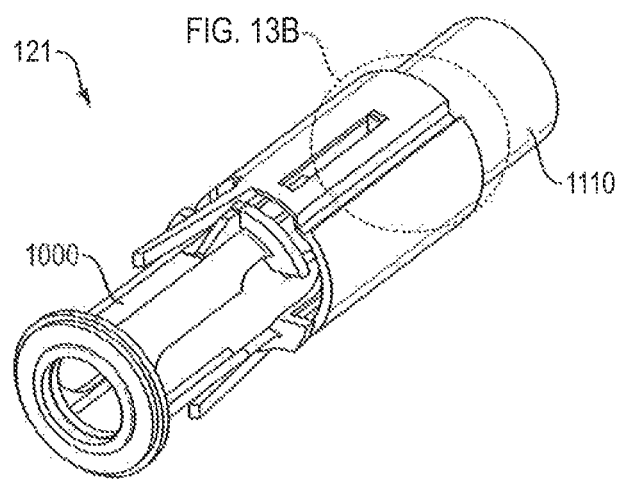
FIG. 13A illustrates a perspective view of a syringe housing sub-assembly in which the shroud is assembled over the syringe carrier.
Figure 13B:
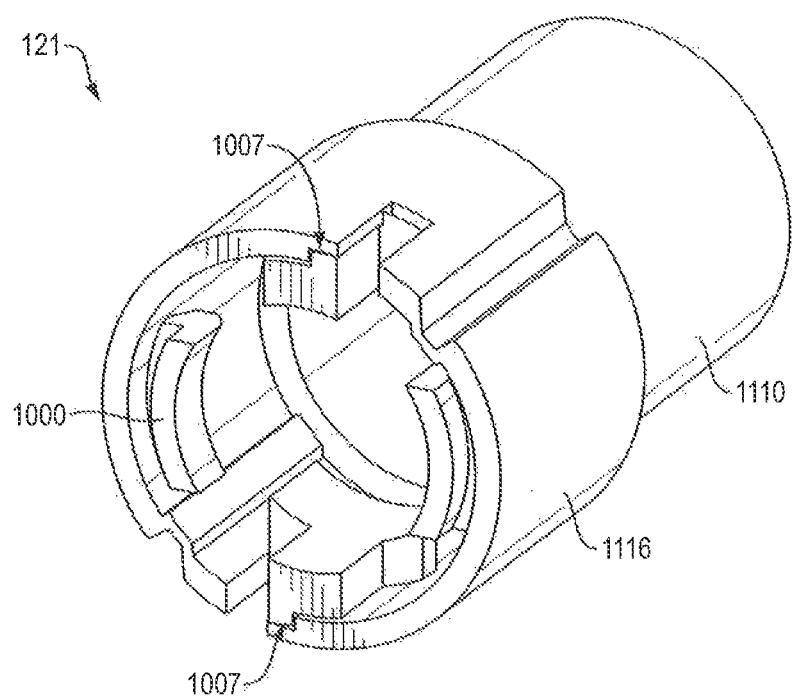
FIG. 13B is a transverse sectional view of the syringe housing sub-assembly of FIG. 13A, showing contact regions at which the grooves in the shroud contact with and move relative to the rails of the syringe carrier.
Figure 13C:
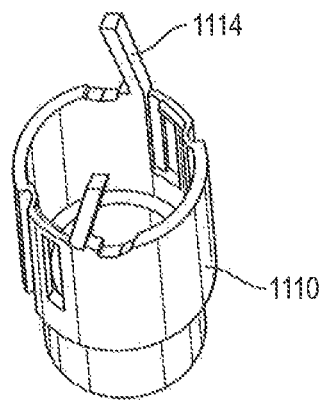
FIG. 13C shows a measurement of the inner diameter between two oppositely-positioned grooves of the shroud.
Figure 13D:
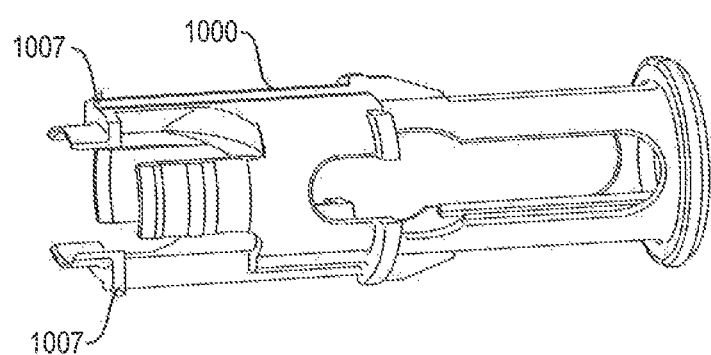
FIG. 13D shows a measurement of the outer diameter between two oppositely-positioned rails of the syringe carrier.

FIG. 13A illustrates a perspective view of a syringe housing sub-assembly 121 in which the shroud 1110 is assembled over the syringe carrier 1000. FIG. 13B is a transverse sectional view of the syringe housing sub-assembly 121 of FIG. 13A, showing contact regions at which the grooves in the shroud 1110 contact with and move relative to the rails 1007 of the syringe carrier 1000. FIG. 13C shows a measurement of the inner diameter between two oppositely-positioned grooves of the shroud 1110. An exemplary inner diameter is about 15.60 mm, although other sizes are possible. FIG. 13D shows a measurement of the outer diameter between two oppositely-positioned rails 1007 of the syringe carrier 1000. An exemplary outer diameter is about 15.51 mm, although other sizes are possible.

A second type of interaction occurs between the distal arms 1114 of the shroud 1110 and the flange 256 provided in or adjacent to the inner surface of the proximal housing component 12a. The flange 256 includes one or more openings 255 that allow the distal arms 1114 of the shroud 1110 to pass through the flange 256 during shroud deployment. In an early stage in the shroud deployment process, the sides of the distal arms 1114 come into contact with the flange 256 (at the edge of the opening 255) in the proximal housing component 12a, and are caused to bend by the engagement with the flange 256. This engagement of the distal arms 1114 of the shroud 1110 with the flange 256 gives rise to frictional forces that tend to impede the shroud deployment process and may result in shroud deployment failure in some instances.

Figure 14A:
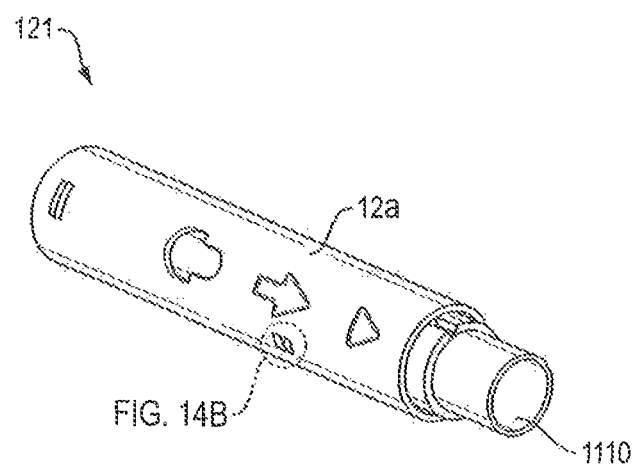
FIG. 14A illustrates a perspective view of a syringe housing sub-assembly in which the shroud is fully or partially disposed in the proximal housing component.
Figure 14B:
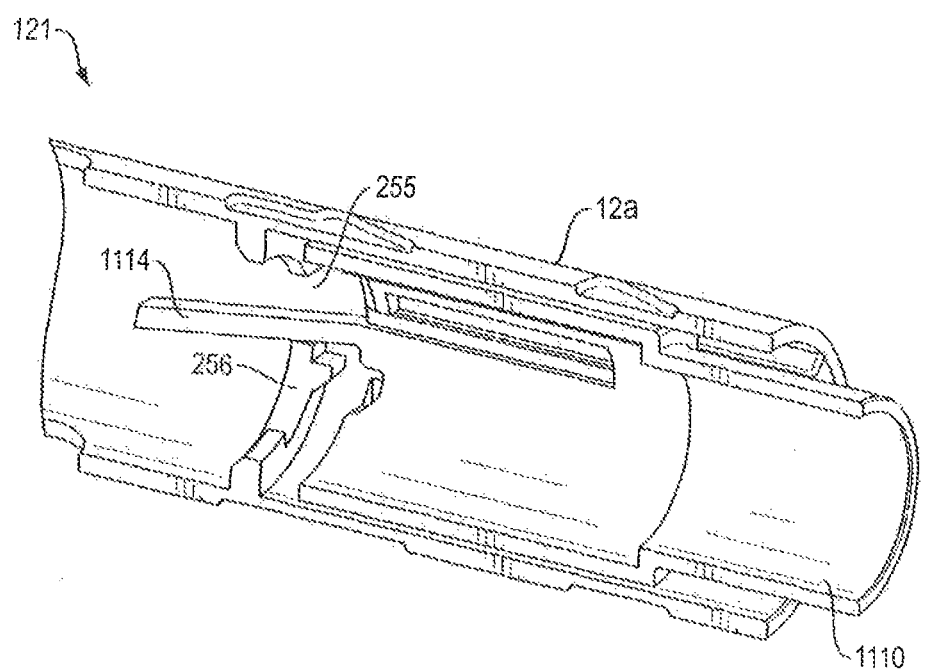
FIG. 14B illustrates a longitudinal sectional view of the syringe housing sub-assembly of FIG. 14A, showing the engagement of the distal arms of the shroud with the flange in the proximal housing component.
Figure 14C:
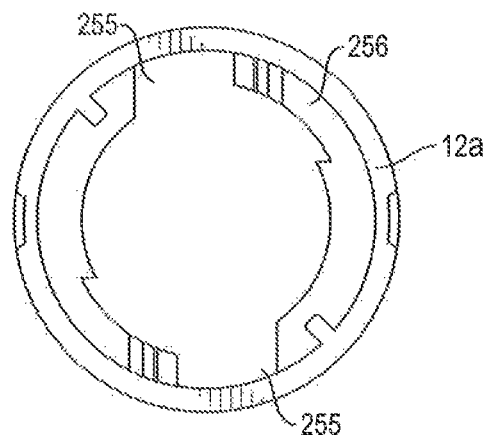
FIG. 14C shows a measurement of the distance between two oppositely-positioned openings in the flange that may accommodate the distal arms of the shroud as the arms pass through the flange.
Figure 14D:
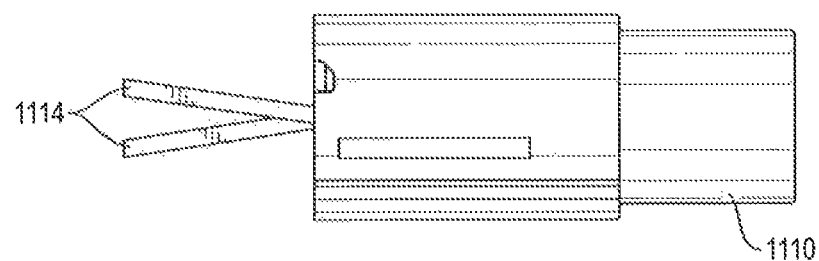
FIG. 14D shows a measurement of the span of the distal arms of the shroud (i.e., the distance between the terminal ends of the distal arms taken perpendicular to the length of the shroud).

FIG. 14A illustrates a perspective view of a syringe housing sub-assembly 121 in which the shroud 1110 is fully or partially disposed in the proximal housing component 12*a*. FIG. 14A highlights an area of the proximal housing component 12*a* at which the distal arms 1114 of the shroud 1110 engage with the flange 256 in the proximal housing component 12*a*. FIG. 14B illustrates a longitudinal sectional view of the syringe housing sub-assembly 121 of FIG. 14A, showing the engagement of the distal arms 1114 of the shroud 1110 with the flange 256 in the proximal housing component 12*a*. FIG. 14C shows a measurement of the distance between two oppositely-positioned openings 255 in the flange 256 that may accommodate the distal arms 1114 of the shroud 1110 as the arms pass through the flange 256. An exemplary distance of the flange openings is about 3.10 mm, although other sizes are possible. FIG. 14D shows a measurement of the span of the distal arms 1114 of the shroud 1110 (i.e., the distance between the terminal ends of the distal arms taken perpendicular to the length of the shroud). An exemplary span is about 6.13 mm, although other sizes are possible.

A third type of interaction occurs among the distal arms 1114 of the shroud 1110, the proximal housing component 12*a*, and the syringe carrier 1000, as the distal arms 1114 pass through the constrained space provided between the proximal housing component 12*a* and the syringe carrier 1000. The distal arms 1114 of the shroud 1110 are pinched within the constrained space between the outer diameter of the proximal tubular portion 1002 of the syringe carrier 1000 and the inner diameter of the proximal housing component 12*a*. In a later stage in the shroud deployment process, the distal arms 1114 bend due to engagement with the flange 256 of the proximal housing component 12*a*, which causes the arms 1114 to twist within the constrained space between the syringe carrier 1000 and the proximal housing component 12*a* of the automatic injection device. Movement of the distal arms 1114 within the constrained space causes pinching of the distal arms 1114, i.e., causes reverse twisting of the arms so that they can fit between the syringe carrier 1000 and the proximal housing component 12*a*. This pinching effect of the distal arms 1114 of the shroud 1110 gives rise to frictional forces that tend to impede the shroud deployment process and may result in shroud deployment failure in some instances.

In another exemplary embodiment, the constrained space may be provided by a combination of components different from the outer diameter of the proximal tubular portion 1002 of the syringe carrier 1000 and the inner diameter of the proximal housing component 12*a*. For example, the constrained space may be provided between two housing components, or between the inner surface of a housing component and the outer surface of a component different from the syringe carrier 1000.

Figure 15A:
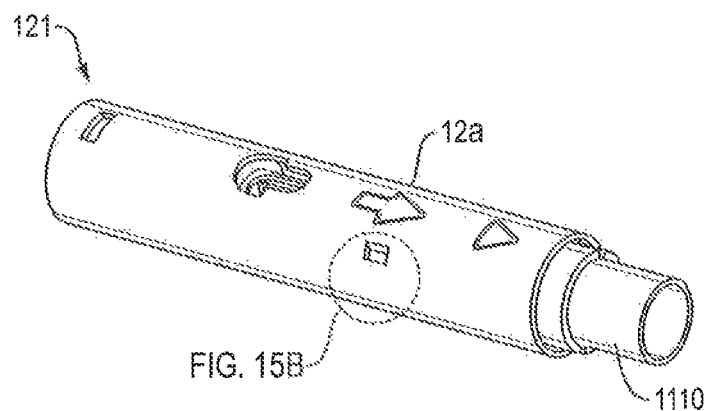
FIG. 15A illustrates a perspective view of a syringe housing sub-assembly in which the syringe carrier and the shroud are assembled and positioned within the proximal housing component.
Figure 15B:
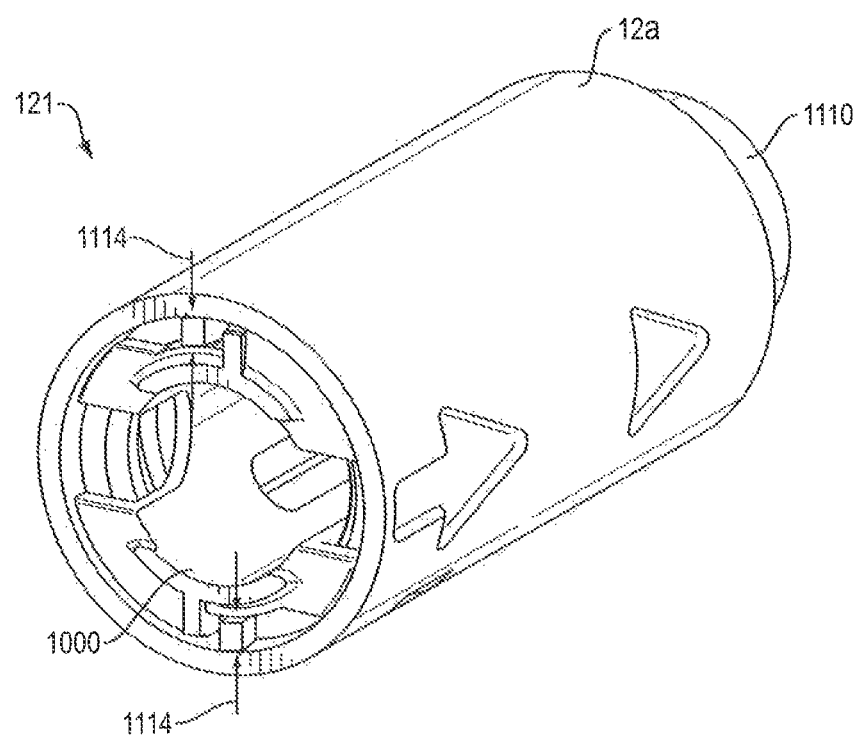
FIG. 15B illustrates a transverse sectional view of the syringe housing sub-assembly of FIG. 15A, showing the pinching of the distal arms of the shroud within the constrained space between the proximal housing component and the syringe carrier.
Figure 15C:
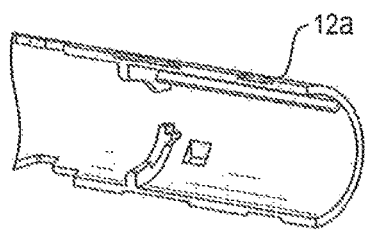
FIG. 15C shows a measurement of the inner diameter of the proximal housing component.
Figure 15D:
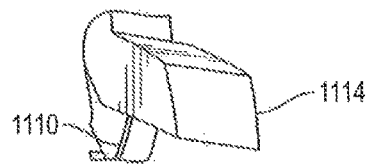
FIG. 15D shows a measurement of the thickness of a distal arm of the shroud.
Figure 15E:
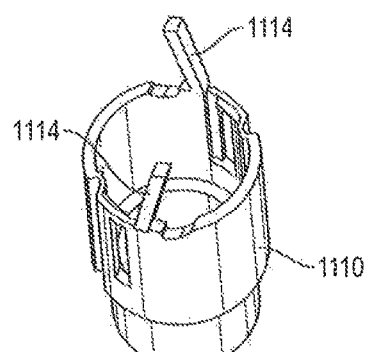
FIG. 15E shows a measurement of the inner diameter between two oppositely-positioned distal arms of the shroud.
Figure 15F:
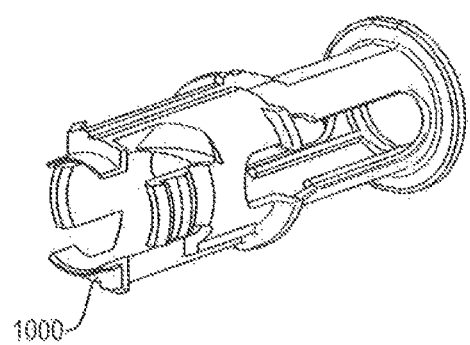
FIG. 15F shows a measurement of the outer diameter of the proximal housing component of the syringe carrier.

FIG. 15A illustrates a perspective view of a syringe housing sub-assembly 121 in which the syringe carrier 1000 and the shroud 1110 are assembled and positioned within the proximal housing component 12*a*. FIG. 15A highlights an area of the proximal housing component 12*a* at which the distal arms 1114 of the shroud 1110 are pinched within the constrained space between the proximal housing component 12*a* and the syringe carrier 1000. FIG. 15B illustrates a transverse sectional view of the syringe housing sub-assembly 121 of FIG. 15A, showing the pinching of the distal arms 1114 of the shroud 1110 within the constrained space between the proximal housing component 12*a* and the syringe carrier 1000. FIG. 15C shows a measurement of the inner diameter of the proximal housing component 12*a*. An exemplary inner diameter is about 17.60 mm, although other sizes are possible. FIG. 15D shows a measurement of the thickness of a distal arm 1114 of the shroud 1110. An exemplary thickness is about 1.45 mm, although other sizes are possible. FIG. 15E shows a measurement of the inner diameter between two oppositely-positioned distal arms 1114 of the shroud 1110. An exemplary inner diameter is about 14.40 mm, although other sizes are possible. FIG. 15F shows a measurement of the outer diameter of the proximal housing component 1002 of the syringe carrier 1000. An exemplary outer diameter is about 14.00 mm, although other sizes are possible.

Figure 16A:
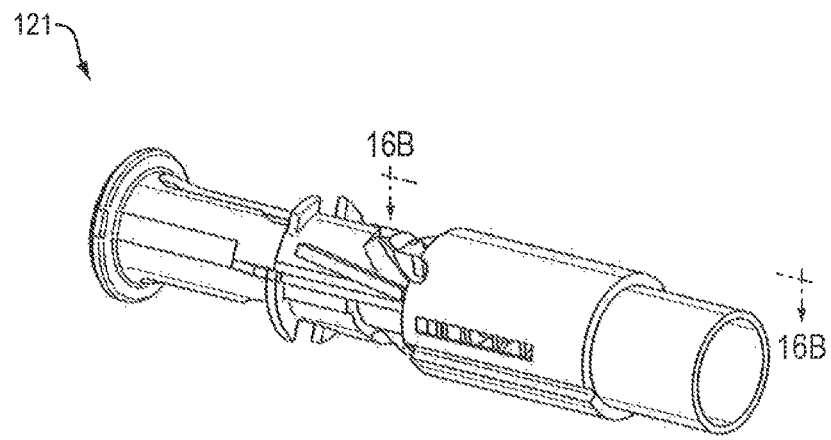
FIG. 16A illustrates a perspective view of a syringe housing sub-assembly in which the biasing mechanism is disposed between the syringe carrier and the shroud.
Figure 16B:
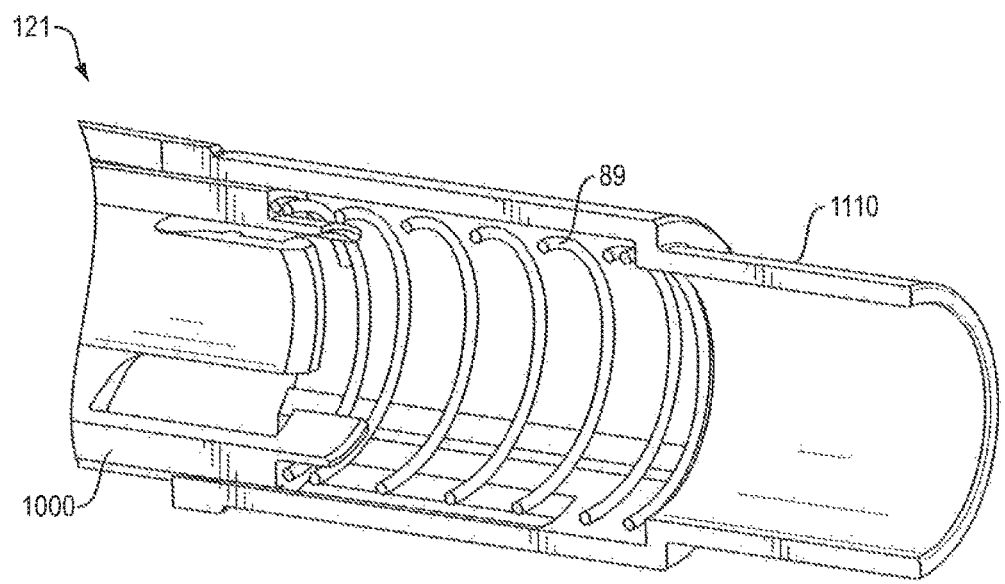
FIG. 16B illustrates a longitudinal sectional view of the syringe housing sub-assembly in which the biasing mechanism is disposed between the syringe carrier and the shroud.
Figure 16C:
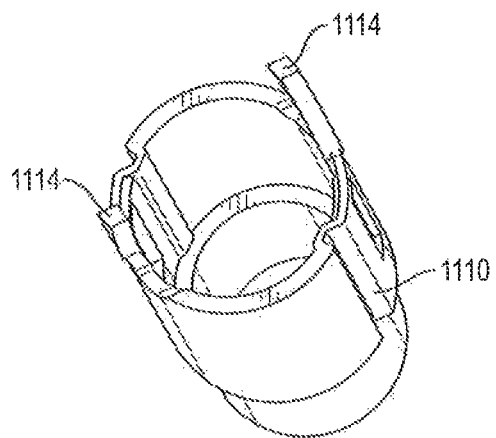
FIG. 16C shows a measurement of the inner diameter of the shroud.
Figure 16D:
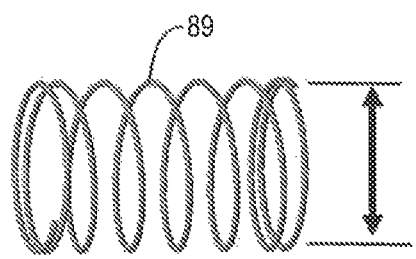
FIG. 16D shows a measurement of the outer diameter of the biasing mechanism.

A fourth type of interaction occurs among the syringe carrier 1000, the shroud 1110, and the biasing mechanism 89 (e.g., a compression spring) disposed between the assembled syringe carrier 1000 and shroud 1110. Defects in the biasing mechanism 89 (due, for example, to material and/or fabrication defects) may give rise to frictional forces that tend to impede the shroud deployment process and may result in shroud deployment failure in some instances. FIG. 16A illustrates a perspective view of a syringe housing sub-assembly 121 in which the biasing mechanism 89 is disposed between the syringe carrier 1000 and the shroud 1110. FIG. 16B illustrates a longitudinal sectional view of the syringe housing sub-assembly 121 in which the biasing mechanism 89 is disposed between the syringe carrier 1000 and the shroud 1110. FIG. 16C shows a measurement of the inner diameter of the shroud 1110. An exemplary inner diameter is about 13.70 mm, although other sizes are possible. FIG. 16D shows a measurement of the outer diameter of the biasing mechanism 89. An exemplary outer diameter is about 13.30 mm, although other sizes are possible.

Figure 17A:
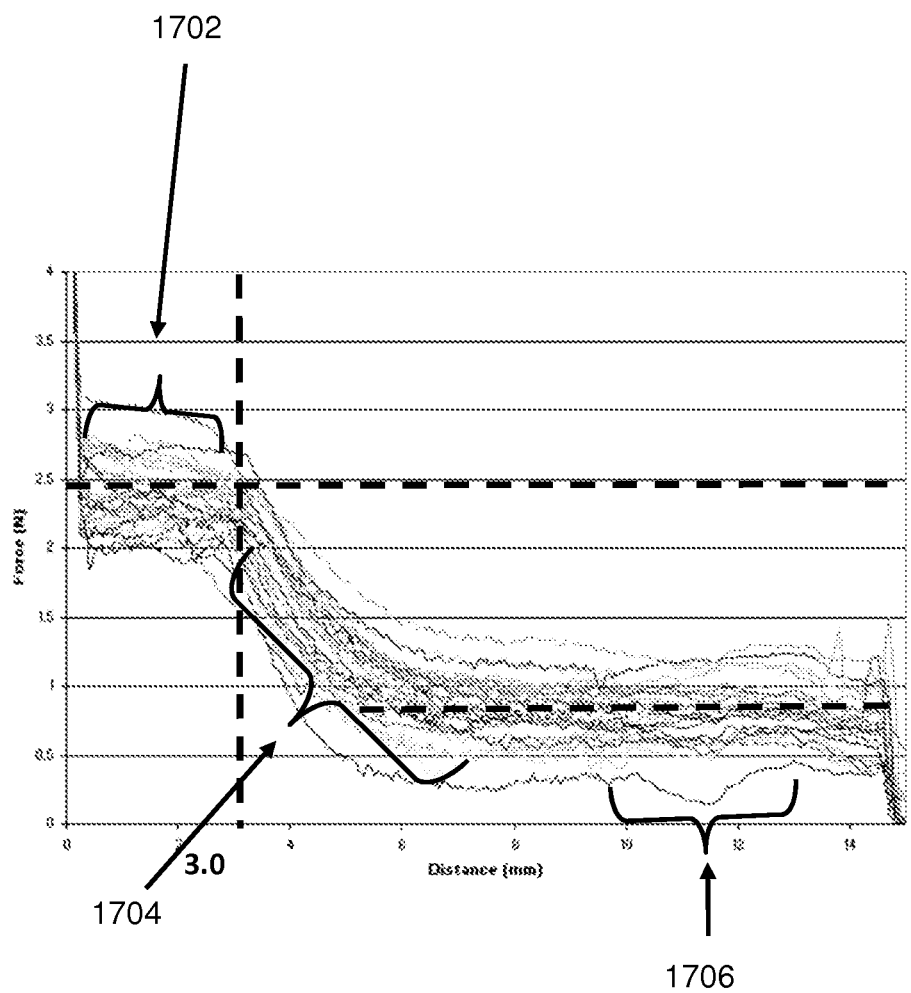
FIGS. 17A and 17B are extension force profile of forces in N (y-axis) generated during the deployment of a shroud against the deployment distance in mm (x-axis).
Figure 17B:
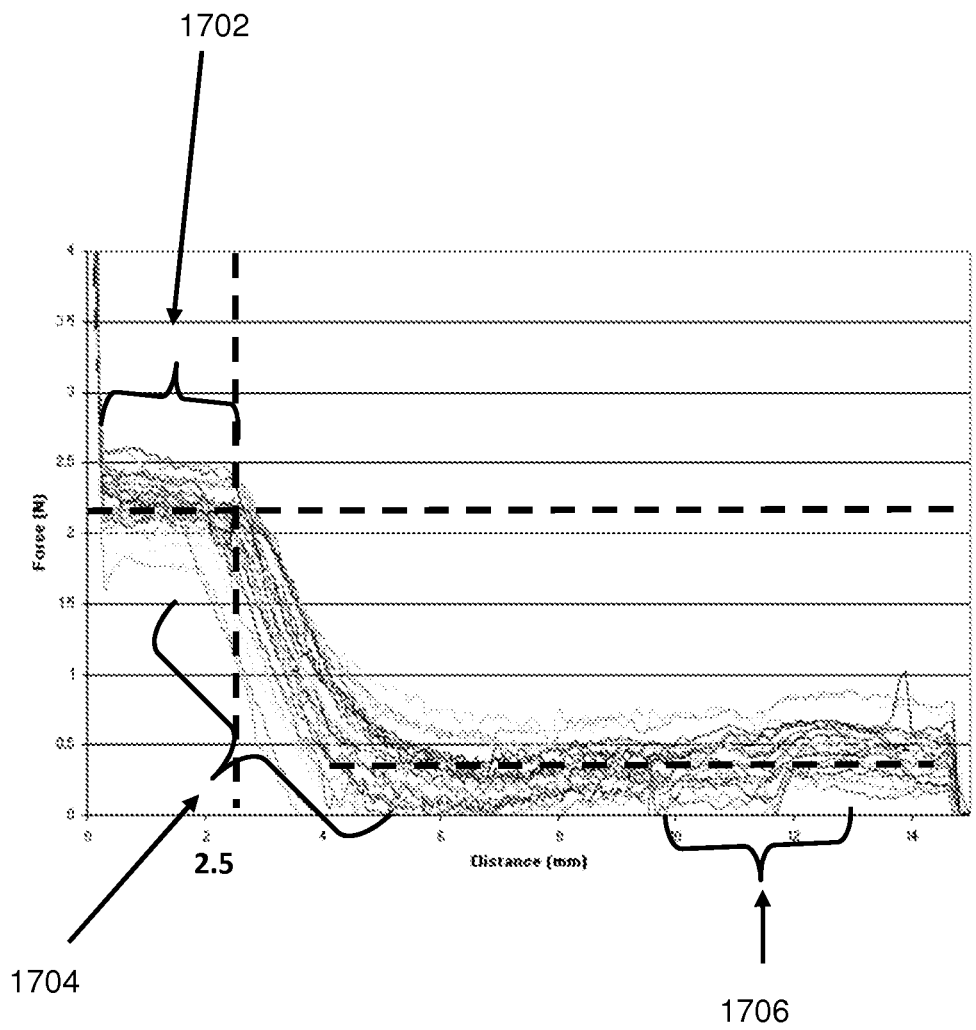

FIGS. 17A and 17B are extension force profile of forces in N (y-axis) generated during the deployment of a shroud against the deployment distance in mm (x-axis). At an early stage 1702 in the shroud deployment process, the first type of interaction (i.e., between the rails 1007 of the syringe carrier 1000 and the internal longitudinal grooves provided in the shroud 1110) and the fourth type of interaction (i.e., among the syringe carrier 1000, the shroud 1110, and the biasing mechanism 89) dominate. These interactions do not give rise to high frictional forces to impede the shroud deployment process, and result in a small and gradual decrease in the forces generated.

At a subsequent stage 1704 in the shroud deployment process, the second type of interaction (i.e., between the distal arms 1114 of the shroud 1110 and the flange 256 in the proximal housing component 12*a*) dominates. In this stage, the distal arms 1114 are bent by engagement with the flange 256, which gives rise to frictional forces that impede the shroud deployment process. This is exhibited as a sharp and large drop in the forces generated. The first and fourth types of interactions are also operative in this stage of the shroud deployment process.

At a subsequent stage 1706 in the shroud deployment process, the third type of interaction (i.e., among the distal arms 1114 of the shroud 1110, the proximal housing component 12*a*, and the syringe carrier 1000) dominates. In this stage, movement of the distal arms 1114 within the constrained space causes pinching of the distal arms 1114, i.e., causes reverse twisting of the arms so that they can fit between the syringe carrier 1000 and the proximal housing component 12*a*. The pinching effect of the distal arms 1114 of the shroud 1110 gives rise to frictional forces that tend to impede the shroud deployment process. This is exhibited as a drop or downward peak in the forces generated. The first, second and fourth types of interactions are also operative in this stage of the shroud deployment process.

IV. CONFIGURATION OF EXEMPLARY AUTOMATIC INJECTION DEVICES TO IMPROVE SHROUD DEPLOYMENT

Exemplary embodiments may configure one or more features of an automatic injection device in order to ensure consistent, reliable and complete shroud deployment within an acceptably short period of time after an injection is performed. Exemplary configurations may include, but are not limited to, one or more configurations of the proximal housing component 12a, the shroud 1110, the syringe carrier 1000, combinations of the aforementioned configurations, and the like.

Figure 18:
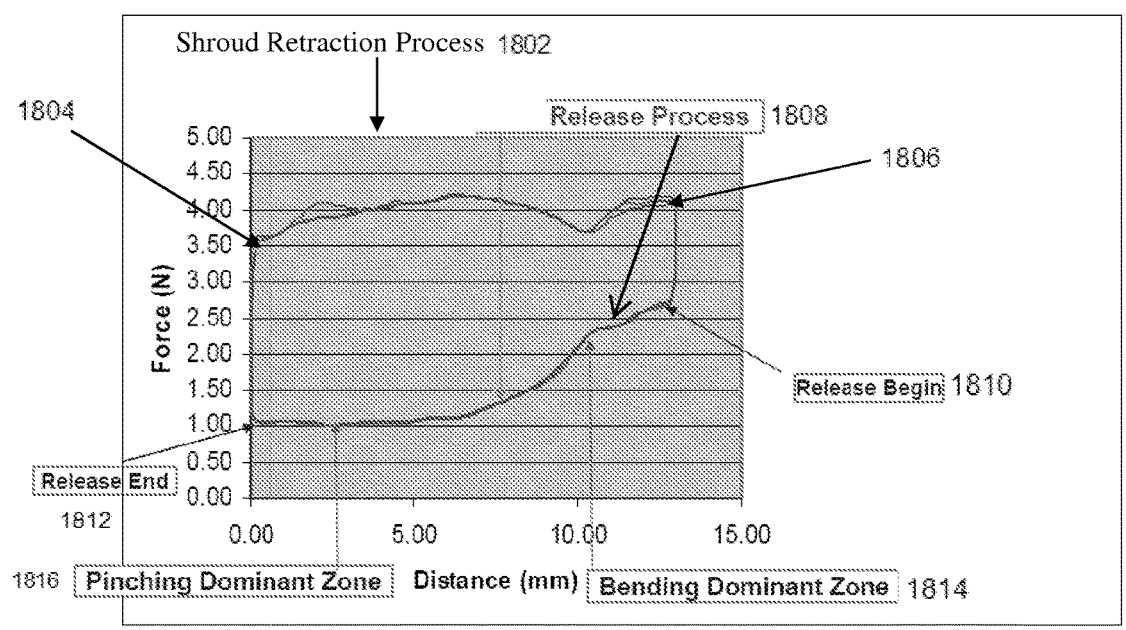
FIG. 18 illustrates an exemplary retraction and extension force profile of forces in N (y-axis) against the deployment distance in mm (x-axis) during the retraction and deployment of a shroud.

FIG. 18 illustrates an exemplary retraction and extension force profile of forces in N (y-axis) against the deployment distance in mm (x-axis) during the retraction and deployment of a shroud 1110. Different forces combine to generate the force profile illustrated in FIG. 18. Exemplary forces include, but are not limited to, the force exerted by the biasing member 89, the force bending the distal arms 1114 of the shroud 1110, the force twisting the distal arms 1114, and the like. In an exemplary embodiment, a shroud 1110 may travel a distance from about 12 mm to about 18 mm during the shroud deployment process, but is not limited to this exemplary range. In an exemplary embodiment, a shroud 1110 may travel about 15.2 mm during the shroud deployment process.

Portion 1802 of FIG. 18 illustrates exemplary forces generated during the shroud retraction process in which the shroud is moved from an extended position to a retracted position to allow the needle to be exposed through a proximal opening in the shroud. Upon retraction of the shroud, the needle may be used to administer an injection at an injection site. The shroud retraction process begins at point 1804 (at which the shroud is extended toward the proximal end of the device) and ends at point 1806 (at which the shroud is retracted toward the distal end of the device).

Portion 1808 of FIG. 18 illustrates exemplary forces generated during the shroud deployment process in which the shroud is moved from the retracted position to the extended position to allow the shroud to cover the needle after an injection, and to thereby avoid the risk of accidental needle stick injuries. The forces are measured by a force sensor as the deployed shroud pushes on the sensor during the shroud deployment process. The shroud deployment process begins at point 1810 (at which the shroud is retracted toward the distal end of the device) and ends at point 1812 (at which the shroud is extended toward the proximal end of the device). The extension force decreases significantly at an earlier stage of shroud deployment, e.g., at an x-axis distance range from about 13 mm to about 8 mm. The extension force reaches a plateau at a later stage of shroud deployment, e.g., at an x-axis distance range from about 6.0 mm to about 0.0 mm. In some exemplary embodiments, there is a residual extension force near and at the end of the shroud deployment process. Exemplary residual extension forces may range from about 0.0 N to about 2.0 N in some exemplary embodiments. In FIG. 18, the residual extension force is about 1.00 N.

In exemplary embodiments, lower extensions forces experienced during shroud deployment and lower residual extension forces may correspond to a slowdown in the shroud deployment process. Exemplary embodiments provide structural, functional and operational improvements to the components of the syringe housing sub-assembly 121 to maximize the extension forces during shroud deployment to prevent failures in shroud deployment, for example, non-deployment or incomplete deployment of the shroud.

In exemplary embodiments, decreases in the extension forces during an early stage in the shroud deployment process may be attributable to bending of the distal arms 1114 of the shroud 1110. In the early stage in the shroud deployment process, the distal arms 1114 engage with the flange 256 in the housing 12a of the automatic injection, and are caused to bend by the engagement with the flange 256. The bending effect of the distal arms 1114 is dominant in region 1814 of the extension force profile, and is reflected in the decreases in the extension forces at an x-axis range of between about 13 mm and about 8 mm shown in FIG. 18 in an exemplary embodiment. The decreases in the extension forces may correspond to a slowing down of the shroud deployment process in the early stage.

In exemplary embodiments, decreases in the extension forces during a later stage in the shroud deployment process may be attributable to a pinching effect of the distal arms 1114 of the shroud 1110 within a constrained space between the proximal tubular portion 1002 of the syringe carrier 1000 and the internal diameter of the proximal housing component 12a. In the later stage in the shroud deployment process, the distal arms 1114 bend due to engagement with the flange 256 of the proximal housing component 12a, which causes the arms 1114 to twist within the constrained space between the syringe carrier 1000 and the proximal housing component 12a of the automatic injection device. Movement of the distal arms 1114 within the constrained space causes pinching of the distal arms 1114, i.e., causes reverse twisting of the arms so that they can fit between the syringe carrier 1000 and the proximal housing component 12a. The pinching effect of the distal arms 1114 is dominant in region 1816 of the extension force profile, and is reflected in decreases in the extension forces at an x-axis range of between about 4 mm and about 1 mm. In an exemplary embodiment, the decreases in the extension forces at the later stages of the shroud deployment process are reflected in a localized downward peak in the extension force profile, illustrated as peak 2002 in FIG. 20.

Figure 20:
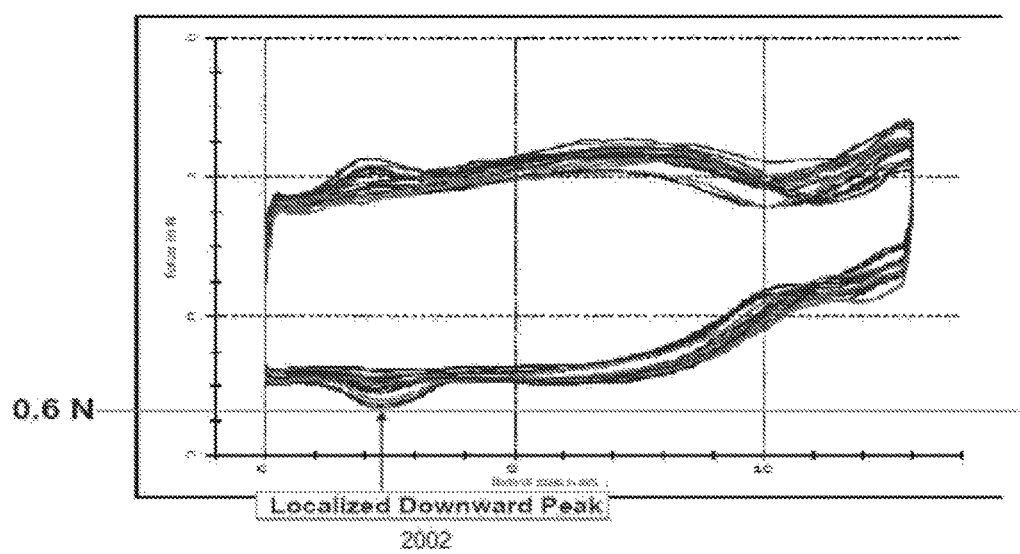
FIG. 20 illustrates an exemplary retraction and extension force profile of forces in N (y-axis) against deployment distances in mm (x-axis) in which a downward peak appears in the later stages of shroud deployment.

In FIG. 18, the downward peak of FIG. 20 is absent in the later stages of shroud deployment. In the exemplary embodiment shown in FIG. 18, the structure, function and operation of exemplary devices is configured to reduce the pinching effect of the distal arms 1114 within the constrained space between the syringe carrier 1000 and the proximal housing component 12a. This maximizes the extension forces experienced during the later stages of shroud deployment as the shroud is deployed from the retracted position to the extended position, which results in an elimination of a downward peak that might otherwise appear in the extension force profile.

Figure 19:
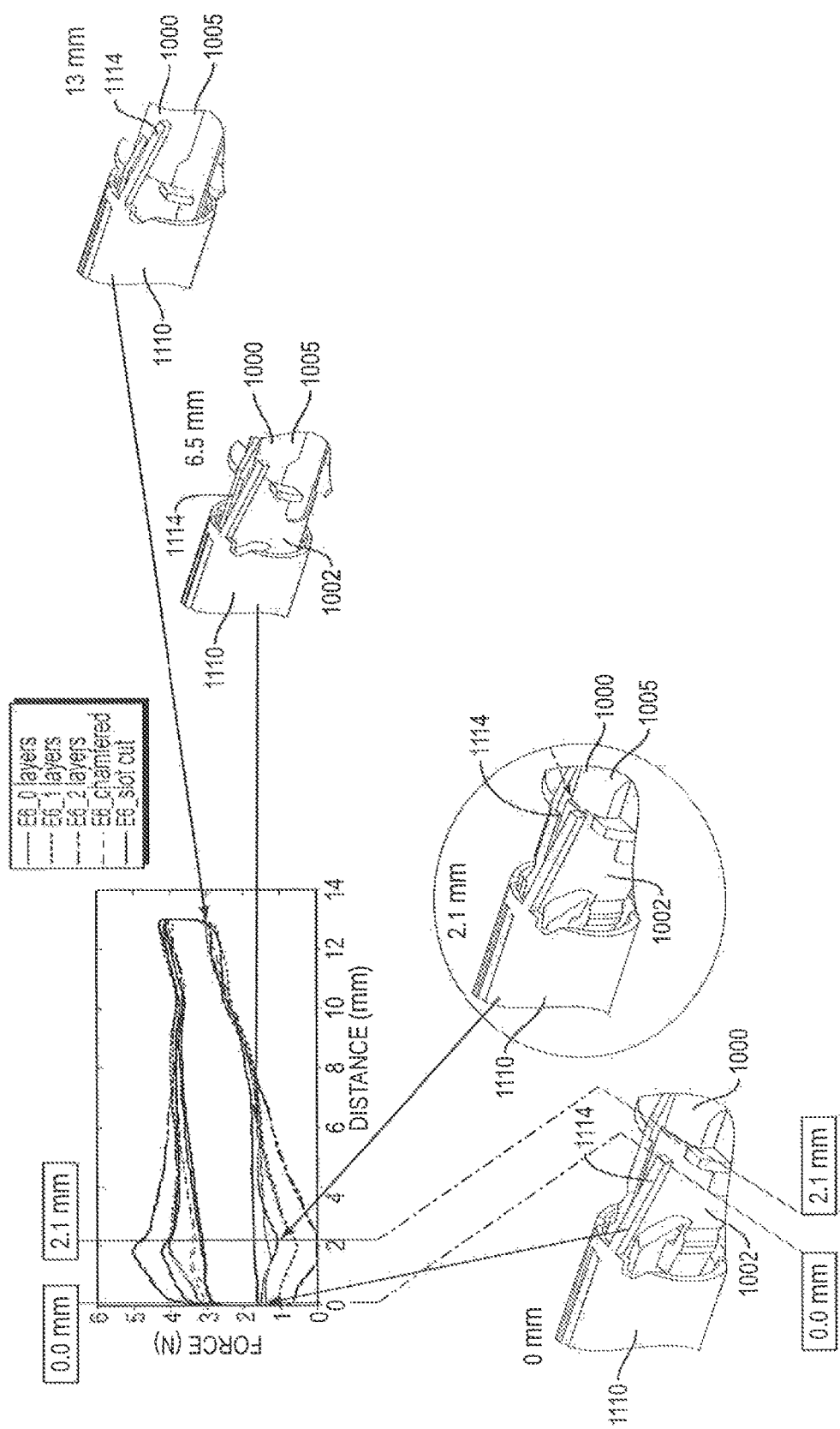
FIG. 19 illustrates an exemplary retraction and extension force profile of forces in N (y-axis) against the distance in mm (x-axis) during the retraction and deployment of a shroud.

FIG. 19 illustrates an exemplary retraction and extension force profile of forces in N (y-axis) against the distance in mm (x-axis) during the retraction and deployment of a shroud. FIG. 19 also shows the positions of the distal arms 1114 of the shroud 1110 relative to the syringe carrier 1000 as the shroud is deployed. For example, at a deployment distance of about 13 mm (i.e., at about the beginning of shroud deployment), the majority of the length of the distal arms 1114 of the shroud 1110 passes over the distal tubular portion 1005 of the syringe carrier 1000. At a deployment distance of about 6.5 mm, the majority of the length of the distal arms 1114 passes over the proximal tubular portion 1002 of the syringe carrier 1000, and the terminal end of the distal arms 1114 approaches the transition portion between the proximal and distal tubular portions of the syringe carrier

1000. Since the outer diameter of the distal tubular portion 1005 of the syringe carrier 1000 is substantially unchanged between the deployment distances of about 13 mm and about 6.5 mm, the force profile shows a gradual decline between these two points.

At a deployment distance of about 2.1 mm, the terminal end of the distal arms 1114 passes over the transition portion between the proximal tubular portion 1002 and the distal tubular portion 1005 of the syringe carrier 1000. In an exemplary embodiment, the transition portion has a larger outer diameter than the proximal tubular portion 1002 and the distal tubular portion 1005 of the syringe carrier 1000. In an exemplary embodiment, the transition portion has an outer diameter of about 14.17 mm. This impedes the passage of the terminal end of the distal arms 1114, and thereby causes a slowdown of the deployment of the shroud. This is exhibited by the dip in the forces at about 2.1 mm.

At a deployment distance of about 0 mm, the entire length of the distal arms 1114 of the shroud 1110 passes over the proximal tubular portion 1002 of the syringe carrier 1000. In an exemplary embodiment, the outer diameter of the proximal tubular portion 1002 is smaller than the transition portion between the proximal tubular portion 1002 and the distal tubular portion 1005 of the syringe carrier 1000. In an exemplary embodiment, the outer diameter of the proximal tubular portion 1002 at the deployment distance of 0 mm is about 14 mm (compared with an outer diameter of the transition region of about 14.17 mm). The lower outer diameter removes the impedance to the passage of the terminal end of the distal arms 1114, and thereby facilitates the deployment of the shroud. This is exhibited by the rise in the forces over deployment distances between about 2 mm and about 0 mm.

FIG. 20 illustrates an exemplary retraction and extension force profile of forces in N (y-axis) against deployment distances in mm (x-axis) in which a downward peak 2002 appears in the later stages of shroud deployment at an x-axis range of between about 4 mm and about 1 mm. The downward peak 2002 results from the pinching effect of the distal arms 1114 within the constrained space between the syringe carrier 1000 and the proximal housing component 12a. In the exemplary embodiment shown in FIG. 20, the downward peak causes a dip of about 0.4 N in the extension force from about 1.0 N in FIG. 18 to about 0.6 N in FIG. 14.

A. Configuration of the Distal Arms of the Shroud

In an exemplary embodiment, the structural configuration of the distal arms 1114 of the shroud 1110 may be modified to maximize the extension forces during the shroud deployment process.

In an exemplary embodiment, a rounded or oval structure may be included at the distal end of the distal arms 1114 of the shroud 1110, or the distal end of the distal arms 1114 may be configured in a rounded or oval structure to facilitate the shroud deployment process.

In an exemplary embodiment, the thickness of the distal arms 1114 of the shroud 1110 may be reduced in order to minimize the pinching effect of the arms 1114 within the constrained space provided between the outer surface of the syringe carrier 1000 and the inner surface of the proximal housing component 12a. The thickness of the distal arms 1114 of the shroud 1110 may be configured to be comfortably accommodated within the height of the constrained space. The thickness of the distal arms 1114 of the shroud 1110 may be at most the height of the constrained space. Exemplary thicknesses of the distal arms 1114 may range from about 1.00 mm to about 2.00 mm, but are not limited to this exemplary range. Exemplary thicknesses may include, but are not limited to, about 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5 mm, and the like.

In an exemplary embodiment, the thickness may be reduced from about 1.45 mm to about 1.40 mm. In an exemplary embodiment, the shroud 1110 with the distal arms 1114 having the reduced thickness of about 1.40 mm may have an inner diameter of about 14.40 mm, and may be accommodated between a proximal housing component 12a having an exemplary inner diameter of about 17.60 mm and a syringe carrier 1000 having an exemplary outer diameter of about 14.00 mm.

Figure 21:
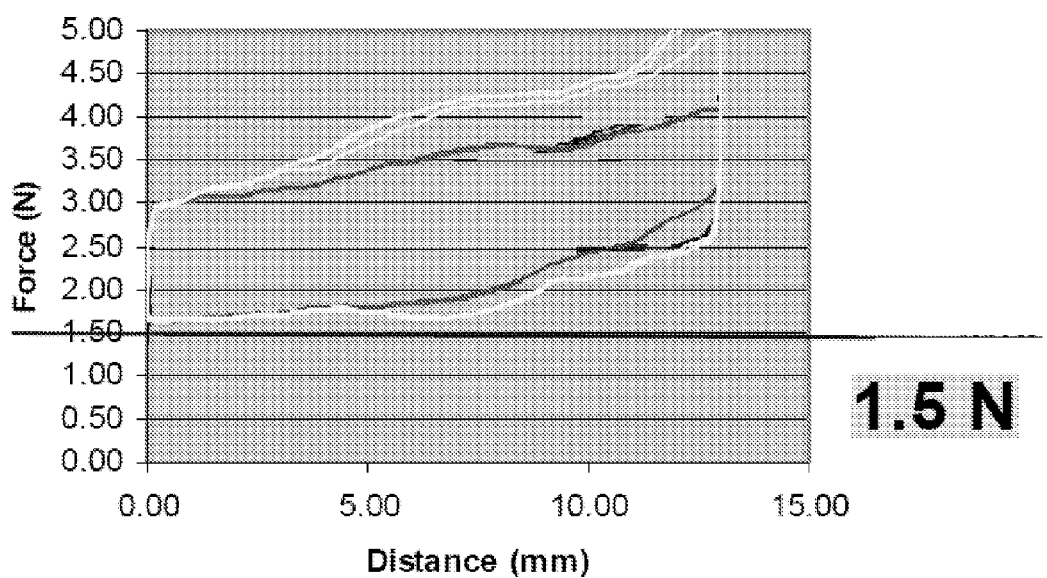
FIG. 21 illustrates a graph showing retraction and extension forces in N (y-axis) generated at different deployment distances in mm (x-axis) during deployment of exemplary shrouds.

FIG. 21 illustrates a graph showing retraction and extension forces in N (y-axis) generated at different deployment distances in mm (x-axis) during deployment of exemplary shrouds. The thickness of the distal arms 1114 of the shrouds 1110 was decreased to a small extent and a rounded structure was included at the distal end of the arms. FIG. 21 shows that the extension force does not exhibit a sharp drop unlike in FIG. 18, i.e., the downward slope in FIG. 21 is more gradual than the downward slope in FIG. 18. This is due to the structural change in the distal arms, which reduces the bending effect of the distal arms during the early stages of the shroud deployment process. The residual extension force in FIG. 21 at the end of the deployment is about 1.5 N, which is higher than the residual extension of about 1.0 N in FIG. 18. A comparison between FIGS. 18 and 21 indicates that the configured distal arms result in a gradual drop in the extension forces over the deployment process and in an increase in the residual extension force.

In an exemplary embodiment, the distal arms 1114 of the shroud 1110 may be rotated relative to a locating groove on the shroud 1110. In an exemplary embodiment, the diverging angle of the distal arms 1114 may be increased or decreased. Exemplary diverging angles may range from about 0 degrees to about 45 degrees, but are not limited to this exemplary range.

B. Configuration of the Flange of the Proximal Housing Component

In the second type of interaction described above, the sides of the distal arms 1114 contact the flange 256 (at the edge of the opening 255) in the proximal housing component 12a, and are caused to bend by the engagement with the flange 256. In an exemplary embodiment, the flange 256 provided in or adjacent to the inner surface of the housing 12a may be modified to increase the size of the opening 255.

Exemplary embodiments configure and/or modify the flange 256 to minimize engagement of the distal arms 1114 of the shroud 1110 with the flange 256. Exemplary embodiments also configure and/or modify the flange 256 to delay the engagement of the distal arms 1114 of the shroud 1110 with the flange 256 during the shroud deployment process. In this manner, exemplary embodiments maximize the extension forces generated during the shroud deployment process, and result in smooth and reliable shroud deployment. In an exemplary embodiment, the flange 256 is configured to minimize bending of the distal arms 1114 of the shroud 1110 when the arms are engaged by the flange 256. In an exemplary embodiment, a portion of the flange 256 abutting the opening 255 may be cut off or removed to provide more room for the distal arms 1114 of the shroud 1110 to slide through the flange 256 and then to catch onto a small pocket 257 in the flange 256. The pocket 257 of the flange 256 prevents further retraction of the shroud 1110.

Figure 22A:
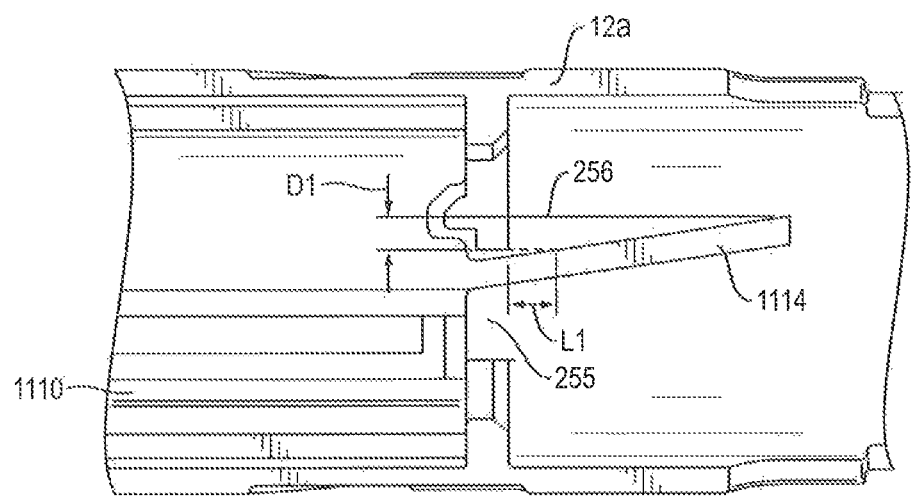
FIG. 22A is a longitudinal sectional view taken through a proximal housing component housing a shroud, in which the proximal housing component lacks a flange cut.
Figure 22B:
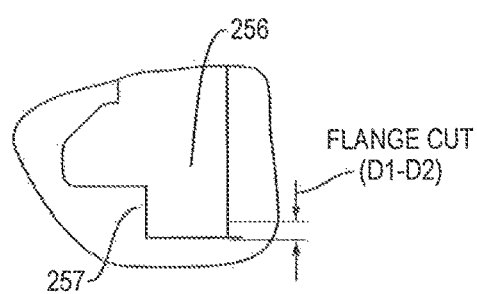
FIG. 22B is a longitudinal sectional view taken through the proximal housing component, showing the pocket on the proximal side of the flange.

FIG. 22A is a longitudinal sectional view taken through a proximal housing component 12a housing a shroud 1110, in which the proximal housing component 12a lacks a flange cut. The proximal housing component 12a includes a flange 256 with an opening 255 and a pocket 257. The flange 256 extends into the opening 255 to a greater extent, denoted as distance D1. The shroud 1110 includes distal arms 1114 that pass through the opening 255 and that are bent by the protrusion of the flange 256 into the opening 255. This bending effect occurs at an earlier time (compared to a proximal housing component with a flange cut) after the distal arm 1114 has traveled over distance L1 through the opening 255. After passing through the opening 255, the terminal end of the distal arm 1114 catches onto the pocket 257. FIG. 22B is a longitudinal sectional view taken through the proximal housing component 12a, showing the pocket 257 on the proximal side of the flange 256.

Figure 23A:
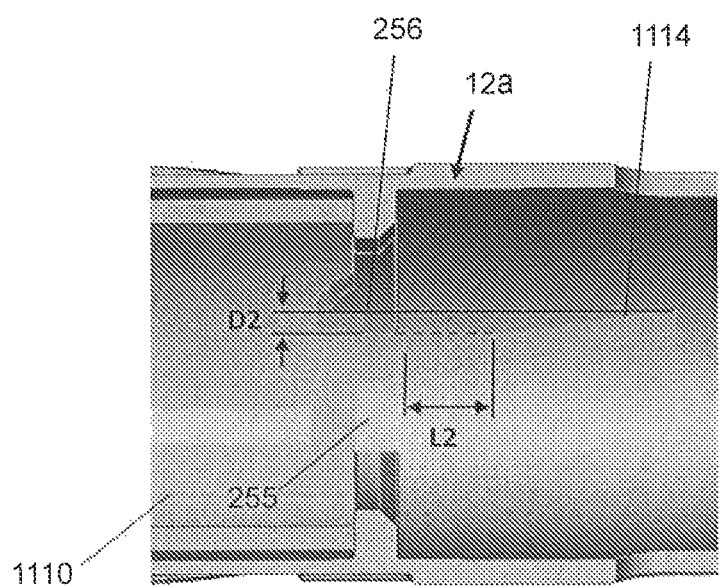
FIG. 23A is a longitudinal sectional view taken through a proximal housing component housing a shroud, in which the proximal housing component includes a flange cut.
Figure 23B:
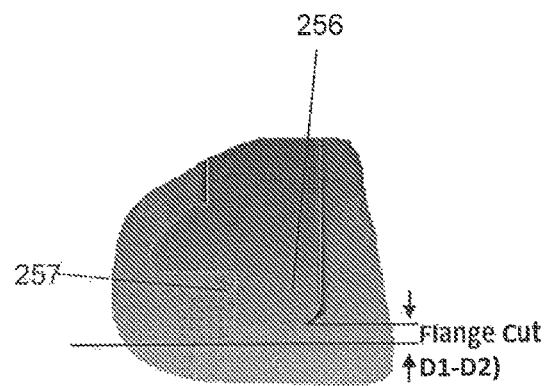
FIG. 23B is a longitudinal sectional view taken through the proximal housing component, showing the pocket on the proximal side of the flange.

FIG. 23A is a longitudinal sectional view taken through a proximal housing component 12a housing a shroud 1110, in which the proximal housing component 12a includes a flange cut. The proximal housing component 12a includes a flange 256 with an opening 255 and a pocket 257. The flange 256 extends into the opening 255 to a lesser extent, denoted as distance D2. That is, a portion along the circumferential length of the flange 256 abutting the opening 255 is removed or cut by introducing a flange cut, denoted by a length (D1-D2), so that the opening 255 is wider. The shroud 1110 includes distal arms 1114 that pass through the opening 255 and that are bent by the protrusion of the flange 256 into the opening 255. This bending effect occurs at a later time (compared to a proximal housing component without a flange cut) after the distal arm 1114 has traveled over distance L2 through the opening 255. This exemplary modification to the flange delays and reduces the engagement of the distal arms 1114 with the flange 256 to reduce the bending effect and, therefore, maximize the extension forces during shroud deployment process. After passing through the opening 255, the terminal end of the distal arm 1114 catches onto the pocket 257. FIG. 23B is a longitudinal sectional view taken through the proximal housing component 12a, showing the pocket 257 on the proximal side of the flange 256.

Exemplary cuts or notches formed in the flange 256 may range in length from between about 0 mm to about 10 mm in some exemplary embodiments. Some exemplary lengths of the cuts or notches may include, but are not limited to, about 0, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, and the like. Some exemplary lengths of the cuts or notches may range from about 0.05 mm to about 0.6 mm. In an exemplary embodiment, the opening distance between two oppositely-positioned openings 255 in the flange 256 may be abound 3.10 mm, and the span of the distal arms 1114 of the shroud 1110 (i.e., the distance between the terminal ends of the distal arms taken perpendicular to the length of the shroud) may be about 6.13 mm.

In an exemplary embodiment, one or more bosses may be added to the flange 256 to create a backstop for the distal arms 1114 of the shroud 1110 to lock into place when shroud override forces are applied in the distal direction to the shroud 1110. In an exemplary embodiment, one or more chamfers may be added to the edges of the flange 256 to facilitate its engagement with the distal arms 1114 of the shroud 1110.

Figure 24:
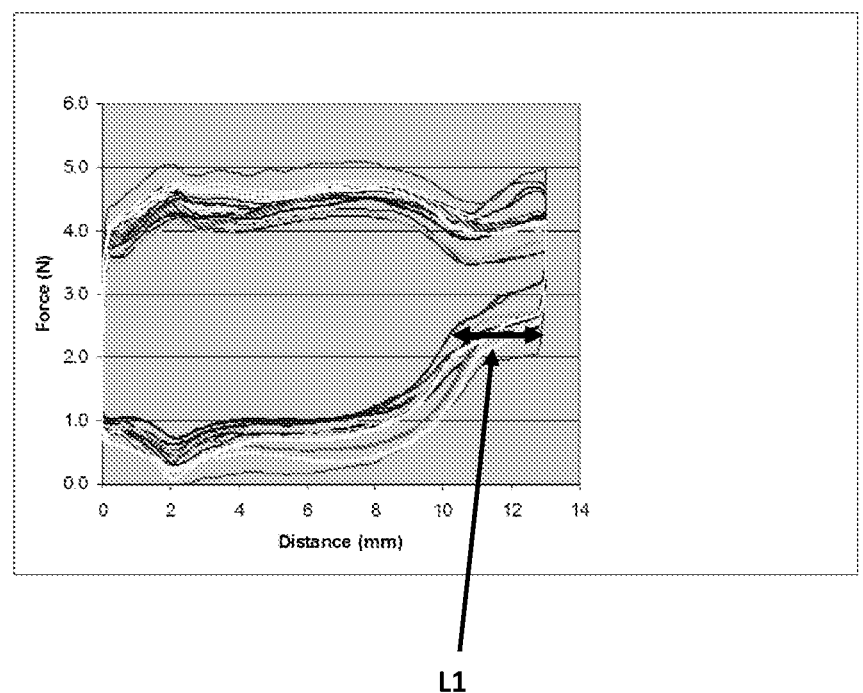
FIG. 24 illustrates a graph showing retraction and extension forces in N (y-axis) generated at different deployment distances in mm (x-axis) during shroud deployment associated with conventional automatic injection devices that are not configured to improve the shroud deployment process.

FIG. 24 illustrates a graph showing retraction and extension forces in N (y-axis) generated at different deployment distances in mm (x-axis) during shroud deployment associated with conventional automatic injection devices that are not configured to improve the shroud deployment process.

The force profile of FIG. 24 is used as a control to verify and evidence the improvements in the shroud deployment process achieved by exemplary embodiments. FIG. 24 shows a large and sudden drop in the forces generated from about 2.5 N to about 0.5 N after the shroud has traveled a distance denoted as L1. This drop in the forces corresponds to the bending effect of the distal arms 1114 of the shroud 1110 caused by engagement of the distal arms 1114 with the flange 256 in the proximal housing component 12a. Since the conventional flange does not include a flange cut, the bending effect occurs at an earlier time (compared to a proximal housing component with a flange cut) after the distal arm 1114 has traveled over distance L1 through the opening 255 in the flange 256. In the example shown in FIG. 24, the bending effect starts after the distal arm 1114 has traveled about 2 mm. Furthermore, a later pinching effect is observed at a deployment distance of about 2 mm at which a downward peak reduces the forces from about 0.8 N to about 0 N. The residual extension force at the end of the shroud deployment process is about 1 N.

Figure 25:
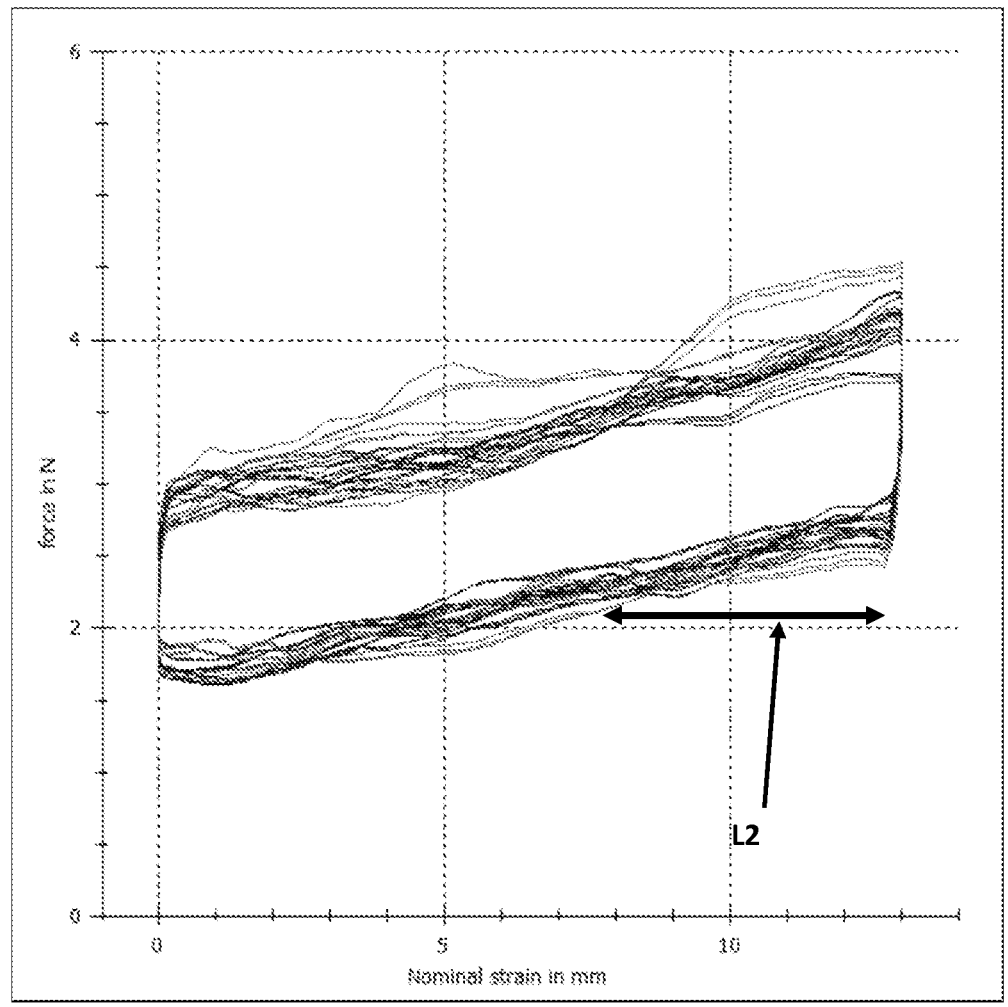
FIG. 25 illustrates a graph showing retraction and extension forces in N (y-axis) generated at different deployment distances in mm (x-axis) during shroud deployment associated with housing components with a 0.1 mm flange cut.

In some exemplary embodiments, a cutout is formed in an exemplary interior flange 256 of a proximal housing component 12a. In an exemplary embodiment, the cutout may have a dimension of about 0.1 mm FIG. 25 illustrates a graph showing retraction and extension forces in N (y-axis) generated at different deployment distances in mm (x-axis) during shroud deployment associated with housing components with a 0.1 mm flange cut. FIG. 25 shows a drop in the forces generated from about 2.5 N to about 2 N after the shroud has traveled a distance denoted as L2. This drop in the forces corresponds to the bending effect of the distal arms 1114 of the shroud 1110 caused by engagement of the distal arms 1114 with the flange 256 in the proximal housing component 12a. Since the exemplary flange includes a flange cut, the bending effect occurs at a later time (compared to a conventional proximal housing component without a flange cut) after the distal arm 1114 has traveled over a greater distance L2 through the opening in the flange 256. In the example shown in FIG. 25, the bending effect starts after the distal arm 1114 has traveled about 5 mm. In addition, the drop in the forces is more gradual and smaller in magnitude (i.e., a force difference of about 0.5 N) compared to that in FIG. 24. The residual extension force in FIG. 25 at the end of the deployment is about 1.8 N, which is higher than the residual extension force of about 1.0 N in FIG. 24. A comparison between FIGS. 24 and 25 indicates that introducing a cutout in the flange 256 reduces the bending effect on the distal arms 1114 of the shroud 1110 (i.e., the second type of interaction). This results in a later and more gradual drop in the extension forces over the deployment process and an increase in the residual extension force.

Figure 26:
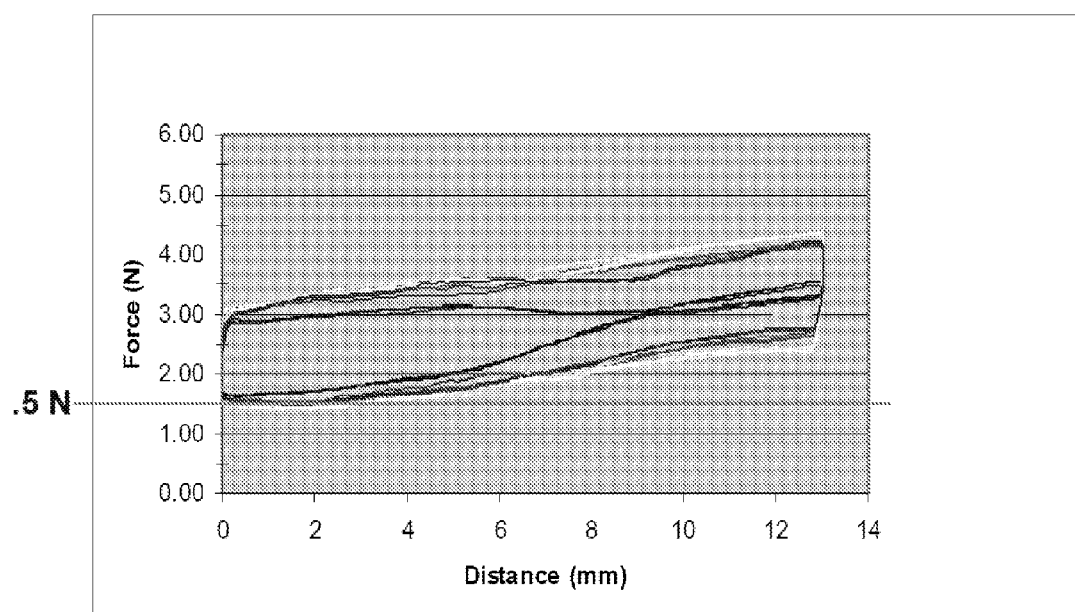
FIG. 26 illustrates a graph showing retraction and extension forces in N (y-axis) generated at different deployment distances in mm (x-axis) during shroud deployment associated with housing components with a 0.3 mm flange cut.

In some exemplary embodiments, a cutout is formed in an exemplary interior flange 256 formed of a polycarbonate material. In an exemplary embodiment, the cutout may have a dimension of about 0.3 mm FIG. 26 illustrates a graph showing retraction and extension forces in N (y-axis) generated at different deployment distances in mm (x-axis) during shroud deployment associated with housing components with a 0.3 mm flange cut. FIG. 26 shows that the extension forces do not exhibit a sharp drop, unlike in FIG. 24. That is, the downward slope in FIG. 24 is more gradual than the downward slope in FIG. 24. The residual extension force in FIG. 26 at the end of the deployment is about 1.5 N, which is higher than the residual extension force of about 1.0 N in FIG. 24. A comparison between FIGS. 24 and 26 indicates that introducing a cutout in the flange 256 reduces the bending effect on the distal arms 1114 of the shroud 1110 (i.e., the second type of interaction). This results in a later and more gradual drop in the extension forces over the deployment process and an increase in the residual extension force.

Figure 27:
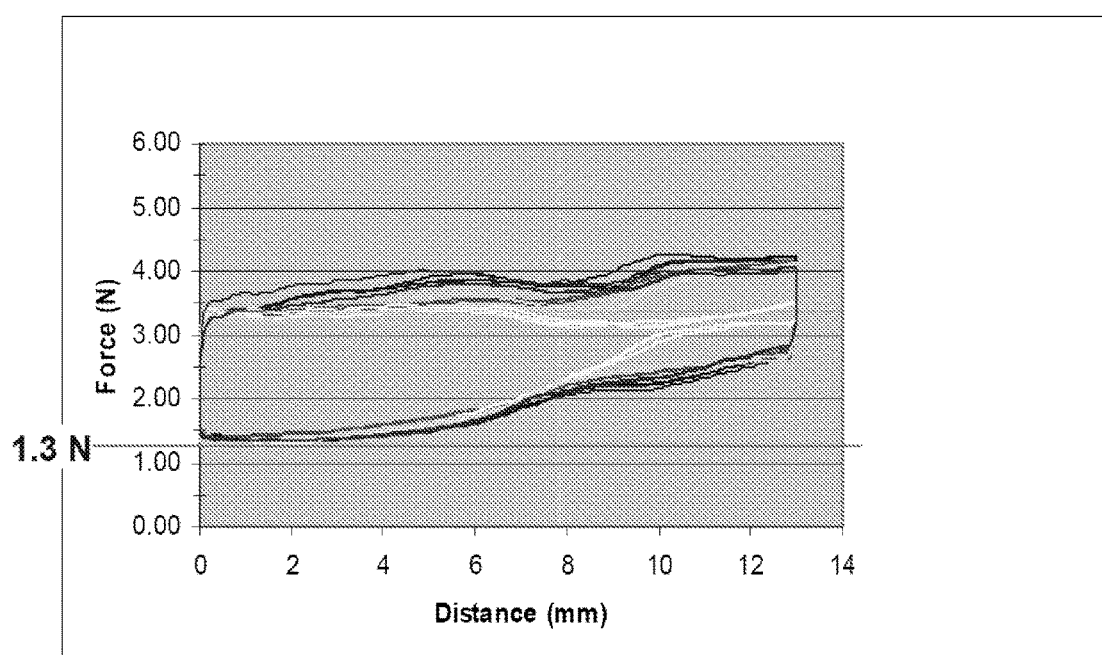
FIG. 27 illustrates a graph showing retraction and extension forces in N (y-axis) generated at different deployment distances in mm (x-axis) during shroud deployment associated with housing components with a 0.3 mm flange cut.

In some exemplary embodiments, a cutout is formed in an exemplary interior flange 256 formed of a polypropylene material. In an exemplary embodiment, the cutout may have a dimension of about 0.3 mm FIG. 27 illustrates a graph showing retraction and extension forces in N (y-axis) generated at different deployment distances in mm (x-axis) during shroud deployment associated with housing components with a 0.3 mm flange cut. FIG. 27 shows that the extension forces do not exhibit a sharp drop, unlike in FIG. 24. That is, the downward slope in FIG. 27 is more gradual than the downward slope in FIG. 24. This is due to the design change in the distal arms, which reduces the bending effect of the distal arms during the early stages of the shroud deployment process. The residual extension force in FIG. 27 at the end of the deployment is about 1.3 N, which is higher than the residual extension force of about 1.0 N in FIG. 24. A comparison between FIGS. 24 and 27 indicates that introducing a cutout in the flange 256 reduces the bending effect on the distal arms 1114 of the shroud 1110 (i.e., the second type of interaction). This results in a later and more gradual drop in the extension forces over the deployment process and an increase in the residual extension force.

C. Configuration of the Proximal Tubular Portion of the Syringe Carrier

In an exemplary embodiment, the constrained space between the syringe carrier 1000 and the proximal housing component 12*a* may be increased to reduce the pinching effect on the distal arms 1114 of the shroud 1110 and to, thereby, maximize the extension forces in a later stage in the shroud deployment process, while ensuring proper lockout of the shroud in the extended position. In an exemplary embodiment, the outer diameter of the proximal tubular portion 1002 of the syringe carrier 1000 may be decreased in order to increase the constrained space between the syringe carrier 1000 and the proximal housing component 12*a*, which provides a larger space for the twisting movement of the distal arms 1114 of the shroud 1110 and facilitates smooth and reliable shroud deployment.

Exemplary outer diameters of the proximal tubular portion 1002 of the syringe carrier 1000 may range from about 13.00 mm to about 15.00 mm, but are not limited to this exemplary range. An exemplary outer diameter of the proximal tubular portion 1002 of the syringe carrier 1000 may be about 13.17 mm, 14.00 mm, 14.17 mm, and the like. In an exemplary embodiment, the distal arms 1114 (accommodated within the constrained space between the proximal tubular portion of the syringe carrier and the proximal housing component 12*a*) may have a thickness of about 1.40 mm to about 1.45 mm and may have an inner diameter of about 14.40 mm. The proximal housing component 12*a* may have an exemplary inner diameter of about 17.60 mm.

Figure 28A:
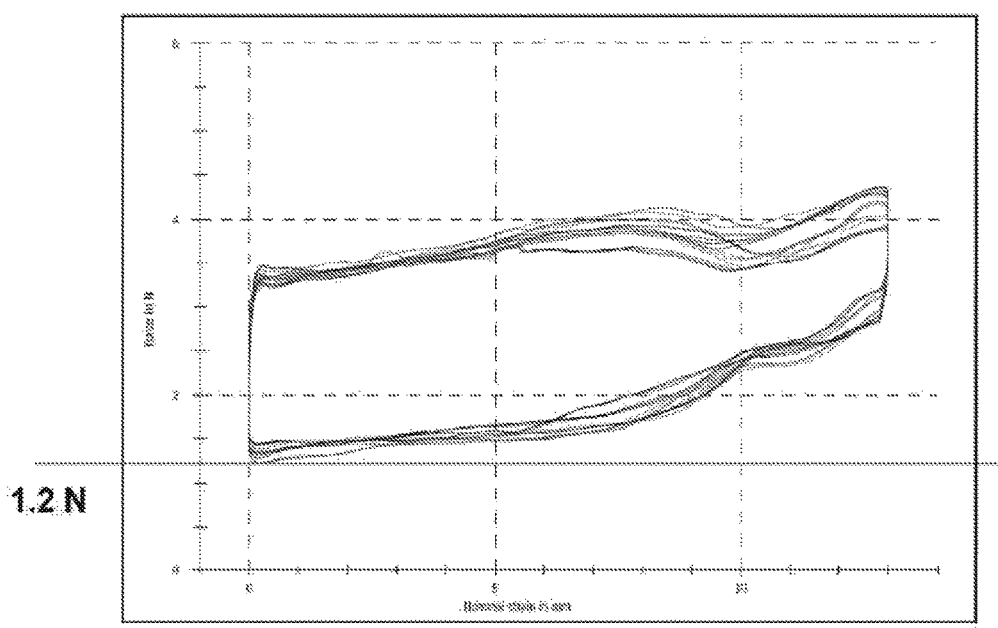
FIG. 28A illustrates a graph plotting retraction and extension forces in N (y-axis) generated at different deployment distances in mm (x-axis), for an exemplary syringe carrier with a proximal tubular portion that has been reduced in outer diameter from about 14.17 mm to about 13.17 mm.

FIG. 28A illustrates a graph plotting retraction and extension forces in N (y-axis) generated at different deployment distances in mm (x-axis), for an exemplary syringe carrier 1000 with a proximal tubular portion 1002 that has been reduced in outer diameter from about 14.17 mm to about 13.17 mm FIG. 28A shows that the extension force does not include a downward peak in a later stage in the shroud deployment process, e.g., at an x-axis range of between about 4 mm and about 1 mm, unlike in FIG. 24. FIG. 28A also shows that the residual extension force at the end of the deployment is about 1.2 N for the 13.17 mm outer diameter, which is higher than residual extension forces of about 0.5 N to about 1.0 N for the 14.17 mm outer diameter.

Figure 28B:
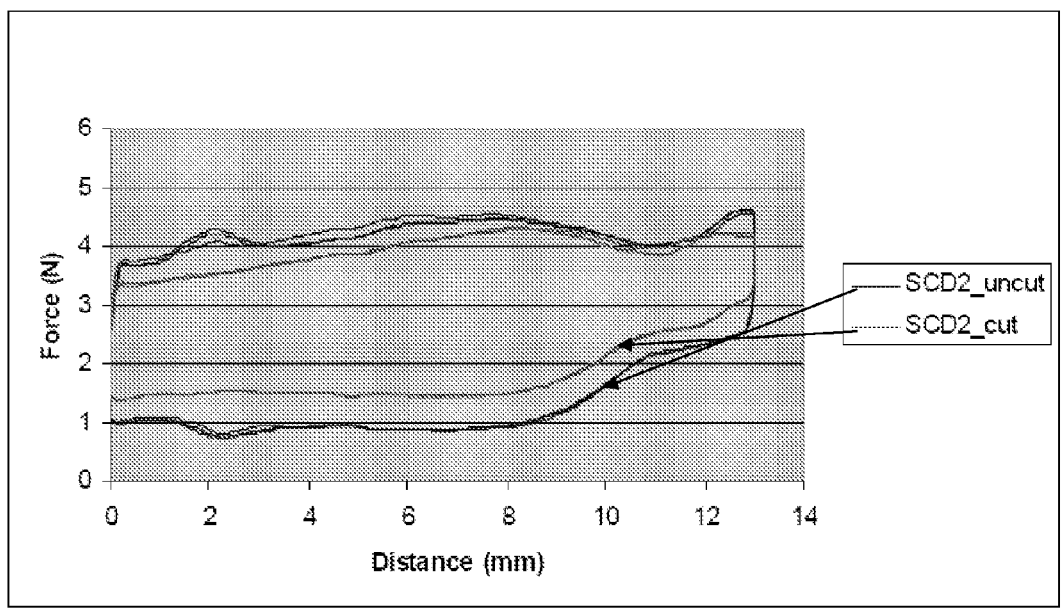
FIG. 28B illustrates a graph plotting retraction and extension forces in N (y-axis) generated at different deployment distances in mm (x-axis), for an exemplary syringe carrier with a proximal tubular portion that has been reduced in outer diameter from about 14.17 mm to about 14.00 mm.

FIG. 28B illustrates a graph plotting retraction and extension forces in N (y-axis) generated at different deployment distances in mm (x-axis), for an exemplary syringe carrier 1000 with a proximal tubular portion 1002 that has been reduced in outer diameter from about 14.17 mm to about 14.00 mm FIG. 28B shows that the extension force does not include a downward peak in a later stage in the shroud deployment process, e.g., at an x-axis range of between about 4 mm and about 1 mm, unlike in FIG. 24. FIG. 28B also shows that the residual extension force at the end of the deployment is above 1 N for the 14.00 mm outer diameter, which is higher than residual extension forces of about 0.5 N to about 1.0 N for the 14.17 mm outer diameter.

D. Configuration of the Inner Diameter of the Proximal Housing Component

In an exemplary embodiment, the constrained space between the syringe carrier 1000 and the proximal housing component 12*a* may be increased to reduce the bending effect and/or the pinching effect and to, thereby, maximize the extension forces in the during the shroud deployment process, while ensuring proper lockout of the shroud in the extended position. The inner diameter of the proximal housing component 12*a* of the automatic injection device may be increased in order to increase the constrained space between the syringe carrier 1000 and the proximal housing component 12*a*, which provides a larger space for the twisting movement of the distal arms 1114 of the shroud 1110, which provides a larger space for the twisting movement of the distal arms 1114 of the shroud 1110 and facilitates smooth and reliable shroud deployment.

Exemplary inner diameters of the proximal housing component 12*a* may range from about 17 mm to about 18 mm, but are not limited to this exemplary range. An exemplary range of inner diameters is between about 17.5 mm and about 17.7 mm for a proximal housing component formed of a repsol-grade polypropylene material. An exemplary range of inner diameters is between about 17.7 mm and about 17.85 mm for a proximal housing component formed of a polycarbonate material.

At the same time, the exemplary embodiments may impose a maximum limit on the inner diameter of the proximal housing component 12*a*, because inner diameters above the limit may create syringe alignment problems within the housing of the automatic injection device. Thus, a problem solved by exemplary embodiments is increasing the inner diameter of the proximal housing component 12*a* within a certain maximum limit in order to improve the shroud deployment process, while limiting the outer and inner diameters of the automatic injection device and avoiding syringe alignment problems.

In an exemplary embodiment, the distal arms 1114 (accommodated within the constrained space between the proximal tubular portion of the syringe carrier and the proximal housing component 12*a*) may have a thickness of about 1.40 mm to about 1.45 mm and may have an inner diameter of about 14.40 mm. An exemplary outer diameter of the proximal tubular portion 1002 of the syringe carrier 1000 may be about 13.17 mm, 14.00 mm, 14.17 mm, and the like. The proximal housing component 12*a* may have an exemplary inner diameter of about 17 mm to about 18 mm.

Figure 29:
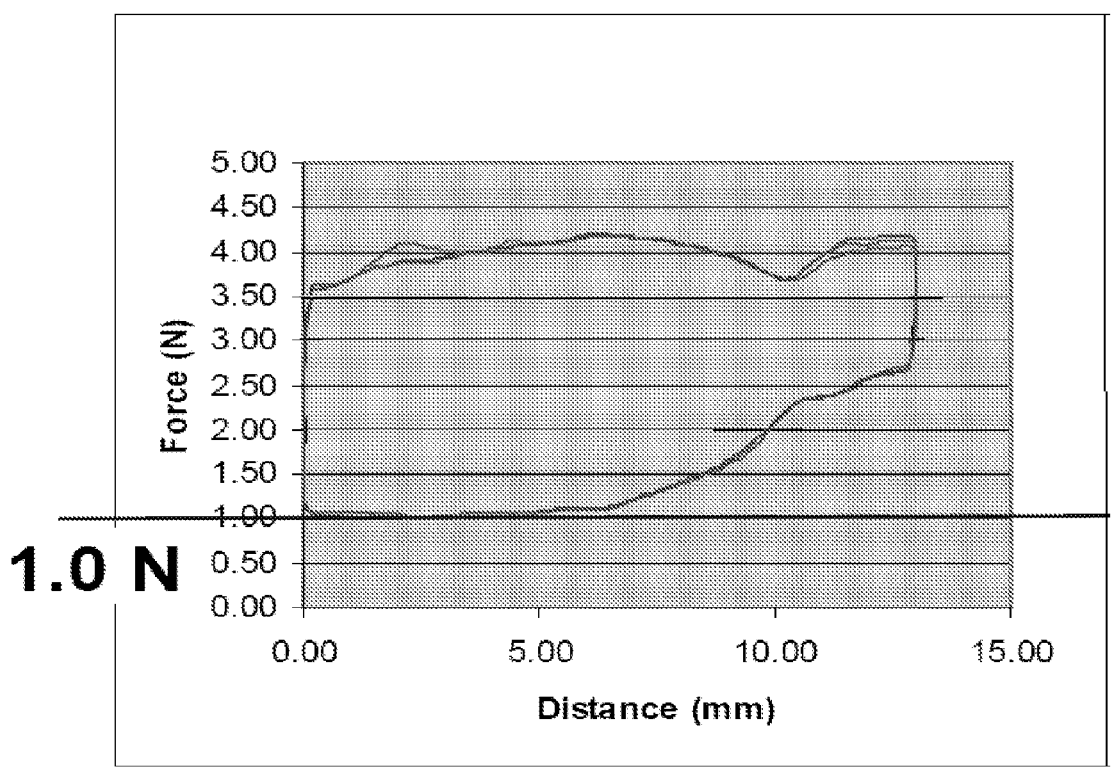
FIG. 29 illustrates a graph showing retraction and extension forces in N (y-axis) generated at different deployment distances in mm (x-axis) for a control proximal housing component formed of a repsol-grade polypropylene material with an inner diameter of about 17.53 mm to about 17.63 mm.

FIG. 29 illustrates a graph showing retraction and extension forces in N (y-axis) generated at different deployment distances in mm (x-axis) for a control proximal housing component formed of a repsol-grade polypropylene material with an inner diameter of about 17.53 mm to about 17.63 mm FIG. 29 shows that the residual extension force at the end of the deployment is about 1.0 N.

Figure 30:
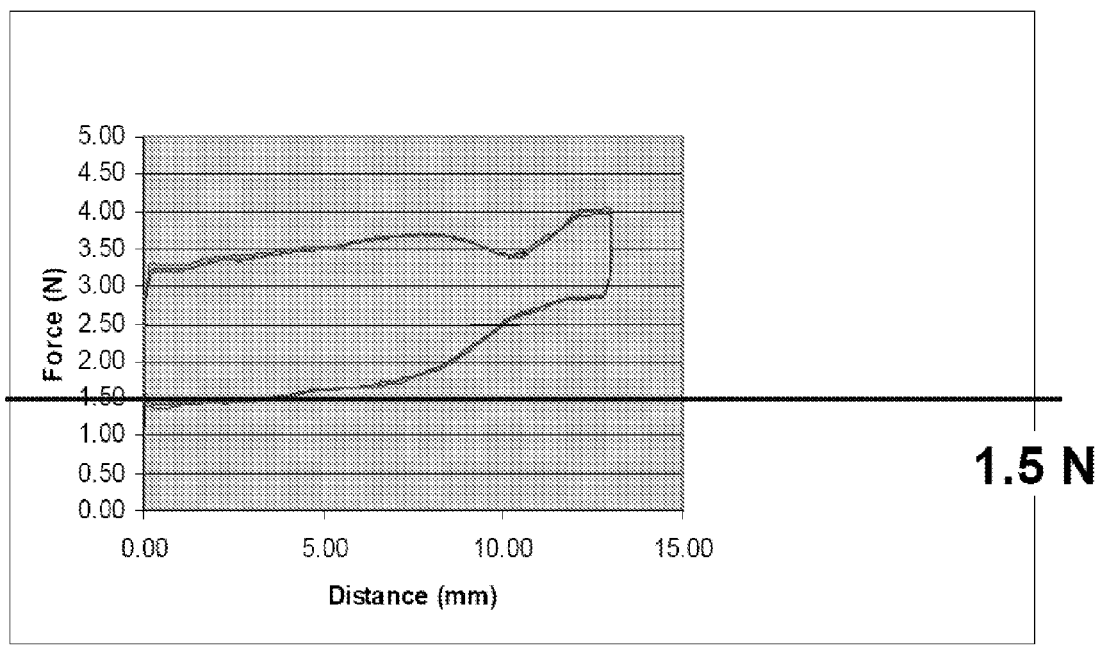
FIG. 30 illustrates a graph showing retraction and extension forces in N (y-axis) generated at different deployment distances in mm (x-axis) for an exemplary test proximal housing component formed of a polycarbonate material with an increased inner diameter of about 17.72 mm to about 17.85 mm.

FIG. 30 illustrates a graph showing retraction and extension forces in N (y-axis) generated at different deployment distances in mm (x-axis) for an exemplary test proximal housing component formed of a polycarbonate material with an increased inner diameter of about 17.72 mm to about 17.85 mm FIG. 30 shows that the residual extension force at the end of the shroud deployment process is about 1.5 N, which is advantageously higher than for the control proximal housing component of FIG. 29.

A comparison between FIGS. 29 and 30 shows that increasing the inner diameter of the proximal housing component 12a reduces the pinching effect of the distal arms of the shroud, which maximizes the extension forces during a later stage of the shroud deployment process. That is, the proximal housing component 12a corresponding to FIG. 30 results in significant improvements in the shroud deployment and lockout performance.

E. Other Exemplary Configurations of the Transition Portion of the Syringe Carrier In an exemplary embodiment, the transition portion of the syringe carrier 2100 may be configured to reduce the pinching effect and to, thereby, maximize the extension forces in a later stage in the shroud deployment process. In an exemplary embodiment, a gradual transition, i.e., a sloped portion, may be introduced at the transition portion to provide a gradual transition between the wider proximal tubular portion 2104 and the narrower distal tubular portion 2106, and to thereby reduce the outer diameter of the proximal tubular portion 2104 at the critical pinching area of the transition portion. This provides a larger space for the twisting movement of the distal arms 1114 of the shroud 1110 and facilitates smooth and reliable shroud deployment. The gradual transition between the proximal and distal tubular portions of the syringe carrier may take the form of a chamfer in an exemplary embodiment. An exemplary chamfer may fully or partially replace a step at the transition portion of the syringe carrier.

An exemplary chamfer may have an angle relative to the longitudinal axis of the automatic injection device of between about 5 degrees and about 60 degrees, although the angle is not limited to this exemplary range. Certain exemplary angles include, but are not limited to, about 5, 10, 15, 20, 25, 30, 35, 40, 45, 50, 55, 60 degrees, and the like. An exemplary chamfer may have an exemplary width of between about 0.2 mm and about 0.7 mm, although the width is not limited to this exemplary range. Exemplary widths may include, but are not limited to, about 0.2, 0.25, 0.3, 0.35, 0.4, 0.45, 0.5, 0.55, 0.6, 0.65, 0.7 mm, and the like. An exemplary chamfer may have an exemplary depth (i.e., the vertical distance between the proximal tubular portion and the distal tubular portion) of between about 0.6 mm and about 0.9 mm, although the depth is not limited to this exemplary range. Certain exemplary depths may include, but are not limited to, about 0.6, 0.65, 0.7, 0.75, 0.8, 0.85, 0.9 mm, and the like. An exemplary chamfer may have an exemplary length ranging between about 0.1 mm and about 0.5 mm, but is not limited to this exemplary range. Exemplary lengths may include, but are not limited to, about 0.1, 0.15, 0.2, 0.25, 0.3, 0.35, 0.4, 0.45, 0.5 mm, and the like.

In an exemplary embodiment, the edge of the transition portion of the syringe carrier 2100 may include a rounded structure. An exemplary rounded structure may have an exemplary width of between about 0.1 mm and about 0.7 mm, although the width is not limited to this exemplary range.

Figure 31A:
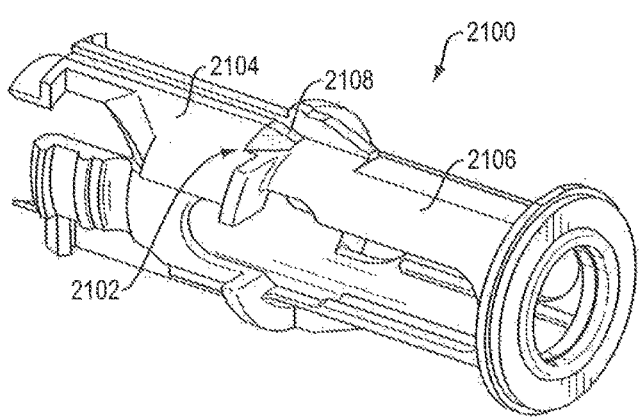
FIG. 31A illustrates a perspective view of an exemplary syringe carrier having an exemplary chamfer formed between the proximal tubular portion and the distal tubular portion.
Figure 31B:
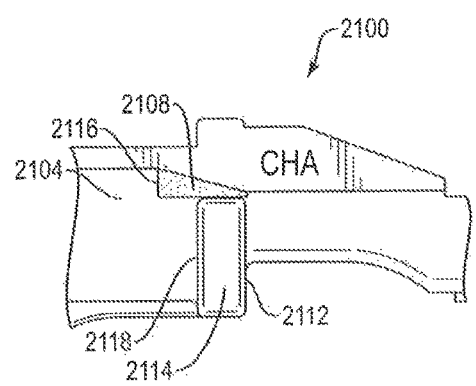
FIG. 31B illustrates a side view of the exemplary syringe carrier of FIG. 31A.

FIG. 31A illustrates a perspective view of an exemplary syringe carrier 2100 having an exemplary chamfer 2108 formed between the proximal tubular portion 2104 and the distal tubular portion 2106. FIG. 31B illustrates a side view of the exemplary syringe carrier 2100 of FIG. 31A. In the exemplary embodiment shown in FIGS. 31A and 31B, a chamfer 2108 is introduced at the transition portion 2102 so that the chamfer 2108 creates an angled relief extending between the wider proximal tubular portion 2104 and the narrower distal tubular portion 2106. The chamfer 2108 may have an exemplary width of about 0.7 mm, an exemplary length of about 3 mm, and an exemplary angle of about 15 degrees relative to the plane of the cylindrical portions. In the exemplary embodiment shown in FIGS. 31A and 31B, the distal edge 2110 of the chamfer 2108 may be aligned with the distal edge 2112 of the flange 2114 of the transition portion 2102, and the proximal edge 2116 of the chamfer 2108 may extend in the proximal direction beyond the proximal edge 2118 of the flange 2114. In another exemplary embodiment, the distal edge 2110 of the chamfer 2108 may not be aligned with the distal edge 2112 of the flange 2114 of the transition portion 2102.

Figure 32:
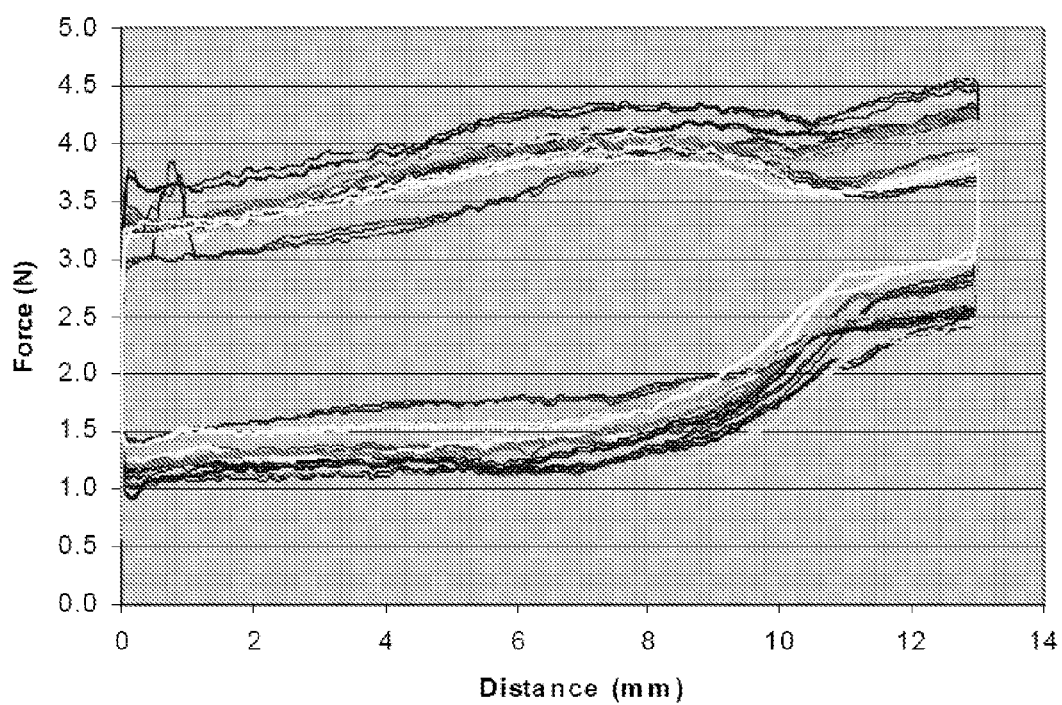
FIG. 32 illustrates a graph of retraction and extension forces in N (y-axis) against shroud deployment distances in mm (x-axis) in automatic injection devices including ten exemplary syringe carriers configured as shown in FIGS. 31A and 31B.

FIG. 32 illustrates a graph of retraction and extension forces in N (y-axis) against shroud deployment distances in mm (x-axis) in automatic injection devices including ten exemplary syringe carriers configured as shown in FIGS. 31A and 31B. FIG. 32 shows that the pinching effect between about 1.0 mm and about 4.0 mm shown in FIG. 24 is reduced or eliminated by the introduction of the chamfer as shown in FIGS. 31A and 31B. The residual extension force is about 1.5 N.

Figures 33A, 33B:
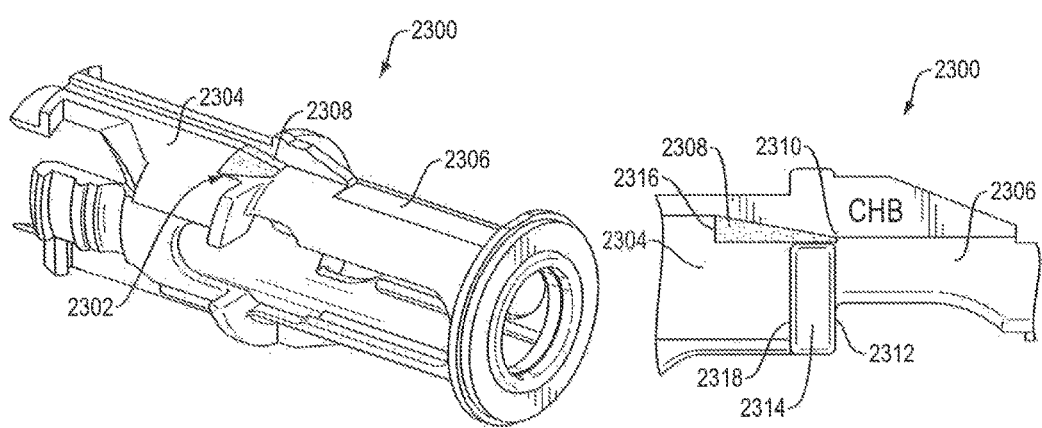
FIG. 33A illustrates a perspective view of an exemplary syringe carrier having an exemplary chamfer formed between the proximal tubular portion and the distal tubular portion.
FIG. 33B illustrates a side view of the exemplary syringe carrier of FIG. 33A.

FIG. 33A illustrates a perspective view of an exemplary syringe carrier 2300 having an exemplary chamfer 2308 formed between the proximal tubular portion 2304 and the distal tubular portion 2306. FIG. 33B illustrates a side view of the exemplary syringe carrier 2300 of FIG. 33A. In the exemplary embodiment shown in FIGS. 33A and 33B, a chamfer 2308 is introduced at the transition portion 2302 between the proximal tubular portion 2304 and the distal tubular portion 2306, so that the chamfer creates an angled relief extending between the wider proximal tubular portion 2304 and the narrower distal tubular portion 2306. The chamfer 2308 may have an exemplary width of about 0.7 mm and an exemplary angle of about 10 degrees relative to the plane of the cylindrical portions. In the exemplary embodiment shown in FIGS. 33A and 33B, the distal edge 2310 of the chamfer 2308 may be aligned with the distal edge 2312 of the flange 2314, and the proximal edge 2316 of the chamfer 2308 may extend in the proximal direction beyond the proximal edge 2318 of the flange 2314.

Figure 34:
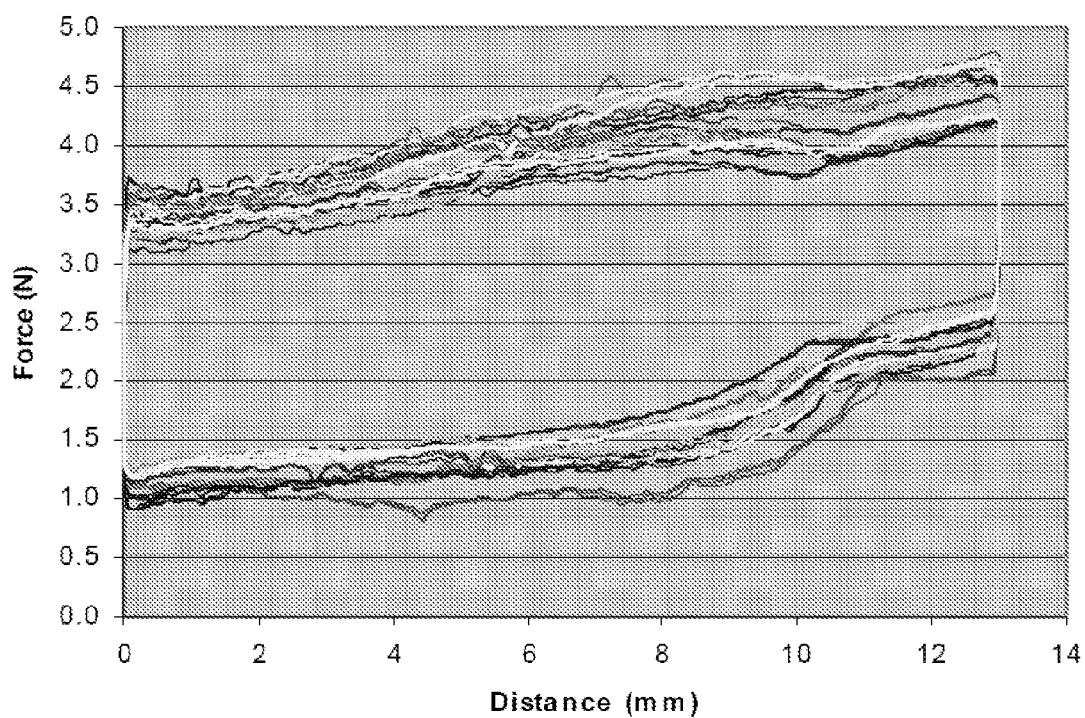
FIG. 34 illustrates a graph of retraction and extension forces in N (y-axis) against shroud deployment distances in mm (x-axis) in exemplary automatic injection devices including ten exemplary syringe carriers configured as shown in FIGS. 33A and 33B.

FIG. 34 illustrates a graph of retraction and extension forces in N (y-axis) against shroud deployment distances in mm (x-axis) in exemplary automatic injection devices including ten exemplary syringe carriers configured as shown in FIGS. 33A and 33B. FIG. 34 shows that the pinching effect at about 2.5 mm shown in FIG. 24 is eliminated by the introduction of the chamfer as shown in FIGS. 33A and 33B. In addition, the residual extension force is raised to above 1.0 N by the introduction of the chamfer as shown in FIGS. 33A and 33B.

Figure 35A:
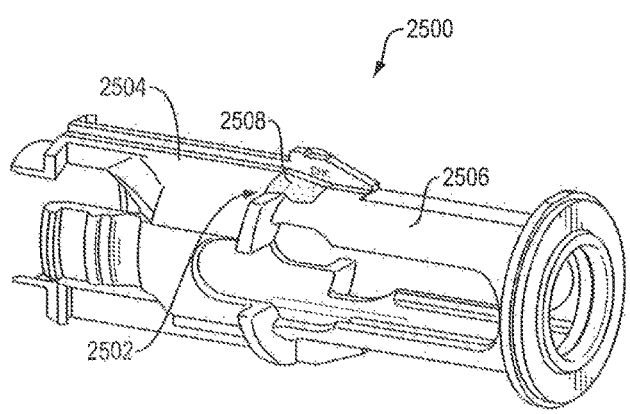
FIG. 35A illustrates a perspective view of an exemplary syringe carrier having an exemplary chamfer formed between the proximal tubular portion and the distal tubular portion.
Figure 35B:
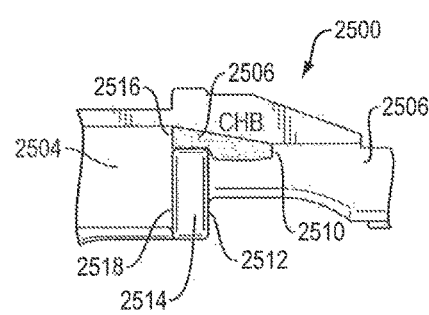
FIG. 35B illustrates a side view of the exemplary syringe carrier of FIG. 35A.

FIG. 35A illustrates a perspective view of an exemplary syringe carrier 2500 having an exemplary chamfer 2508 formed between the proximal tubular portion 2504 and the distal tubular portion 2506. FIG. 35B illustrates a side view of the exemplary syringe carrier 2500 of FIG. 35A. In the exemplary embodiment shown in FIGS. 35A and 35B, a chamfer 2508 is introduced at the transition portion 2502 between the proximal tubular portion 2504 and the distal tubular portion 2506, so that the chamfer 2508 creates an angled relief extending between the wider proximal tubular portion 2504 and the narrower distal tubular portion 2506. The chamfer 2508 may have an exemplary width of about 0.7 mm and an exemplary angle of about 10 degrees relative to the plane of the cylindrical portions. In the exemplary embodiment shown in FIGS. 35A and 35B, the proximal edge 2516 of the chamfer 2508 may be aligned with the proximal edge 2518 of the flange 2514, and the distal edge 2510 of the chamfer 2508 may extend in the distal direction beyond the distal edge 2512 of the flange 2514.

Figure 36:
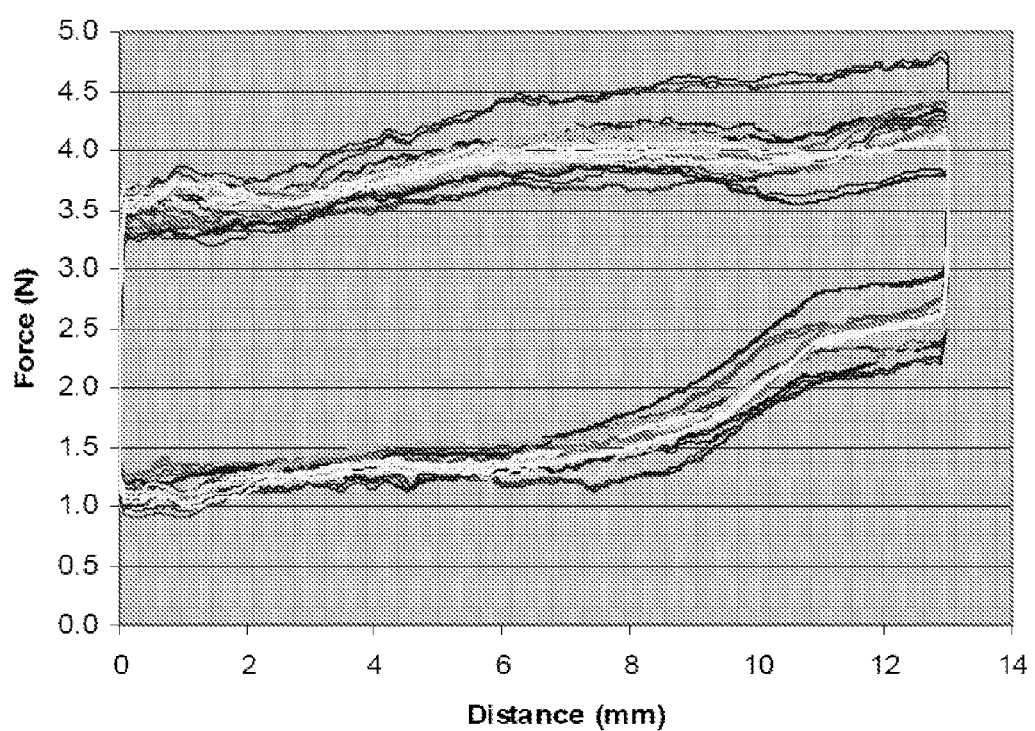
FIG. 36 illustrates a graph of retraction and extension forces in N (y-axis) against shroud deployment distances in mm (x-axis) in exemplary automatic injection devices including ten exemplary syringe carriers configured as shown in FIGS. 35A and 35B.

FIG. 36 illustrates a graph of retraction and extension forces in N (y-axis) against shroud deployment distances in mm (x-axis) in exemplary automatic injection devices including ten exemplary syringe carriers configured as shown in FIGS. 35A and 35B. FIG. 36 shows that the pinching effect at about 2.5 mm shown in FIG. 24 is eliminated by the introduction of the chamfer as shown in FIGS. 35A and 35B. In addition, the residual extension force is raised above 1.0 N by the introduction of the chamfer as shown in FIGS. 35A and 35B.

Figure 37:
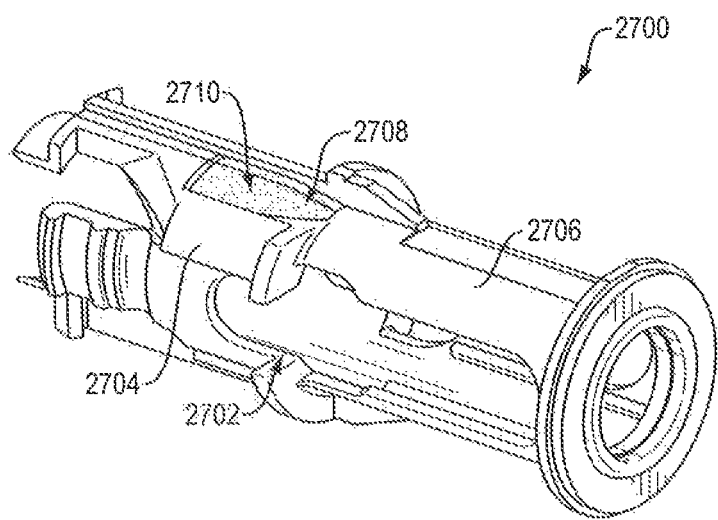
FIG. 37 illustrates a perspective view of an exemplary syringe carrier 2700 having an exemplary chamfer formed between the proximal tubular portion and the distal tubular portion and an exemplary slot formed in the proximal tubular portion.

FIG. 37 illustrates a perspective view of an exemplary syringe carrier 2700 having an exemplary chamfer 2708 formed between the proximal tubular portion 2704 and the distal tubular portion 2706 and an exemplary slot 2710 formed in the proximal tubular portion 2704. The slot 2710 is formed in the proximal tubular portion 2704 to create a depression or trench in the outer surface of the proximal tubular portion 2704. The slot 2710 may extend over a portion of the length of the proximal tubular portion 2704 or over the entire length of the proximal tubular portion 2704. During the shroud deployment process, the distal arms 1114 of the shroud 1110 may engage with the surface of the slot 2710 as the distal arms move in the proximal direction over the proximal tubular portion 2704. Introduction of the slot 2710 thus increases the constrained space between the syringe carrier 2700 and the proximal housing component 12a available to accommodate the distal arms 1114 of the shroud 1110. This reduces the pinching effect of the distal arms 1114 (i.e., the third type of interaction described above), thereby maximizing extension forces generated during the shroud deployment process and facilitating smooth and reliable shroud deployment.

Exemplary slots may have depths ranging from about 0.05 mm to about 0.5 mm, but are not limited to this exemplary range. Certain exemplary depths include, but are not limited to, about 0.05, 0.1, 0.15, 0.2, 0.25, 0.3, 0.35, 0.4, 0.45, 0.5 mm, and the like. The depth of a slot 2710 may be constant or may vary over the length and/or width of the slot. The width of the slot 2710 may be constant along its length or may vary.

In an exemplary syringe carrier including one or more slots, a chamfer may be absent at the transition portion between the proximal and distal tubular portions of the syringe carrier.

In another exemplary syringe carrier include one or more slots, a chamfer may be introduced at the transition portion between the proximal and distal tubular portions of the syringe carrier. In an exemplary embodiment, a chamfer 2708 is introduced at the transition portion 2702 so that the chamfer creates an angled relief extending between the slot 2710 and the distal tubular portion 2706. In an exemplary embodiment, the chamfer 2708 may have an exemplary width of about 0.7 mm and an exemplary angle of about 10 degrees relative to the plane of the cylindrical portions.

Figure 38:
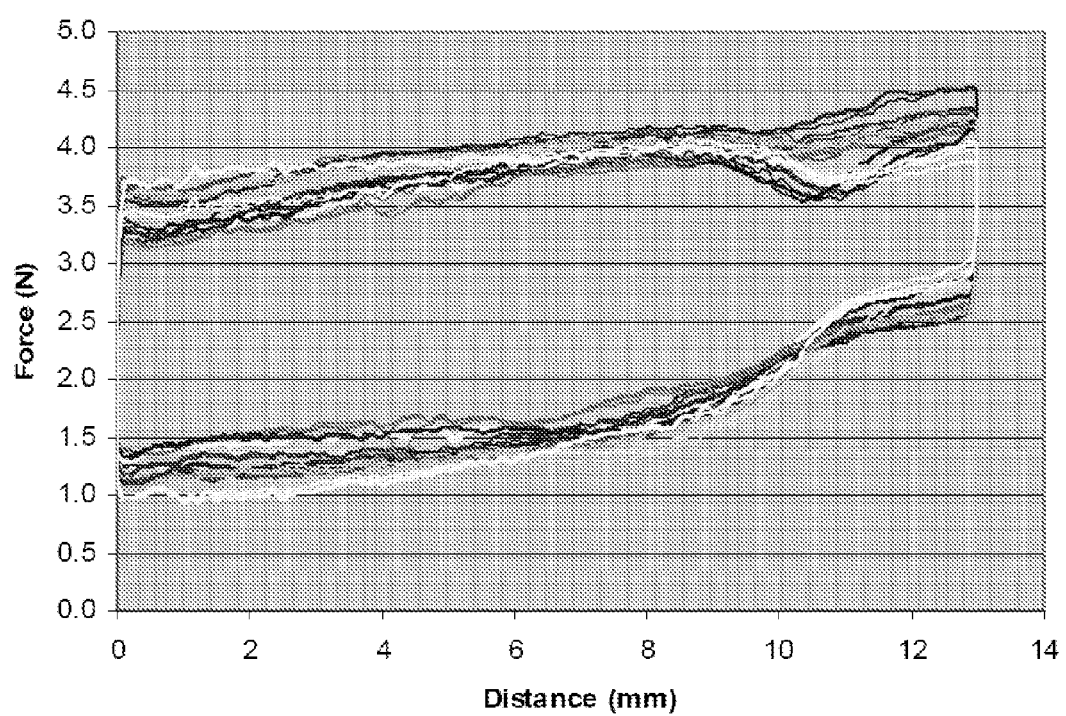
FIG. 38 illustrates a graph of retraction and extension forces in N (y-axis) against shroud deployment distances in mm (x-axis) in exemplary automatic injection devices including ten exemplary syringe carriers configured as shown in FIG. 37.

FIG. 38 illustrates a graph of retraction and extension forces in N (y-axis) against shroud deployment distances in mm (x-axis) in exemplary automatic injection devices including ten exemplary syringe carriers configured as shown in FIG. 37. A slot having a depth of about 0.1 mm and a chamfer having an exemplary width of about 0.7 mm and an exemplary angle of about 10 degrees are introduced in the syringe carriers. The introduction of the chamfer and the slot reduces the pinching effect at about 2.5 mm and increases the residual extension force above 1.0 N.

Figure 39:
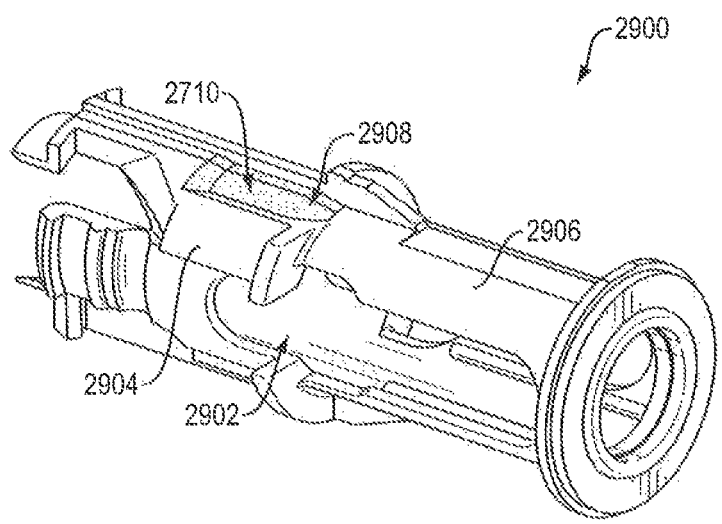
FIG. 39 illustrates a perspective view of an exemplary syringe carrier 2900 having an exemplary chamfer formed between the proximal tubular portion and the distal tubular portion and an exemplary slot formed in the proximal tubular portion.

FIG. 39 illustrates a perspective view of an exemplary syringe carrier 2900 having an exemplary chamfer 2908 formed between the proximal tubular portion 2904 and the distal tubular portion 2906 and an exemplary slot 2910 formed in the proximal tubular portion 2904. A slot 2910 is formed in the proximal tubular portion 2904 to create a depression in the surface of the proximal tubular portion. The slot 2910 may extend over a portion of the length of the proximal tubular portion 2904 or over the entire length of the proximal tubular portion 2904. During the shroud deployment process, the distal arms 1114 of the shroud 1110 may engage with the surface of the slot 2910 as the distal arms move in the proximal direction over the proximal tubular portion 2904. The slot 2910 may have an exemplary depth of about 0.3 mm.

A chamfer 2908 is introduced at the transition portion 2902 so that the chamfer creates an angled relief extending between the slot 2910 and the distal tubular portion 2906. The chamfer 2908 may have an exemplary width of about 0.7 mm and an exemplary angle of about 10 degrees relative to the plane of the cylindrical portions.

Figure 40:
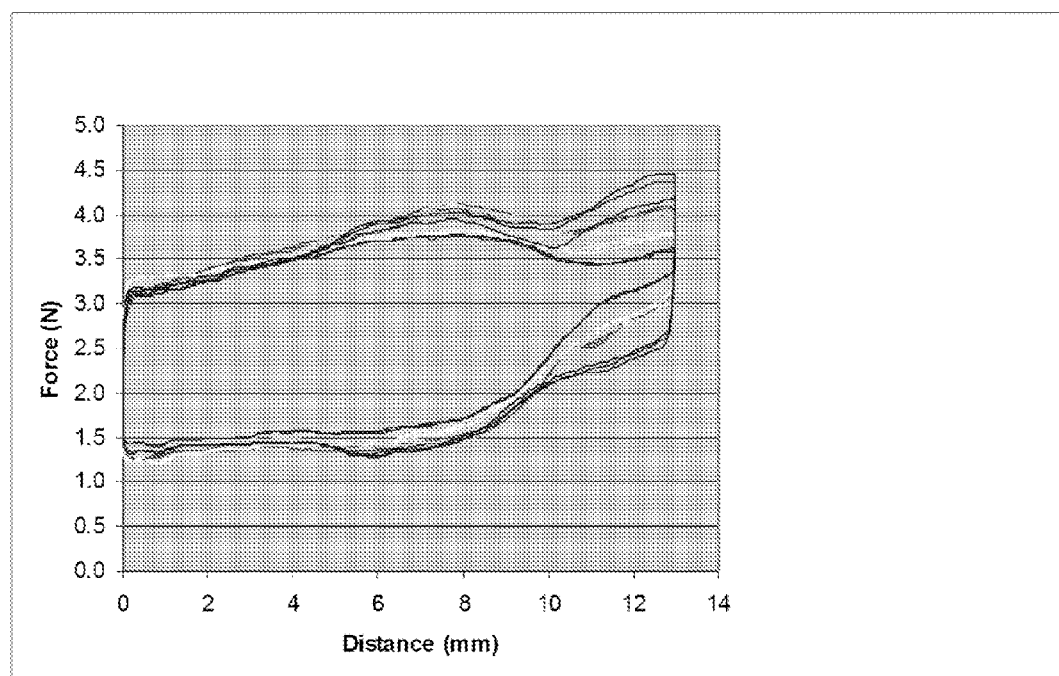
FIG. 40 illustrates a graph of retraction and extension forces in N (y-axis) against shroud deployment distances in mm (x-axis) in exemplary automatic injection devices including ten exemplary syringe carriers configured as shown in FIG. 39.

FIG. 40 illustrates a graph of retraction and extension forces in N (y-axis) against shroud deployment distances in mm (x-axis) in exemplary automatic injection devices including ten exemplary syringe carriers configured as shown in FIG. 39. A slot having a depth of about 0.3 mm is introduced in the syringe carriers. The forces generated drop at a deployment distance of about 11 mm due to the bending effect of the distal arms of the shroud. However, the introduction of the slot reduces the pinching effect over the deployment distance range of about 4 mm to about 0 mm (i.e., there is no downward peak in the forces), and raises the residual extension force to about 1.5 N. A comparison between FIGS. 24 and 40 indicates that introducing a slot in the proximal tubular component of the syringe carrier reduces the pinching effect on the distal arms 1114 of the shroud 1110 (i.e., the third type of interaction). This results in increased forces during the later stages of the shroud deployment process and an increase in the residual extension force.

Figure 41:
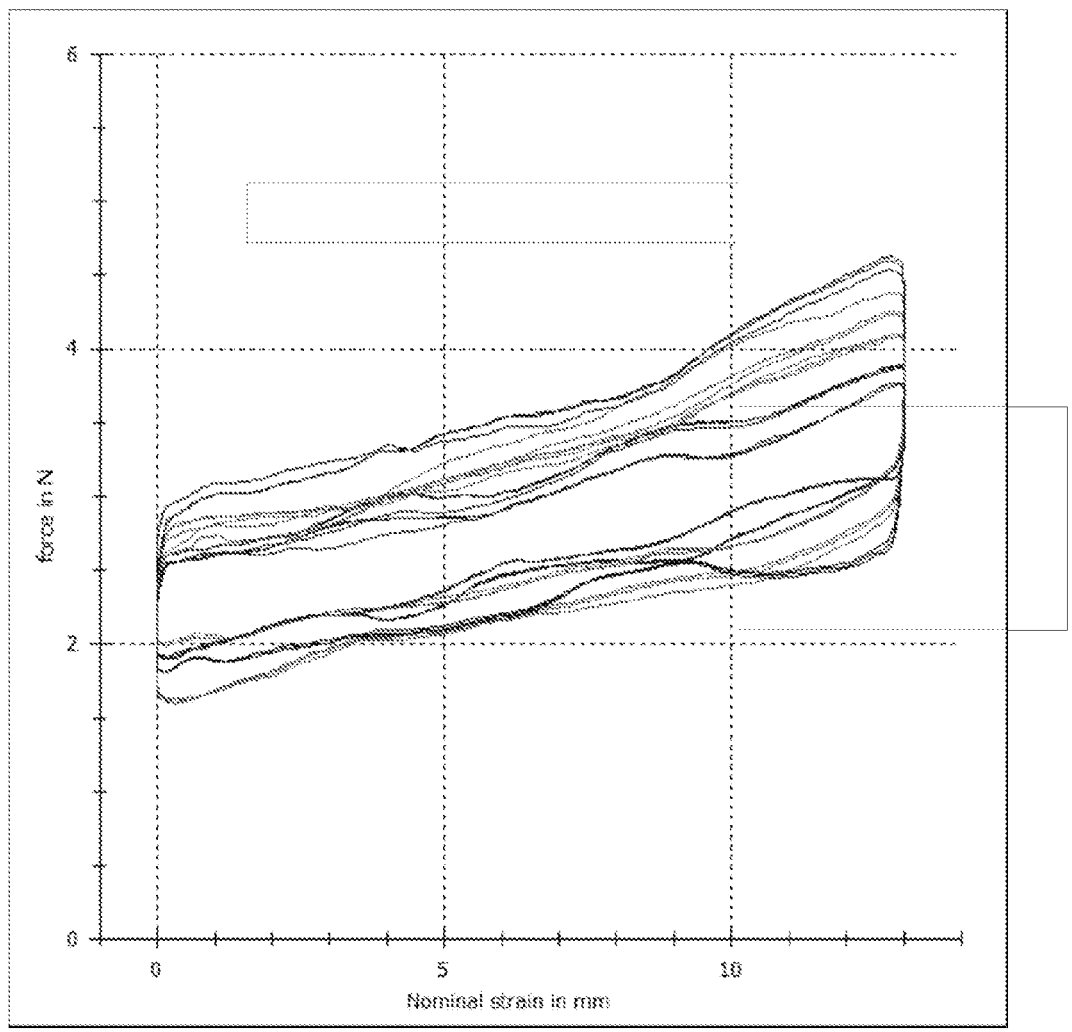
FIG. 41 illustrates a graph of retraction and extension forces in N (y-axis) against shroud deployment distances in mm (x-axis) in exemplary automatic injection devices in which a slot having a depth of about 0.3 mm is introduced to the syringe carriers and a 0.1 mm flange cut is introduced to the flanges in the proximal housing components.

FIG. 41 illustrates a graph of retraction and extension forces in N (y-axis) against shroud deployment distances in mm (x-axis) in exemplary automatic injection devices in which a slot having a depth of about 0.3 mm is introduced to the syringe carriers and a 0.1 mm flange cut is introduced to the flanges in the proximal housing components. The bending effect of the distal arms 1114 of the shroud 1110 is delayed and starts after the distal arm 1114 has traveled from about 13 mm to about 8.5 mm. In addition, the drop in the forces is more gradual and smaller in magnitude compared to that in FIG. 24 (which lacks a flange cut). A comparison between FIGS. 41 and 24 (which lacks a flange cut) indicates that introducing a cutout in the flange 256 reduces the bending effect on the distal arms 1114 of the shroud 1110 (i.e., the second type of interaction). This results in a later and more gradual drop in the extension forces over the deployment process and an increase in the residual extension force.

The introduction of the slot reduces the pinching effect over the deployment distance range of about 4 mm to about 0 mm (i.e., there is no downward peak in the forces), and raises the residual extension force to about 2 N. A comparison between FIGS. 24 and 41 (which lacks a slot in the syringe carrier) indicates that introducing a slot in the proximal tubular component of the syringe carrier reduces the pinching effect on the distal arms 1114 of the shroud 1110 (i.e., the third type of interaction). This results in increased forces during the later stages of the shroud deployment process and an increase in the residual extension force.

Figure 42:
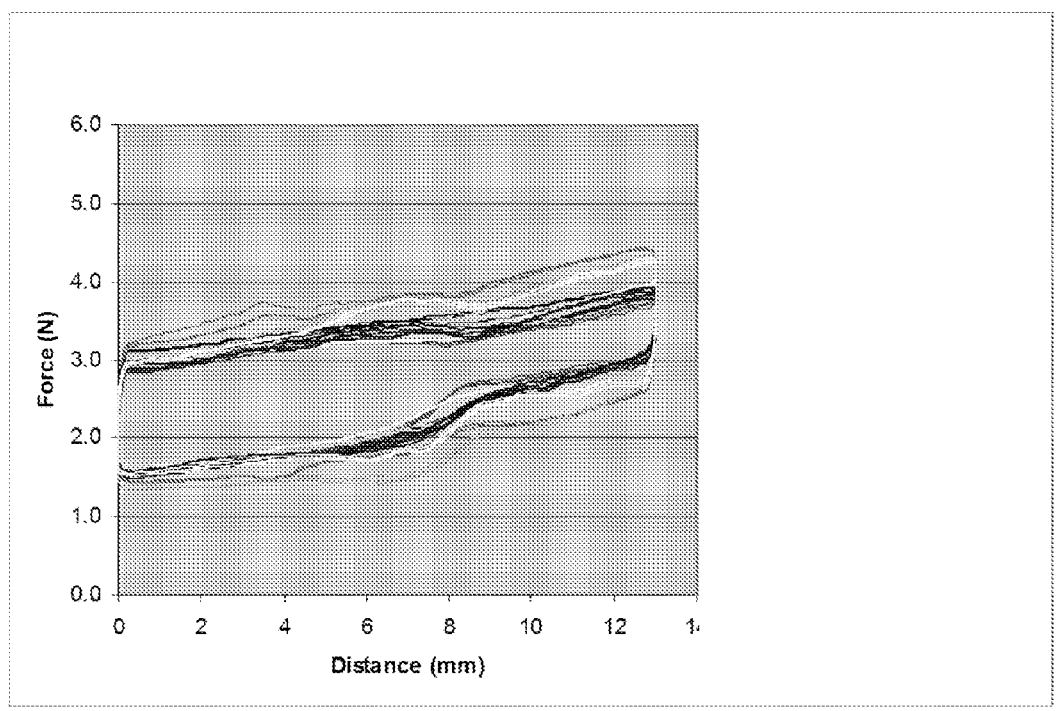
FIG. 42 illustrates a graph of retraction and extension forces in N (y-axis) against shroud deployment distances in mm (x-axis) in exemplary automatic injection devices in which a slot having a depth of about 0.3 mm is introduced to the syringe carriers and a 0.3 mm flange cut is introduced to the flanges in the proximal housing components.

FIG. 42 illustrates a graph of retraction and extension forces in N (y-axis) against shroud deployment distances in mm (x-axis) in exemplary automatic injection devices in which a slot having a depth of about 0.3 mm is introduced to the syringe carriers and a 0.3 mm flange cut is introduced to the flanges in the proximal housing components.

The bending effect of the distal arms 1114 of the shroud 1110 is delayed and starts after the distal arm 1114 has traveled from about 13 mm to about 8.5 mm. In addition, the drop in the forces is more gradual and smaller in magnitude compared to that in FIG. 24 (which lacks a flange cut). A comparison between FIGS. 42 and 24 (which lacks a flange cut) indicates that introducing a cutout in the flange 256 reduces the bending effect on the distal arms 1114 of the shroud 1110 (i.e., the second type of interaction). This results in a later and more gradual drop in the extension forces over the deployment process and an increase in the residual extension force.

The introduction of the slot reduces the pinching effect over the deployment distance range of about 4 mm to about 0 mm (i.e., there is no downward peak in the forces), and raises the residual extension force to about 1.5 N. A comparison between FIGS. 42 and 24 (which lacks a slot in the syringe carrier) indicates that introducing a slot in the proximal tubular component of the syringe carrier reduces the pinching effect on the distal arms 1114 of the shroud 1110 (i.e., the third type of interaction). This results in increased forces during the later stages of the shroud deployment process and an increase in the residual extension force.

Figure 43:
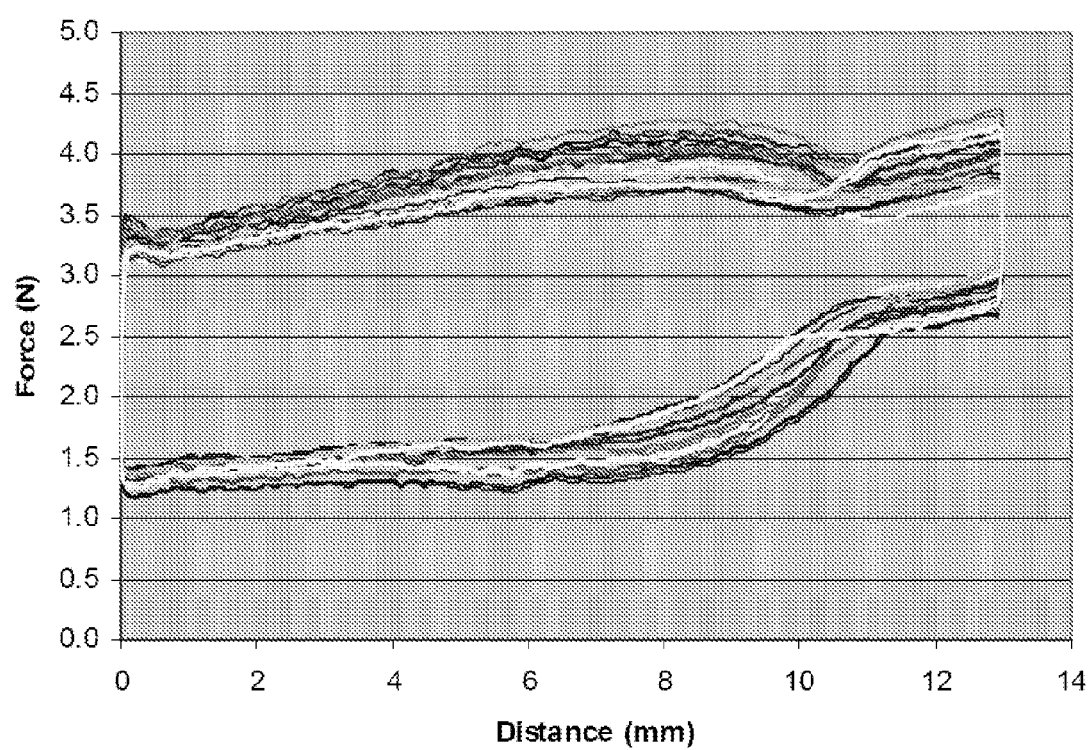
FIG. 43 illustrates a graph of retraction and extension forces in N (y-axis) against shroud deployment distances in mm (x-axis) in exemplary automatic injection devices including ten exemplary syringe carriers in which a slot having a depth of about 0.3 mm and a chamfer having an exemplary width of about 0.7 mm and an exemplary angle of about 10 degrees are introduced to the syringe carriers.

FIG. 43 illustrates a graph of retraction and extension forces in N (y-axis) against shroud deployment distances in mm (x-axis) in exemplary automatic injection devices including ten exemplary syringe carriers in which a slot having a depth of about 0.3 mm and a chamfer having an exemplary width of about 0.7 mm and an exemplary angle of about 10 degrees are introduced to the syringe carriers. The introduction of the chamfer and the slot reduces the pinching effect at about 2.5 mm, and raises the residual extension force to about 1.5 N.

Figure 44:
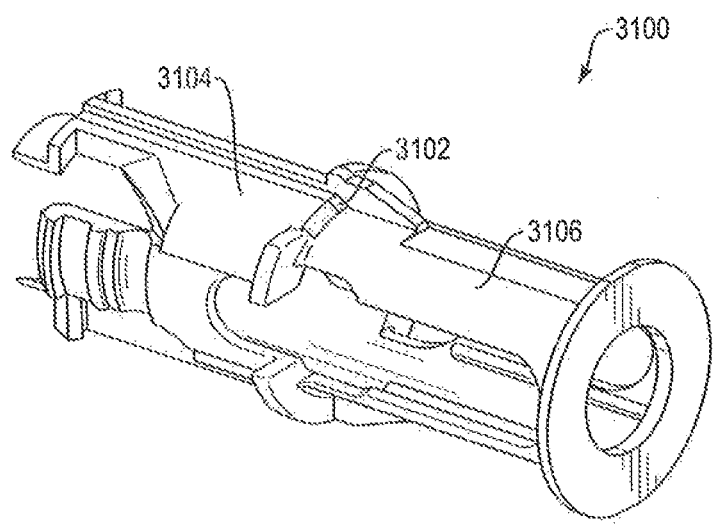
FIG. 44 illustrates a perspective view of an exemplary syringe carrier having an exemplary chamfer formed between the proximal tubular portion and the distal tubular portion.

FIG. 44 illustrates a perspective view of an exemplary syringe carrier 3100 having an exemplary chamfer 3102 formed between the proximal tubular portion 3104 and the distal tubular portion 3106. The chamfer 3102 may have an exemplary width of about 0.5 mm and an exemplary angle of about 45 degrees relative to the plane of the cylindrical portions.

Figure 45:
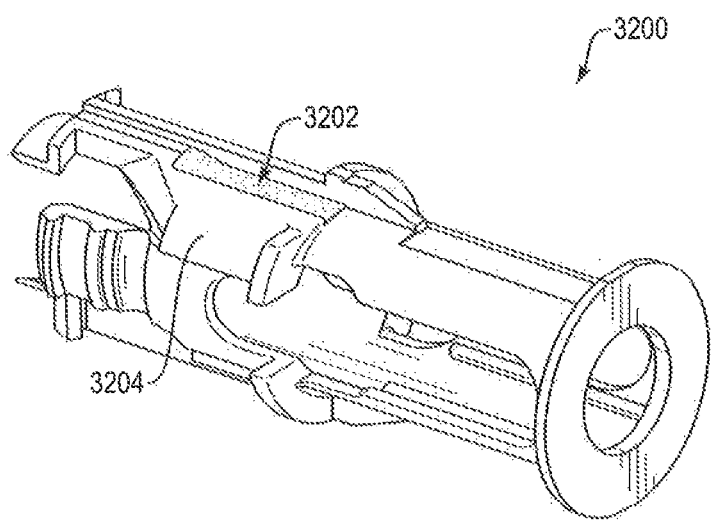
FIG. 45 illustrates a perspective view of an exemplary syringe carrier having an exemplary slot formed in the proximal tubular portion of the syringe carrier to create a depression in the surface of the proximal tubular portion.

FIG. 45 illustrates a perspective view of an exemplary syringe carrier 3200 having an exemplary slot 3202 formed in the proximal tubular portion 3204 of the syringe carrier 3200 to create a depression in the surface of the proximal tubular portion 3204. The slot 3202 may extend over a portion of the length of the proximal tubular portion 3204 or over the entire length of the proximal tubular portion 3204.

During the shroud deployment process, the distal arms 1114 of the shroud 1110 may engage with the surface of the slot 3202 as the distal arms move in the proximal direction over the proximal tubular portion 3204. The slot 3202 may have an exemplary depth of between about 0.1 mm and about 0.7 mm. In an exemplary embodiment, the slot 3202 may have an exemplary depth of about 0.5 mm.

Figure 46:
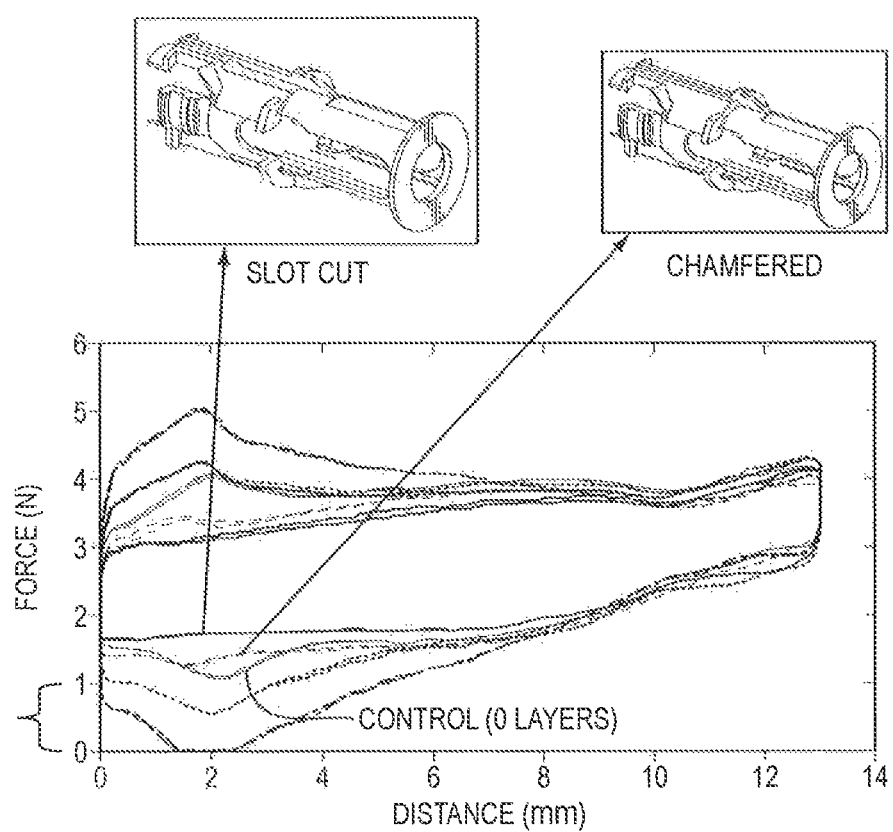
FIGS. 46-48 illustrate graphs of retraction and extension forces in N (y-axis) against shroud deployment distances in mm (x-axis) for exemplary syringe carriers of a first type, a second type, and a third type.
Figure 47:
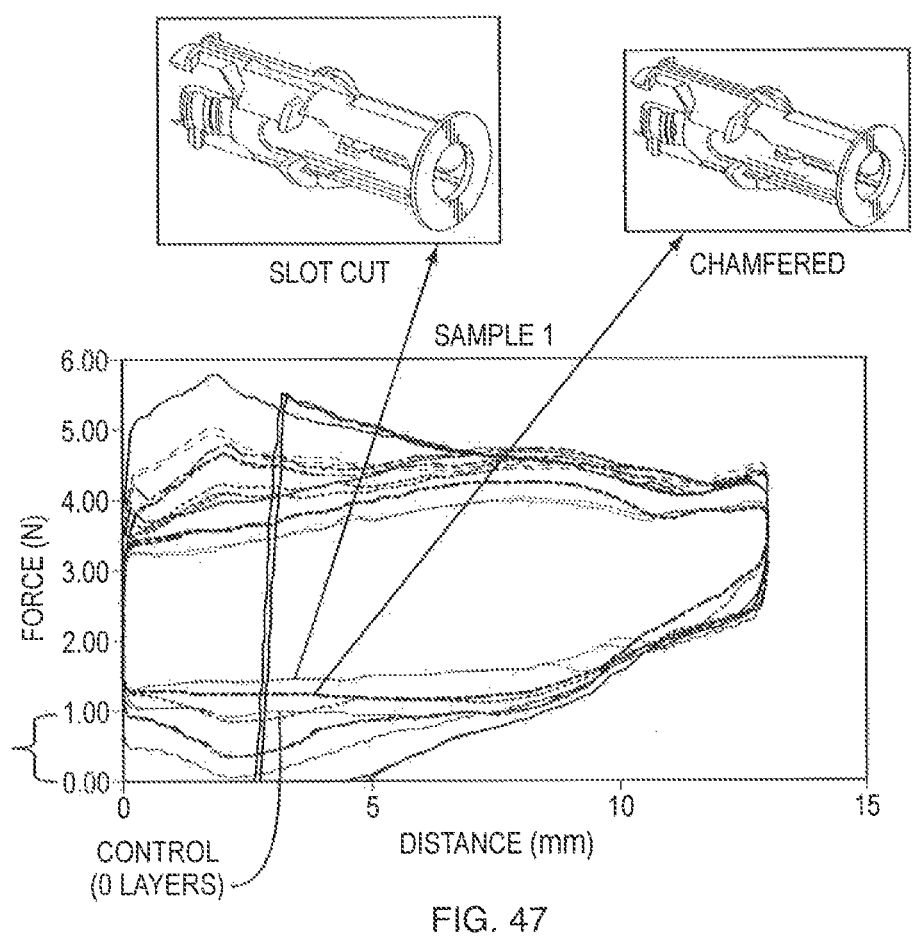
Figure 48:
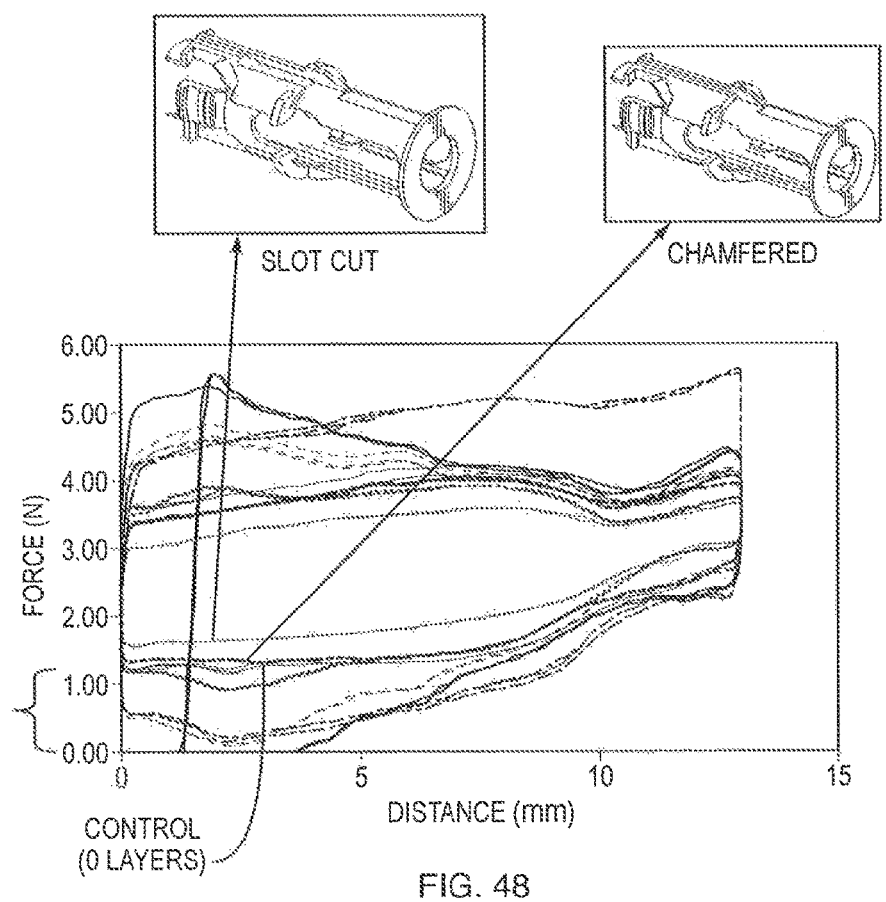

FIGS. 46-48 illustrate graphs of retraction and extension forces in N (y-axis) against shroud deployment distances in mm (x-axis) for exemplary syringe carriers of a first type, a second type, and a third type. The three types of syringe carriers were formed using different production tools. Differences in the manufacturing tolerances of the different production tools introduced differences in the geometries of the syringe carriers.

FIG. 46 illustrates a graph of retraction and extension forces in N (y-axis) against shroud deployment distances in mm (x-axis) for exemplary syringe carriers of a first type: a control syringe carrier configured as shown in FIG. 9 having a step at the transition portion between the proximal tubular portion and the distal tubular portion; a syringe carrier configured as shown in FIG. 44 with a chamfer of width about 0.5 mm and an angle of about 45 degrees; and a syringe carrier configured as shown in FIG. 45 with a 0.5 mm deep slot cut. FIG. 46 shows a pinching effect at about 2 mm at which the extension force shows a downward peak corresponding to a pinching effect during the later stage of the shroud deployment process. The control syringe carrier (illustrated in FIG. 9) shows the greatest downward peak resulting in a residual extension force of about 1.0 N. The chamfered syringe carrier (illustrated in FIG. 44) shows an intermediate downward peak resulting in a residual extension force of about 1.3 N. The slotted syringe carrier (illustrated in FIG. 45) shows no downward peak resulting in a residual extension force of about 1.7 N. FIG. 46 indicates that the pinching effect is reduced or eliminated by the chamfer and the slot, which results in efficient and reliable shroud deployment.

FIG. 47 illustrates a graph of retraction and extension forces in N (y-axis) against shroud deployment distances in mm (x-axis) for exemplary syringe carriers of a second type: a control syringe carrier configured as shown in FIG. 9 having a step at the transition portion between the proximal tubular portion and the distal tubular portion; a syringe carrier configured as shown in FIG. 44 with a chamfer of width about 0.5 mm and an angle of about 45 degrees; and a syringe carrier configured as shown in FIG. 45 with a 0.5 mm deep slot cut. FIG. 34 shows a pinching effect at about 2 mm at which the extension force shows a downward peak which corresponds to a pinching effect during the later stage of the shroud deployment process. The control syringe carrier (illustrated in FIG. 9) shows the greatest downward peak. The chamfered syringe carrier (illustrated in FIG. 44) shows an intermediate downward peak. The slotted syringe carrier (illustrated in FIG. 45) shows no downward peak. FIG. 47 indicates that the pinching effect is reduced or eliminated by the chamfer and the slot, which results in efficient and reliable shroud deployment.

FIG. 48 illustrates a graph of retraction and extension forces in N (y-axis) against shroud deployment distances in mm (x-axis) for exemplary syringe carriers of a third type: a control syringe carrier configured as shown in FIG. 9 having a step at the transition portion between the proximal tubular portion and the distal tubular portion; a syringe carrier configured as shown in FIG. 44 with a chamfer of width about 0.5 mm and an angle of about 45 degrees; and a syringe carrier configured as shown in FIG. 45 with a 0.5 mm deep slot cut. FIG. 48 shows a pinching effect at about 2 mm at which the extension force shows a downward peak which corresponds to a pinching effect during shroud deployment. The control syringe carrier (illustrated in FIG. 9) shows the greatest downward peak. The chamfered syringe carrier (illustrated in FIG. 44) shows an intermediate downward peak. The slotted syringe carrier (illustrated in FIG. 45) shows no downward peak. FIG. 48 indicates that the pinching effect is reduced or eliminated by the chamfer and the slot, which results in efficient and reliable shroud deployment.

In an exemplary syringe carrier, a rounded step, i.e., a step with a rounded edge, may be formed at the transition portion between the proximal tubular portion and the distal tubular portion of the syringe carrier. However, it was determined from quantitative experimental results that the rounded edge does not maximize extension forces (i.e. reduce or substantially eliminate the localized downward peak near the end of deployment of the shroud) compared to FIG. 24. As such, in another exemplary syringe carrier, the transition portion may be left un-rounded.

F. Configuration of the Living Hinge of the Proximal Anchor Portion of the Syringe Carrier In an exemplary embodiment, a draft 3602 may be included in the living hinge of the proximal anchor portion 3604 of the syringe carrier 3600 in order to facilitate the molding or formation process of the syringe carrier. Without the draft 3602, the hinge at the proximal anchor portion 3604 of the syringe carrier 3600 may tend to stick to the mold used in molding or forming the syringe carrier 3600. The introduction of the draft 3602 allows the syringe carrier 3600 to be released smoothly from the mold after the syringe carrier is molded or formed in the mold. The introduction of the draft 3602 may improve the syringe carrier molding process and avoid warping of the parts of the syringes carrier 3600 that may otherwise by caused by a defective molding process.

Figure 49:
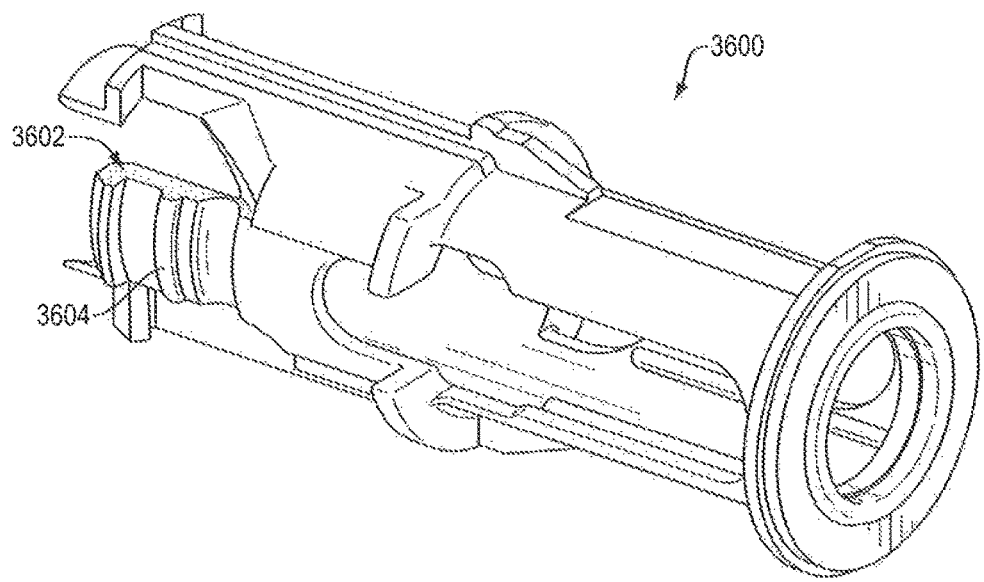
FIG. 49 illustrates a perspective view of an exemplary syringe carrier in which the living hinge includes a draft in the proximal anchor portion of the syringe carrier.

FIG. 49 illustrates a perspective view of an exemplary syringe carrier 3600 in which the living hinge includes a draft 3602 in the proximal anchor portion 3604 of the syringe carrier 3600. In exemplary embodiments, the draft 3602 may have exemplary draft angles of about 1°, 2°, 3°, 4°, 5°, 6°, 7°, 8°, 9°, 10°, etc. In the exemplary embodiment illustrated in FIG. 49, the draft angle is about 5°.

In another exemplary embodiment, a draft may not be included in the living hinge of the proximal anchor portion 3604 of the syringe carrier 3600.

G. Configuration of the Rail of the Syringe Carrier

The rails of an exemplary syringe carrier may be configured in one or more exemplary ways to decrease the frictional forces experienced between the rails and the inner grooves of the shroud as the rails move within the grooves during shroud deployment. Reduction of the frictional forces increases the extension forces experienced during the shroud deployment process and facilitates smooth shroud deployment.

Figure 50:
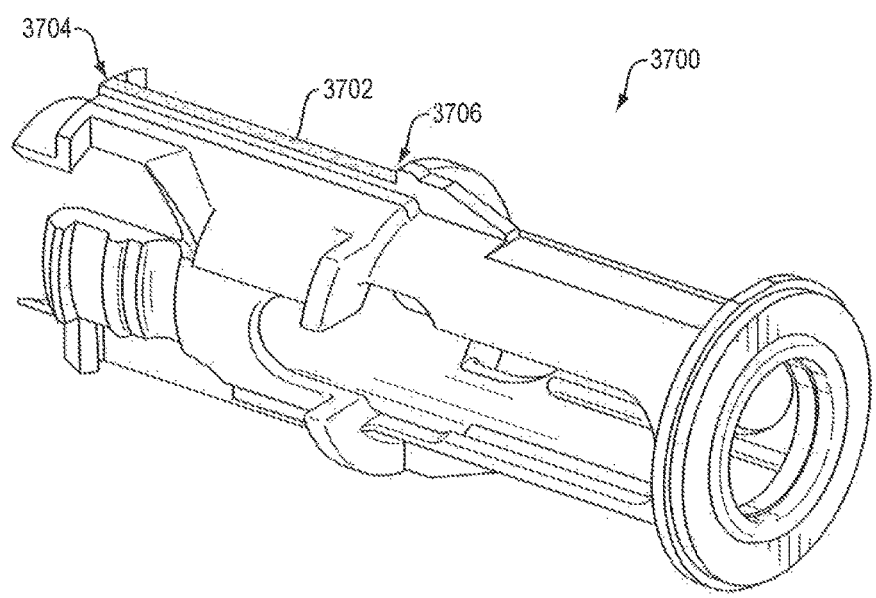
FIG. 50 illustrates a perspective view of an exemplary syringe carrier including a rail extending between a proximal end and a distal end.

FIG. 50 illustrates a perspective view of an exemplary syringe carrier 3700 including a rail 3702 extending between a proximal end 3704 and a distal end 3706. In an exemplary embodiment, the width of the rail 3702 of the carrier 3700 (i.e., the cross-sectional width of the rail) may be decreased in order to decrease interaction of the rail 3702 with the inner grooves of the shroud during the shroud deployment process, which may increase the extension forces in the shroud deployment process. In an exemplary embodiment, the width of the rail 3702 may be decreased to the same width along the length of the rail 3702. In another exemplary embodiment, the width of the rail 3702 may be decreased to different widths along the length of the rail 3702. In an exemplary embodiment, the width of the rail 3702 may be wider at the proximal end 3704 than at the distal end 3706. In an exemplary embodiment, the width of the rail 3702 may be wider at the distal end 3706 than at the proximal end 3704. In an exemplary embodiment, the rail 3702 is a tapered rail having a greater width at one end and a lesser width at another end. In an exemplary embodiment, the width may vary over the length of the rail 3702 (for example, material may be removed to achieve different widths along the length of the rail) in order to compensate for warpage in the components after molding.

In an exemplary embodiment, the length of the rail 3702 along the longitudinal axis of the carrier 3700 may be decreased in order to decrease interaction of the rail 3702 with the inner grooves of the shroud during the shroud deployment process, which may increase the extension forces in the shroud deployment process. Exemplary lengths of the rail 3702 may range from about 14.00 mm to about 16.00 mm, but are not limited to this exemplary range. In an exemplary embodiment, the length of the rail 3702 may be decreased from about 15.30 mm to about 14.79 mm. In another exemplary embodiment, the length of the rail 3702 may be decreased from about 15.30 mm to about 14.94 mm.

In an exemplary embodiment, the distance between the rails 3702 of the carrier 3700 may be decreased.

In an exemplary embodiment, the top profile of an exemplary rail 3702 of the carrier 3700 may be configured to match the curvature of the shroud in order to improve the interlocking of the rail 3702 and the internal grooves of the shroud Improved interlocking provides stability to the shroud and carrier assembly during movement of the components during the shroud deployment process. The configuration of the top profile of the rail 3702 also increases the gap between the top of the rail 3702 and the inner surface of the groove of the shroud. The increased gap increases the residual extension forces, which facilitates smooth shroud deployment.

H. Configuration of the Inner Grooves of the Shroud

The inner grooves of the shroud may be configured in one or more exemplary ways to decrease the frictional forces experienced between the rails of the syringe carrier and the inner grooves of the shroud as the rails move within the grooves during shroud deployment. Reduction of the frictional forces increases the extension forces experienced during the shroud deployment process and facilitates smooth shroud deployment.

In an exemplary embodiment, the height of the internal grooves of the shroud 1110 may be increased in order to decrease frictional forces between the rail 1007 of the syringe carrier 1000 with the inner grooves of the shroud 1110 during the shroud deployment process, in order to maximize the extension forces in the shroud deployment process.

In an exemplary embodiment, a lead-in may be added to the internal grooves of the shroud 1110 in order to facilitate assembly of the shroud 1110 and the carrier 1000. The size of the lead-in in the groove may be configured based, in part, on the diameter of the groove. For example, for a groove with a larger diameter, the size of the lead-in may be reduced.

In an exemplary embodiment, a lead-in may be added to the rail 1007 of the carrier 1000 in order to facilitate assembly of the shroud 1110 and the carrier 1000.

I. Configuration of Coefficient of Friction

The extension forces experienced during the shroud deployment process may be dependent on, in part, the coefficient of friction (COF) and the frictional forces experienced among the different moving components of the automatic injection device, e.g., components of the shroud 1110 and the syringe carrier 1000. Higher COF values increase the frictional forces experienced between the different moving components during the shroud deployment process, and may thus lead to failed shroud deployment. Reducing the COF values decreases the frictional forces experienced during the shroud deployment process and allows the release of the biasing member 89 to smoothly deploy the shroud.

Figure 51:
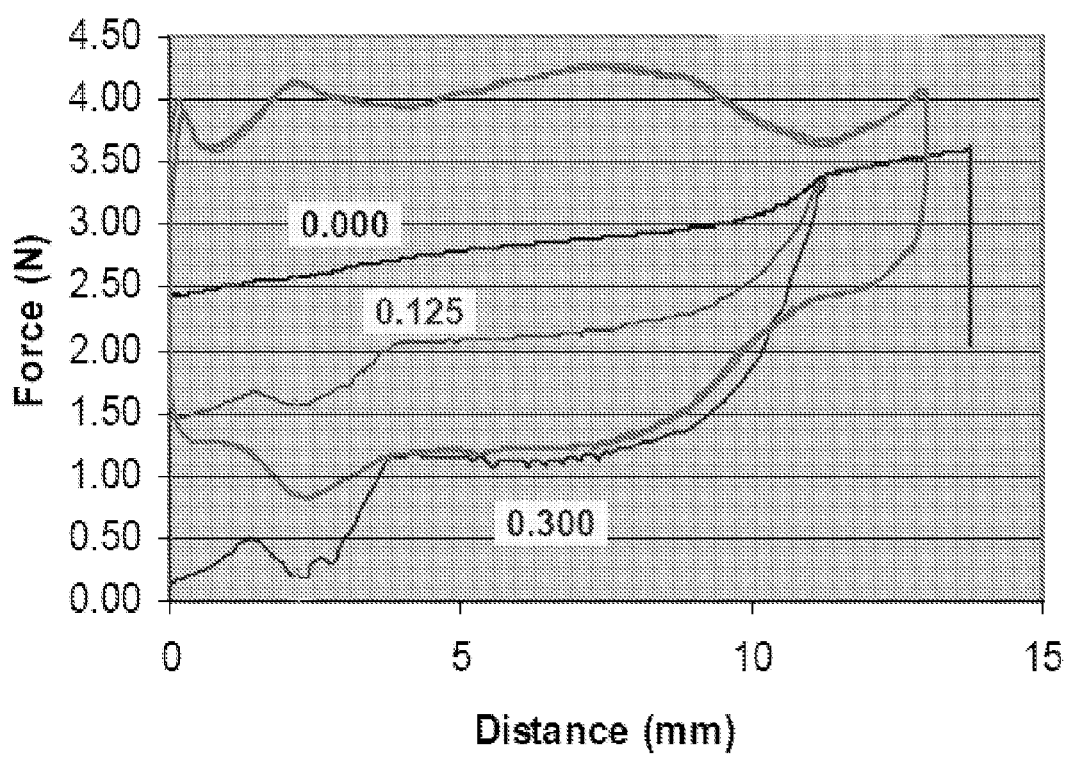
FIG. 51 illustrates a graph of retraction and extension forces in N (y-axis) against shroud deployment distances in mm (x-axis) for exemplary COF values of about 0.000, about 0.125, and about 0.300.

FIG. 51 illustrates a graph of retraction and extension forces in N (y-axis) against shroud deployment distances in mm (x-axis) for exemplary COF values of about 0.000, about 0.125, and about 0.300. FIG. 51 shows a pinching effect at about 2 mm at which the extension force showed a downward peak which corresponds to a pinching effect during shroud deployment. The downward peak had the greatest magnitude (extension force of about 0.7 N) for the 0.300 COF, an intermediate magnitude (extension force of about 1.5 N) for the 0.125 COF, and the lowest magnitude (extension force of about 2.5 N) for the 0.000 COF.

FIG. 51 indicates that increasing COF values increased the frictional forces, which resulted in a greater magnitude of the downward peak at about 2 mm. Exemplary embodiments may configure one or more properties of the different moving parts, e.g., components of the shroud 1110, the syringe carrier 1000, the automatic injection device housing, etc., to reduce the frictional forces experienced during the shroud deployment process. These modifications improve the shroud deployment process and prevent shroud deployment failure.

In exemplary embodiments, one or more properties of the material forming the moving parts may be configured in reducing the frictional forces experienced during the shroud deployment process. These properties may include, but are not limited to, flex modulus, yield strength, yield elongation, material strength for functionality and manufacturability, and the like. In an exemplary embodiment, a polyacetal material may be used to form one or more moving parts experiencing low frictional forces, e.g., the shroud, the syringe carrier, etc. In an exemplary embodiment, polytetrafluoroethylene (PTFE) may be used to form one or more moving parts, e.g., the shroud, the syringe carrier, etc.

J. Other Exemplary Configurations

One of ordinary skill in the art will recognize that one or more other configurations may be implemented and/or one or more additional features may be included to improve the shroud deployment process. The configurations and features provided in exemplary embodiments are not limited to those described below in this section.

For example, in an exemplary embodiment, the inner diameter of the shroud 1110 may be increased to reduce frictional forces between the biasing member 89 and the shroud 1110.

In an exemplary embodiment, the width of the tabbed foot 1006 of the carrier 1000 may be decreased to reduce frictional forces between the tabbed foot 1006 and the slot 1118 of the shroud 1110. In an exemplary embodiment, the width of the slot 1118 of the shroud 1110 may be increased to reduce frictional forces between the tabbed foot 1006 and the slot 1118 of the shroud 1110.

In an exemplary embodiment, one or more sloping portions, e.g., chamfers, may be added to a side wall of the interior flange 256 in the housing to reduce frictional forces between the flange 256 and components of the shroud deployment assembly, e.g., the arms 1114 of the shroud 1110. In an exemplary embodiment, the distal edge of a side wall of the interior flange 256 in the housing may be rounded to reduce frictional forces between the flange 256 and components of the shroud deployment assembly, e.g., the arms 1114 of the shroud 1110.

K. Summary

Exemplary embodiments may implement one or a combination of two or more of the structural, functional and operational configurations taught herein to minimize the risk of shroud deployment failure. Exemplary embodiments may also modify one or more conventional components of an automatic injection device in accordance with the teachings provided herein in order to minimize the risk of shroud deployment failure in the modified conventional components.

Exemplary embodiments provide automatic injection devices in which a needle shroud is automatically deployed in a reliable and consistent manner to protectively sheath a needle during or after an injection is delivered using the automatic injection device. Exemplary embodiments also provide shroud deployment assemblies including a needle shroud and a syringe carrier that when cooperatively configured in an assembled automatic injection device ensure that the needle shroud is automatically deployed in a reliable and consistent manner.

Exemplary embodiments may provide methods for forming an automatic injection device. An exemplary method includes providing a housing having an internal bore extending between a proximal end and a distal end, and disposing a shroud within the internal bore at the proximal end of the housing of the automatic injection device. The shroud may be capable of moving between a retracted position and an extended position relative to the housing. The shroud may include a tubular member extending between a proximal end and a distal end, and one or more arms extending from the distal end of the tubular member. The method may include disposing a syringe carrier partly within the tubular member of the shroud, the syringe carrier comprising a tubular member. The method may also include configuring a constrained space formed between the housing of the automatic injection device and the tubular member of the syringe carrier to minimize a pinching effect of the distal arms during its movement in the constrained space when moving from the retracted position to the extended position.

Exemplary embodiments may provide methods for using an automatic injection device to deliver an injection. An exemplary method includes retracting a shroud from an extended position to a retracted position within a housing of the automatic injection device before, during or after an injection, the shroud exposing a needle through an open proximal end of the shroud when the shroud is in the retracted position, and delivering the injection using the automatic injection device through the needle. The method may include deploying the shroud from the retracted position to the extended position within the housing of the automatic injection device before, during or after the injection, the shroud protectively sheathing the needle when the shroud is in the extended position. The deployment of the shroud comprising moving distal arms of the shroud in a forward direction within a constrained space formed between the housing of the automatic injection device and a tubular member of a syringe carrier. The constrained space and/or the distal arms of the shroud are configured to minimize a pinching effect of the distal arms during its movement in the constrained space.

Exemplary automatic injection devices have sufficiently high shroud override forces so that it is difficult to cause the shroud to retract once it has been deployed. Exemplary shroud override forces may include, but are not limited to, about 80 N to about 120 N. The high shroud override forces ensure that, once deployed, the shroud remains deployed against forces exerted to retract the shroud, which minimizes or eliminates the risk of needle stick injuries.

Figure 52:
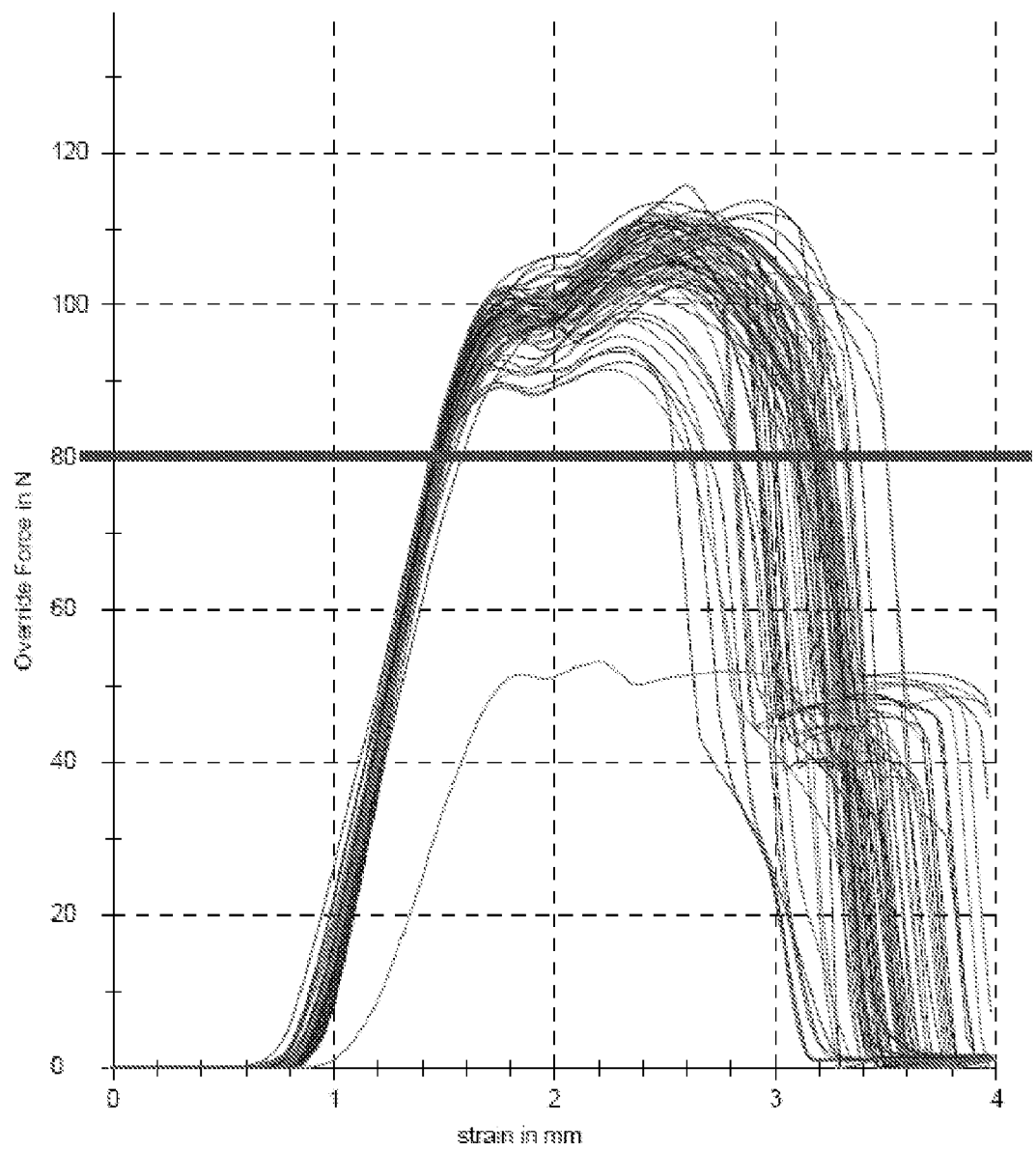
FIG. 52 illustrates a graph of shroud override forces in N (y-axis) against override distance in mm (x-axis) for the control and exemplary test syringe carriers.
Figure 53:
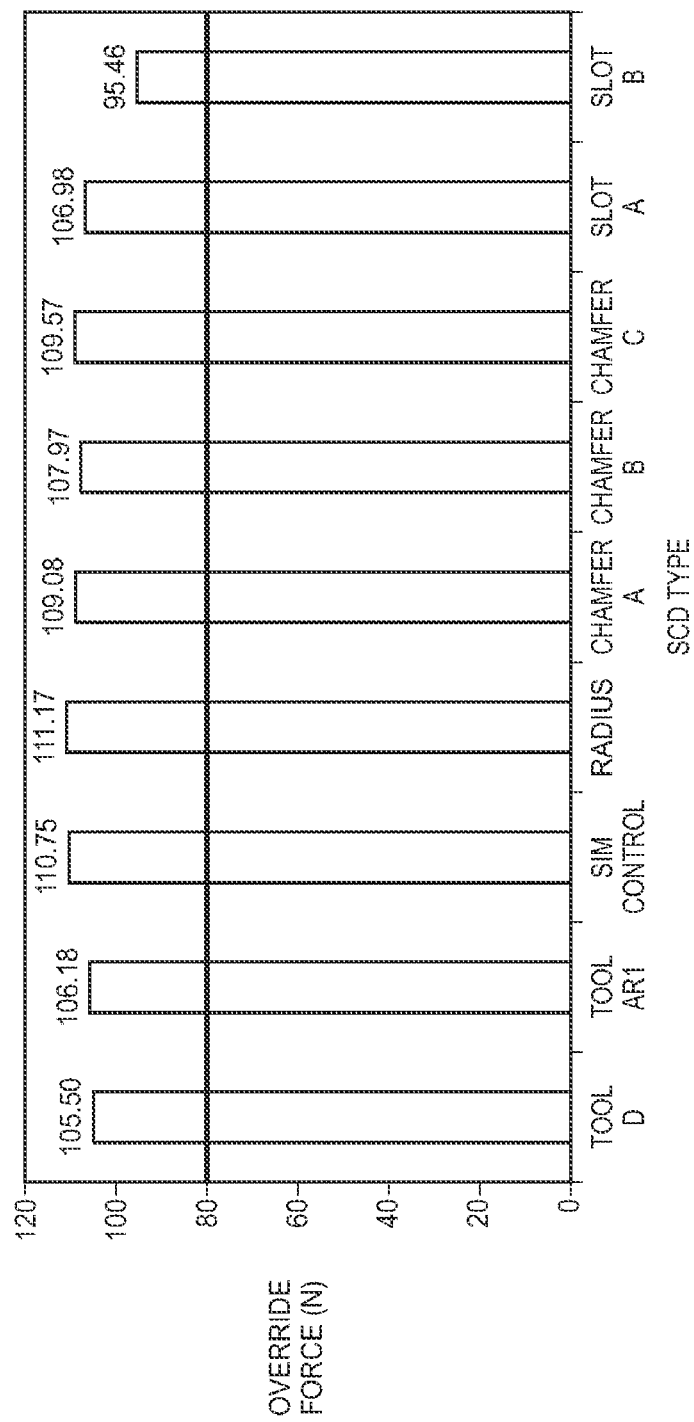
FIG. 53 illustrates a histogram of peak shroud override forces in N (y-axis) for the control and exemplary test syringe carriers.

The shroud override forces were monitored and graphed for the control syringe carrier and for each of the above syringe carrier design changes. FIG. 52 illustrates a graph of shroud override forces in N (y-axis) against override distance in mm (x-axis) for the control and exemplary test syringe carriers. FIG. 53 illustrates a histogram of peak shroud override forces in N (y-axis) for the control and exemplary test syringe carriers. All of the exemplary syringe carriers showed shroud override forces of above 80 N, which indicates that, once deployed, the shroud remain reliably deployed even when large forces (of about 80 N) attempt to retract the shroud by pushing on the shroud in the distal direction.

V. INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

VI. EQUIVALENTS

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2, etc., or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

What is claimed is:

1. A shroud deployment assembly for use in an automatic injection device, the shroud deployment assembly comprising:
    a shroud disposed within an internal bore of a housing of the automatic injection device, the shroud movable between a retracted position and an extended position relative to the housing, the shroud comprising:
        a tubular member extending between a proximal end and a distal end, and
        one or more arms extending from the distal end of the tubular member; and
    a syringe carrier coupled to and disposed partly within the tubular member of the shroud, the syringe carrier comprising a cylindrical portion having a slot forming a trench in an outer surface of the cylindrical portion extending along a length of the syringe carrier;
    wherein, as the shroud is deployed from the retracted position to the extended position, the one or more arms of the shroud move forwardly within a constrained space formed between an inner surface of the housing of the automatic injection device and an outer surface of the cylindrical portion of the syringe carrier to engage with the trench as they move forwardly; and
    wherein the trench is configured to facilitate smooth movement of the one or more arms of the shroud within the constrained space during deployment of the shroud.

2. The shroud deployment assembly of claim 1, wherein the height of the constrained space is configured to be at least equal to a thickness of the one or more arms of the shroud.

3. The shroud deployment assembly of claim 1, wherein an outer diameter of the cylindrical portion of the syringe carrier is configured to range from about 13.0 mm to about 14.0 mm.

4. The shroud deployment assembly of claim 1, wherein a thickness of the one or more arms of the shroud is configured to reduce a pinching effect of the one or more arms during movement of the one or more arms in the constrained space.

5. The shroud deployment assembly of claim 4, wherein the thickness of the one or more arms of the shroud is configured to be at most equal to the height of the constrained space.

6. The shroud deployment assembly of claim 5, wherein the thickness of the one or more arms of the shroud is configured to range from about 1.3 mm to about 1.4 mm.

7. The shroud deployment assembly of claim 1, wherein an inner diameter of the housing of the automatic injection device is configured to range from about 17 mm to about 18 mm.

8. The shroud deployment assembly of claim 1, wherein the cylindrical portion of the syringe carrier comprises:
    a proximal tubular portion having a first outer diameter;
    a distal tubular portion having a second outer diameter less than the first diameter; and
    a chamfered relief formed between the proximal and distal tubular portions.

9. The shroud deployment assembly of claim 8, wherein the chamfered relief has an angle ranging from about 5 degrees to about 60 degrees.

10. The shroud deployment assembly of claim 1, wherein the trench has a depth ranging from about 0.1 mm to about 0.5 mm.

11. The shroud deployment assembly of claim 1, wherein the shroud, in the extended position, protectively sheathes a needle disposed at a proximal end of the automatic injection device, and wherein the shroud, in the retracted position, allows exposure of a needle disposed at a proximal end of the automatic injection device.

12. The shroud deployment assembly of claim 1, wherein, once the shroud is deployed to the extended position, the shroud is configured to withstand a force of at least 80 N without retracting to the retracted position.

13. The shroud deployment assembly of claim 1, further comprising:
a biasing mechanism that is in a compressed state when the shroud is in the retracted position and that automatically biases the shroud from the retracted position to the extended position after the automatic injection device is removed from an injection site.

14. The shroud deployment assembly of claim 1, wherein the automatic injection device comprises a dose of a TNFα inhibitor.

15. The shroud deployment assembly of claim 14, wherein the TNFα inhibitor is a human TNFα antibody, or antigen-binding portion thereof.

16. The shroud deployment assembly of claim 15, wherein the human TNFα antibody, or antigen-binding portion thereof, is adalimumab or golimumab.

17. An automatic injection device, comprising:
a housing having an internal bore extending between a proximal end and a distal end;
a shroud disposed within the internal bore at the proximal end of the housing of the automatic injection device, the shroud movable between a retracted position and an extended position relative to the housing, the shroud comprising:
a tubular member extending between a proximal end and a distal end, and
one or more arms extending from the distal end of the tubular member; and
a syringe carrier disposed partly within the tubular member of the shroud, the syringe carrier comprising a tubular member having a slot forming a trench in an outer surface thereof extending along a length of the syringe carrier;
wherein, as the shroud is deployed from the retracted position to the extended position, the one or more arms of the shroud move forwardly within a constrained space formed between an inner surface of the housing of the automatic injection device and an outer surface of the tubular member of the syringe carrier to engage with the trench; and
wherein the trench is configured to facilitate movement of the one or more arms of the shroud within the constrained space during deployment of the shroud.

18. The automatic injection device of claim 17, wherein the height of the constrained space is configured to be at least equal to a thickness of the one or more arms of the shroud.

19. The automatic injection device of claim 17, wherein an outer diameter of the tubular member of the syringe carrier is configured to range from about 13.0 mm to about 14.0 mm.

20. The automatic injection device of claim 17, wherein a thickness of the one or more arms of the shroud is configured to reduce the pinching effect of the one or more arms during its movement in the constrained space.

21. The automatic injection device of claim 20, wherein the thickness of the one or more arms of the shroud is configured to be at most equal to the height of the constrained space.

22. The automatic injection device of claim 21, wherein the thickness of the one or more arms of the shroud is configured to range from about 1.3 mm to about 1.4 mm.

23. The automatic injection device of claim 17, wherein an inner diameter of the housing of the automatic injection device is configured to range from about 17 mm to about 18 mm.

24. The automatic injection device of claim 17, wherein the tubular member of the syringe carrier comprises:
a proximal tubular portion having a first diameter;
a distal tubular portion having a second diameter less than the first diameter; and
a chamfered relief formed between the proximal and distal tubular portions.

25. The automatic injection device of claim 24, wherein the chamfered relief has an angle ranging from about 5 degrees to about 60 degrees.

26. The automatic injection device of claim 17, wherein the trench has a depth ranging from about 0.1 mm to about 0.5 mm.

27. The automatic injection device of claim 17, wherein the shroud, in the extended position, protectively sheathes a needle disposed at a proximal end of the automatic injection device, and wherein the shroud, in the retracted position, exposes a needle disposed at a proximal end of the automatic injection device.

28. The automatic injection device of claim 17, wherein, once the shroud is deployed to the extended position, the shroud is configured to withstand a force of at least 80 N without retracting to the retracted position.

29. The automatic injection device of claim 17, further comprising:
a biasing mechanism that is compressed when the shroud is at the retracted position and that automatically biases the shroud from the retracted position to the extended position after the automatic injection device is removed from an injection site.

30. The automatic injection device of claim 17, wherein the automatic injection device comprises a dose of a TNFα inhibitor.

31. The automatic injection device of claim 30, wherein the TNFα inhibitor is a human TNFα antibody, or antigen-binding portion thereof.

32. The automatic injection device of claim 31, wherein the human TNFα antibody, or antigen-binding portion thereof, is adalimumab or golimumab.

33. A method for forming an automatic injection device, the method comprising:
providing a housing having an internal bore extending between a proximal end and a distal end;
disposing a shroud within the internal bore at the proximal end of the housing of the automatic injection device, the shroud movable between a retracted position and an extended position relative to the housing, the shroud comprising:
a tubular member extending between a proximal end and a distal end, and
one or more arms extending from the distal end of the tubular member;
disposing a syringe carrier partly within the tubular member of the shroud, the syringe carrier comprising a tubular member having a slot forming a trench in an outer surface thereof extending along a length of the syringe carrier to configure a constrained space formed between the housing of the automatic injection device and the tubular member of the syringe carrier to minimize a pinching effect of the one or more arms of the shroud during its movement in the constrained space when moving from the retracted position to the extended position.

34. The method of claim 33, wherein the trench has a depth ranging from about 0.1 mm to about 0.5 mm.

35. The method of claim 33, wherein:
the internal bore of the housing comprises a flange having at least one opening;
as the shroud is deployed from the retracted position to the extended position, the one or more arms of the shroud move forwardly through the opening in the flange of the housing; and
the flange is configured to minimize engagement of the one or more arms of the shroud with an edge of the flange to facilitate movement of the one or more arms of the shroud through the opening of the flange during deployment of the shroud.

36. The method of claim 35, further comprising:
modifying the flange to increase the width of the opening of the flange.

37. The method of claim 36, further comprising:
removing a portion of the flange abutting the opening of the flange, the length of the removed portion ranging from 0.05 mm to 0.6 mm.

38. A method for using an automatic injection device to deliver an injection, the method comprising:
providing a shroud having one or more arms within a housing of the automatic injection device, the shroud being in a retracted position relative to the housing to expose a needle through an open proximal end of the shroud;
delivering an injection using the automatic injection device through the needle; and
deploying the shroud from the retracted position to an extended position relative to the housing of the automatic injection device to protectively sheath the needle after the injection, the one or more arms of the shroud moving forwardly within a constrained space formed between an inner portion of the housing of the automatic injection device and an outer portion of a tubular member of a syringe carrier
wherein the constrained space and/or the one or more arms of the shroud are configured to minimize a pinching effect of the one or more arms during its movement in the constrained space; and
wherein the outer portion of the tubular member of the syringe carrier comprises a slot forming a trench in an outer surface thereof extending along a length of the syringe carrier that increases the constrained space.

39. The method of claim 38, wherein the trench has a depth ranging from about 0.1 mm to about 0.5 mm.

40. The method of claim 38, wherein:
an internal bore of the housing comprises a flange having at least one opening;
as the shroud is deployed from the retracted position to the extended position, the one or more arms of the shroud move forwardly through the opening in the flange of the housing; and
the flange is configured to minimize engagement of the one or more arms of the shroud with an edge of the flange to facilitate movement of the one or more arms of the shroud through the opening of the flange during deployment of the shroud.

41. The method of claim 40, wherein the flange is configured to increase the width of the opening of the flange.

42. The method of claim 41, wherein a portion of the flange abutting the opening is removed, the length of the removed portion ranging from 0.05 mm to 0.6 mm.

* * * * *

UNITED STATES PATENT AND TRADEMARK OFFICE
CERTIFICATE OF CORRECTION

Page 1 of 1

PATENT NO. : 9,956,353 B2
APPLICATION NO. : 14/007849
DATED : May 1, 2018
INVENTOR(S) : Rao et al.

It is certified that error appears in the above-identified patent and that said Letters Patent is hereby corrected as shown below:

In the Claims

In Column no: 53, Line(s) no: 59, Claim 20, "the pinching effect" to read as --a pinching effect--

In Column no: 56, Line(s) no: 05-06, Claim 38, "a syringe carrier wherein" to read as --a syringe carrier; wherein--

Signed and Sealed this
First Day of January, 2019

Andrei Iancu
*Director of the United States Patent and Trademark Office*